(12) United States Patent
Korgel et al.

(10) Patent No.: US 8,618,595 B2
(45) Date of Patent: Dec. 31, 2013

(54) APPLICATIONS OF LIGHT-EMITTING NANOPARTICLES

(75) Inventors: Brian A. Korgel, Round Rock, TX (US);
Keith P. Johnston, Austin, TX (US);
Katherine Brosh, Austin, TX (US);
Paul Thurk, Austin, TX (US)

(73) Assignee: Merck Patent GmbH, Frankfurter (DE)

( * ) Notice: Subject to any disclaimer, the term of this patent is extended or adjusted under 35 U.S.C. 154(b) by 1421 days.

(21) Appl. No.: 11/122,223

(22) Filed: May 5, 2005

(65) Prior Publication Data

US 2005/0267345 A1    Dec. 1, 2005

Related U.S. Application Data

(63) Continuation-in-part of application No. 10/959,247, filed on Oct. 7, 2004, which is a continuation of application No. 10/109,578, filed on Mar. 28, 2002, now Pat. No. 6,846,565.

(60) Provisional application No. 60/302,594, filed on Jul. 2, 2001.

(51) Int. Cl.
*H01L 29/788* (2006.01)

(52) U.S. Cl.
USPC ........... 257/315; 257/316; 257/321; 436/172; 313/506; 428/403; 428/404; 977/774; 977/810

(58) Field of Classification Search
USPC .................... 257/315–321; 313/506; 436/172
See application file for complete search history.

(56) References Cited

U.S. PATENT DOCUMENTS

| | | | |
|---|---|---|---|
| 4,851,297 A | 7/1989 | Allen et al. |
| 5,260,957 A | 11/1993 | Hakimi et al. |
| 5,420,845 A | 5/1995 | Maeda et al. |
| 5,422,907 A | 6/1995 | Bhargava |
| 5,537,000 A | 7/1996 | Alivisatos et al. |
| 5,576,248 A | 11/1996 | Goldstein |
| 5,585,640 A | 12/1996 | Huston et al. |
| 5,599,403 A | 2/1997 | Kariya et al. |
| 5,783,498 A | 7/1998 | Dotta |

(Continued)

FOREIGN PATENT DOCUMENTS

| WO | WO 97/14176 A1 | 4/1997 |
|---|---|---|
| WO | WO 99/37832 A1 | 7/1999 |

(Continued)

OTHER PUBLICATIONS

Tsutsumi et al., Single electron memory charateristic of silicon nanodot nanowire transistor, Jul. 20, 2000, IEEE Electronics Letters, vol. 36 No. 15, p. 1322-1323.*

(Continued)

*Primary Examiner* — In Suk Bullock
*Assistant Examiner* — Robert Eom
(74) *Attorney, Agent, or Firm* — John A. Fortkort; Fortkort & Houston P.C.

(57) ABSTRACT

A method for the production of a robust, chemically stable, crystalline, passivated nanoparticle and composition containing the same, that emit light with high efficiencies and size-tunable and excitation energy tunable color. The methods include the thermal degradation of a precursor molecule in the presence of a capping agent at high temperature and elevated pressure. A particular composition prepared by the methods is a passivated silicon nanoparticle composition displaying discrete optical transitions.

24 Claims, 32 Drawing Sheets

(56) References Cited

U.S. PATENT DOCUMENTS

| | | | |
|---|---|---|---|
| 5,850,064 | A | 12/1998 | Goldstein |
| 5,852,306 | A | 12/1998 | Forbes |
| 5,852,346 | A | 12/1998 | Komoda et al. |
| 5,935,898 | A | 8/1999 | Trubenbach et al. |
| 5,990,479 | A | 11/1999 | Weiss et al. |
| 6,060,026 | A | 5/2000 | Goldstein |
| 6,060,743 | A | 5/2000 | Sugiyama et al. |
| 6,106,609 | A | 8/2000 | Yang et al. |
| 6,126,740 | A | 10/2000 | Schulz et al. |
| 6,130,007 | A | 10/2000 | Bi et al. |
| 6,159,620 | A * | 12/2000 | Heath et al. .......... 428/615 |
| 6,207,229 | B1 | 3/2001 | Bawendi et al. |
| 6,239,355 | B1 | 5/2001 | Salafsky |
| 6,251,303 | B1 | 6/2001 | Bawendi et al. |
| 6,254,662 | B1 | 7/2001 | Murray et al. |
| 6,262,129 | B1 | 7/2001 | Murray et al. |
| 6,268,041 | B1 | 7/2001 | Goldstein |
| 6,291,258 | B2 | 9/2001 | Kadota |
| 6,300,193 | B1 | 10/2001 | Forbes |
| 6,302,940 | B2 | 10/2001 | Murray et al. |
| 6,306,610 | B1 | 10/2001 | Bawendi et al. |
| 6,306,736 | B1 | 10/2001 | Manna et al. |
| 6,313,015 | B1 | 11/2001 | Lee et al. |
| 6,316,143 | B1 | 11/2001 | Foster et al. |
| 6,319,426 | B1 | 11/2001 | Bawendi et al. |
| 6,322,901 | B1 | 11/2001 | Bawendi et al. |
| 6,326,144 | B1 | 12/2001 | Bawendi et al. |
| 6,331,463 | B1 | 12/2001 | Chen |
| 6,337,762 | B1 | 1/2002 | Ueno |
| 6,339,030 | B1 | 1/2002 | Constant et al. |
| 6,348,295 | B1 | 2/2002 | Griffith et al. |
| 6,361,944 | B1 | 3/2002 | Mirkin et al. |
| 6,423,551 | B1 | 7/2002 | Weiss et al. |
| 6,515,314 | B1 | 2/2003 | Duggal et al. |
| 6,544,870 | B2 | 4/2003 | Park et al. |
| 2001/0002275 | A1 | 5/2001 | Averitt et al. |
| 2001/0040232 | A1 | 11/2001 | Bawendi et al. |
| 2002/0011564 | A1 | 1/2002 | Norris |
| 2003/0066998 | A1 | 4/2003 | Lee |

FOREIGN PATENT DOCUMENTS

| | | |
|---|---|---|
| WO | WO 01/07689 A2 | 2/2001 |
| WO | WO 01/14250 A2 | 3/2001 |
| WO | WO 01/31374 A1 | 5/2001 |
| WO | WO 01/38222 A1 | 5/2001 |

OTHER PUBLICATIONS

Heath et al., Pressure/temperature phase diagrams and superlattices of organically functionalized metal nanocrystal monolayers: the influence of particle size, size distribution, and surface passivant, 1997, American Chemical Society, J. Phys. Chem. B 1997, 101, p. 189-197.*

Gutierrez-Wing et al., On the structure and formation of self-assembled lattices of gold nanoparticles, 1998, Plenum Publishing Corporation, Journal of Cluster Science, vol. 9, No. 4, p. 529-545.*

Batson et al., "Electron Energy Loss Spectroscopy of Single Silicon Nanocrystals: The Conduction Band," Physical Review Letters, vol. 71, No. 6, pp. 911-914 (Aug. 9, 1993).

Bauer et al., "Laser Synthesis of Low-Agglomerated Submicrometer Silicon Nitride Powders from Chlorinated Silanes," J. Am. Ceram. Soc., vol. 74, No. 11, pp. 2759-2768 (1991).

Belomoin et al., "Oxide and Hydrogen Capped Ultrasmall Blue Luminescent Si Nanoparticles," Applied Physics Letters, American Institute of Physics, New York, US, vol. 77, No. 6, pp. 779-781 (Aug. 7, 2000).

Bley et al., "A Low-Temperature Solution Phase Route for the Synthesis of Silicon Nanoclusters," J. Am. Chem. Soc., vol. 118, pp. 12461-12462 (1996).

Bley et al., "Characterization of Silicon Nanoparticles Prepared from Porous Silicon," Chem. Mater., vol. , pp. 1881-1888 (1996).

Chlistunoff et al., "Nitric/Nitrous Acid Equilibria in Supercritical Water," J. Phys. Chem. A, 1999, pp. 1678-1688, vol. 103.

Connolly et al., "Time-Resolved Small-Angle X-ray Scattering Studies of Nanocrystal Superlattice Self-Assembly," J. Am. Chem. Soc., 1998, pp. 2969-2970, vol. 120.

Ding et al., Electrochemistry and Electrogenerated Chemiluminescence from Silicon Nanocrystal Quantum Dots, Science, vol. 296, pp. 1293-1297 (May 17, 2002).

Doty et al., "Temperature-Dependent Electron Transport through Silver Nanocrystal Superlattices," J. Phys. Chem. B., 2001, pp. 8291-8296, vol. 105.

Ehrman et al., "Effect of Temperature and Vapor-phase Encapsulation on Particle Growth and Morphology," J. Mater. Res., vol. 14, No. 4, pp. 1664-1671 (1999).

English et al., "Size tunable Visible Luminescence from Individual Organic Monolayer Stablized Silicon Nanocrystal Quantum Dots," Nano letters, vol. 2, No. 7, pp. 681-685 (2002).

Flagan, "Size Classification of silicon Nanocrystals," Appl. Phys. Lett., vol. 68, No. 22, pp. 3162-3164 (May 27, 1996).

Fojtik et al., "Luminescent Colloidal Silicon Particles," Chemical Physics Letters, vol. 221, pp. 363-367 (Apr. 29, 1994).

Fojtik et al., "Preparation of Colloidal Silicon and Preliminary Photochemical Experiments," Chemical Physics Letters, vol. 134, No. 5, pp. 477-479 (Mar. 13, 1987).

Goldstein, "The Melting of Silicon Nanocrystals: submicron Thin-film Structures Derived from Nanocrystal Precursors," Applied Physics A, vol. 62, pp. 33-37 (1996).

Gray et al., "Microstructure Formation and Kinetics in the Random Sequential Adsorption of Polydisperse Tethered Nanoparticles Modeled as Hard Disks," Langmuir, 2001, pp. 2317-2328, vol. 2001.

Hanrath et al., "Nucleation and Growth of Germanium Nanowires Seeded by Organic Monolayer-Coated Gold Nanocrystals," J. Am. Chem. Soc., 2002, pp. 1424-1429, vol. 124, No. 7.

Heath et al., "A Liquid Solution synthesis of single Crystal Germanium Quantum Wires," Chemical Physics Letters, vol. 208, No. 3,4, pp. 263-268 (Jun. 11, 1993).

Heath et al., "Spatially Confined Chemistry: Fabrication of Ge Quantum Dot Arrays," J. Phys. Chem., vol. 100, pp. 3144-3149 (1996).

Heath, "A Liquid-Solution-Phase Synthesis of Crystalline Silicon," Science, vol. 258, pp. 1131-1133 (Nov. 13, 1992).

Heinrich et al., "Luminescent Colloidal Silicon Suspensions from Porous Silicon," Science, vol. 255, pp. 66-68 (Jan. 3, 1992).

Holmes et al., "Control of Thickness and Orientation of Solution-Grown Silicon Nanowires," Science, vol. 287, pp. 1471-1473 (Feb. 25, 2000).

Holmes et al., "Control of Thickness and Orientation of Solution-Grown Silicon Nanowires," Science, 2000, pp. 1471-1473.

Holmes et al., "Highly Luminescent Silicon Nanocrystals with Discrete Optical Transitions," J. Am. Chem. Soc., vol. 123, pp. 3743-3748 (2001).

Holmes et al., "Highly Luminescent Silicon Nanocrystals with Discrete Optical Transitions," J. Am. Chem. Soc., 2001, pp. 3743-3748, vol. 123.

Holmes et al., "Synthesis of Cadmium Sulfide Q Particles in Water-in-$CO_2$ Microemulsions," Langmuir, 1999, pp. 6613-6615, vol. 15.

Hu et al., "Epitaxial Heterostructures: Side-to-Side Si—ZnS, Si—ZnSe Biaxial Nanowires, and Sandwichlike ZnS—Si—ZnS Triaxial Nanowires," J. Am. Chem. Soc., vol. 125, pp. 11306-11313 (2003).

Kennedy et al., "Cryo-Transmission Electron Microscopy Confirms Controlled Synthesis of Cadmium Sulfide Nanocrystals within Lecithin Vesicles," Chem. Mater., 1998, pp. 2116-2119, vol. 10.

Korgel et al., "'Melting Transition' of a Quantum Dot Solid: Collective Interactions Influence the Thermally-Induced Order-Disorder Transition of a Silver Nanocrystal Superlattice," J. Am. Chem. Soc., 1999, pp. 3533-3534, vol. 121.

Korgel et al., "Assembly and Self-Organization of Silver Nanocrystal Superlattices: Ordered 'Soft Spheres'", J. Phys. Chem. B., 1998, pp. 8379-8388, vol. 102.

Korgel et al., "Condensation of Ordered Nanocrystal Thin Films," Phys. Rev. Lett., 1998, p. 3531, vol. 80.

(56) References Cited

OTHER PUBLICATIONS

Korgel et al., "Controlled Synthesis of Mixed Core and Layered (Zn, Cd)S and (Hg, Cd)S Nanocrystals within Phosphatidylcholine Vesicles," *Langmuir*, 2000, 3588-3594, vol. 16.

Korgel et al., "Quantum Confinement Effects Enable Photocatalyzed Nitrate Reduction at Neutral pH Using CdS nanocrystals," *J. Phys. Chem. B.*, 1997, p. 5010, vol. 101.

Korgel et al., "Synthesis of Size-Monodispers CdS Nanocrystals Using Phosphatidylcholine Vesicles as True Reaction Compartments," *J. Phys. Chem.*, 1996, p. 346, vol. 100.

Littau et al., "A Luminescent Silicon Nanocrystal Colloid via a High-Temperature Aerosol Reaction," J. Phys. Chem., vol. 97, pp. 1224-1230 (1993).

Lu et al., "Growth of Single Crystal Silicon Nanowires in Supercritical Solution from Tethered Gold Particles on a Silicon Substrate," Nano Letters, vol. 3, No. 1, pp. 93-99 (2003).

Park et al., "Band gap engineering of amorphous silicon quantum dots for light-emitting diodes," Applied Physics Letter, vol. 78, No. 17, pp. 2575-2577 (2001).

Pell et al. "Single Particle and Ensemble Spectroscopy of Silicon Nanoparticles," *2001 Materials Research Society Fall Meeting*, Nov. 26, 2001, Boston, Massachusetts, USA.

Pell et al., "The Combined Effect of Quantum Confinement and Surface Chemistry on the Optical Properties of Sterically Stabilized Individual Silicon Nanocrystals and Their Ensembles," *2001 Materials Research Society Fall Meeting* (Abstract), Nov. 26, 2001, Boston Massachusetts, USA.

Saunders et al., "synthesis of Luminescent Silicon Clusters by Spark Ablation," Appl. Phys. Lett., vol. 63, No. 11, pp. 1549-1551 (Sep. 13, 1993).

Shah et al., "Nanocrystal Arrested Precipitation in Supercritical Carbon Dioxide," *J. Phys. Chem. B.*, 2001, pp. 9433-9440, vol. 105.

Shah et al., "Size-Selective Dispersion of Dodecanethiol-Coated Nanocrystals in Liquid and Supercritical Ethane by Density Tuning," *J. Phys. Chem. B.*, 2002, pp. 2545-2551, vol. 106.

Shah et al., "Steric Stabilization of Nanocrystals in Supercritical $CO_2$ Using Flourinated Ligands," J. Am. Chem. Soc., vol. 122, pp. 4245-4246 (2000).

Shah et al., "Sterile Stabilization of Nanocrystals in Supercritical $CO_2$ Using Fluorinated Ligands," *J. Am. Chem. Soc.*, 2000, pp. 4245-4246, vol. 122.

Shkunov et al., "Tunable, Gap-State Lasing in Switchable Directions for Opal Photonic Crystals," *Adv. Funct. Mater.*, pp. 21-26, vol. 12, No. 1.

Stowell et al. "Self-Assembled Honeycomb Networks of Gold Nanocrystals," *Nano Lett.*, 2001, pp. 595-600, vol. 1.

Thimmaiah et al., "A Solvothermal route to Capped Nanoparticles of Gamma-FE2O3 and COFE2O4," Journal of Materials Chemistry, The Royal Society of Chemistry, Cambridge, GB, vol. 11, pp. 3215-3221 (2001).

Wilson et al., "Quantum Confinement in Size-Selected, Surface-Oxidized Silicon Nanocrystals," Science, vol. 262, pp. 1242-1244 (Nov. 19, 1993).

Winter et al., "Recognition Molecule Directed Interfacing Between Semiconductor Quantum Dots and Nerve Cells," *Adv. Mat.*, 2001, pp. 1673-1677, vol. 13.

Wu et al., "A Method for the synthesis of Submicron Particles," Langmuir, vol. 3, pp. 266-271 (1987).

Xiang et al., "Acid-Base Behavior in Supercritical Water," *J. Solution Chem.*, 1997, p. 13, vol. 26.

Xiang et al., "Acid-Base Behavior of Organic Compounds in Supercritical Water," *J. Phys. Chem.*, 1994, pp. 7915-7922, vol. 98.

Ziegler et al., "Optimization models for determining nitric acid equilibria in supercrictical water," *Comput. Chem.*, 1999, pp. 421-434, vol. 23.

Ziegler et al., "Synthesis of Organic Monolayer-Stabilized Copper Nanocrystals in Supercritical Water," *J. Am. Chem. Soc.*, pp. 7797-7803, vol. 123.

Baldwin, Richard K. et al., "Solution reduction synthesis of surface stabilized silicon nanoparticles"; The Royal Society of Chemistry; ChemComm, 2002, pp. 1822-1823.

Mass Spectrometry in Polymer Chemistry, edited by Christopher Barner-Kowollik, Till Gruendling, Jana Falkenhagen, Steffen Weidner; John Wiley & Sons; Jan. 27, 2012; 1 page.

Boughen, L. et al., "Thermal degradation of polyethylene glycol 6000 and its effect on the assay of macroprolactin"; Elsevier; Clin. Biochem; Jun. 2010, vol. 43(9); http://www.ncbi.nlm.nih.gov/pubmed20303933; 1 page.

Chee, Sang-Soo et al., "Reduction Synthesis of Tin Nanoparticles Using Various Precursors and Melting Behavior"; Department of Materials Science & Engineering; Seoul National University of Science and Technology; Seoul, Korea; 23 pages.

Gerion, Daniele et al., "Solution Synthesis of Germanium Nanocrystals: Success and Open Challenges"; Nano Letters, 2004, vol. 4, No. 4; pp. 597-602.

Holmes, Justin D. et al.; "Highly Luminescent Silicon Nanocrystals with Discrete Optical Transitions"; Journal of American Chemical Society; 2001; pp. 3743-3748.

Kapetanakis, E. et al., "Nanocrystal Memories"; Encyclopedia of Nanoscience and Nanotechnology; vol. 6, 2004; pp. 321-340.

Liong, W.L. et al., "Effect of Concentration of Sodium Borohydrate on the Synthesis of Silicon Nanoparticles via Microemulsion Route"; World Academy of Science, Engineering and Technology; 2009; 4 pages.

Rossiter, Walter J. et al., "An investigation of the degradation of aqueous ethylene glycol and propylene glycol solutions using ion chromatography"; Solar Energy Materials, vol. 11, 1985; North-Holland Amsterdam; 4 pages.

Swihart, Mark T., "Vapor-phase synthesis of nanoparticles"; Current Opinion in Colloid and Interface Science, vol. 8, 2003, pp. 127-133.

Wu, Jian et al., Thermal degradation studies of poly(ethylene glycol); The Dow Chemical Company; Core R&D, Analytical Sciences, white paper; 1 page.

\* cited by examiner

| Emission Wavelength (nm) | $\tau_1$ (ns) | $A_1$ (%) | $\tau_2$ (ns) | $A_2$ (%) | $\tau_3$ (ns) | $A_3$ (%) |
|---|---|---|---|---|---|---|
| 520 | 0.27 | 31 | 2.2 | 46 | 5.7 | 23 |
| 560 | 0.33 | 29 | 2.3 | 46 | 6.0 | 25 |
| 600 | 0.37 | 27 | 2.3 | 47 | 6.2 | 26 |
| 640 | 0.39 | 28 | 2.3 | 47 | 6.4 | 25 |
| 680 | 0.42 | 30 | 2.2 | 46 | 6.3 | 24 |

Fig. 30

APPLICATIONS OF LIGHT-EMITTING NANOPARTICLES

PRIORITY CLAIM

This application claims priority to Provisional Patent Application No. 60/302,594 entitled "Light-Emitting Nanocrystals" filed on Jul. 2, 2001.

STATEMENT REGARDING FEDERALLY SPONSORED RESEARCH

The United States Government has rights in this invention pursuant to National Science Foundation Contract No. 26-1122-20XX.

BACKGROUND OF THE INVENTION

1. Field of the Invention

The present invention relates to the field of nanotechnology. In particular, to compositions and methods of making Group IV metal nanoparticles and their applications.

2. Description of the Relevant Art

The term "nanoparticle" generally refers to particles that have an average diameter between about 1 nm to 100 nm. Nanoparticles have an intermediate size between individual atoms and macroscopic bulk solids. Nanoparticles typically have a size on the order of the Bohr exciton radius, or the de Broglie wavelength, of the material, which allows individual nanoparticles to trap individual or discrete numbers of charge carriers, either electrons or holes, or excitons, within the particle. The spatial confinement of electrons (or holes) by nanoparticles is believed to alter the physical, optical, electronic, catalytic, optoelectronic and magnetic properties of the material. The alteration of the physical properties of a nanoparticle due to confinement of electrons is generally referred to as quantum confinement effects.

Nanoparticles may exhibit a number of unique electronic, magnetic, catalytic, physical, optoelectronic and optical properties due to quantum confinement effects. For example, many nanoparticles exhibit photoluminescence effects that are significantly greater than the photoluminescence effects of macroscopic molecules having the same composition. Additionally, these quantum confinement effects may vary as the size of the nanoparticle is varied. For example, size-dependent discrete optical and electronic transitions exist for clusters of Group II-VI semiconductors (e.g., CdSe) or Group III-V semiconductors (e.g., InAs).

This loss of energy level degeneracy, however, has not previously been observed in the optical properties of Group IV nanoparticles (e.g., silicon (Si) nanocrystals). In Si, for example, the lowest lying energetic transition violates conservation of momentum; therefore, light absorption requires phonon assistance (a phonon is a quanta of vibrational energy), resulting in a very low transition probability. Consequently, bulk Si photoluminescence is very weak. Quantum confinement in Si nanocrystals and porous Si, however, leads to enhanced luminescence efficiencies with quantum yields that have reached as high as 5% at room temperature and blue-shifted "band gap" energies. However, in sharp contrast to their direct band gap semiconductor counterparts, Si nanocrystals have not displayed discrete electronic transitions in the absorbance and photoluminescence excitation (PLE) spectra.

The wet chemical techniques used to synthesize Group II-VI and III-V semiconductors have not been readily applied to Group IV materials, largely due to the high temperatures required to degrade the necessary precursors. Typically the temperature required to degrade the necessary Group IV precursors exceeds the boiling points of typical solvents. Furthermore, the strong covalent bonding of Si requires temperatures higher than the Group II-VI materials to achieve highly crystalline cores. Moderate progress has been made with alternative solution-phase reduction of Si salts and aerosol methods. These methods, however, have produced nanocrystals with extremely broad size distributions. Aerosol methods have required a thick oxide coating to stabilize their structure, which has been shown recently to significantly affect the photoluminescence (PL) energies of porous Si.

SUMMARY OF THE INVENTION

In an embodiment Group IV metals form nanocrystalline or amorphous particles by the thermal degradation of a precursor molecule in the presence of molecules that bind to the particle surface, referred to as a capping agent at high temperature and elevated pressure. In certain embodiments, the reaction may run under an inert atmosphere. In certain embodiments the reaction may be run at ambient pressures. The particles may be robust, chemically stable, crystalline, or amorphous and organic-monolayer passivated, or chemically coated by a mixture of organic molecules. In one embodiment, the particles emit light in the ultraviolet wavelengths. In another embodiment, the particles emit light in the visible wavelengths. In other emobodiments, the particles emit light in the near-infrared and the infrared wavelengths. The particles may emit light with high efficiencies. Color of the light emitted by the particles may be size-tunable and excitation energy tunable. The light emission may be tuned by particle size, with smaller particles emitting higher energy than larger particles. The surface chemistry may also be modified to tune the optical properties of the particles. In one embodiment, the surfaces may be well-passivated for light emission at higher energies than particles with surfaces that are not well-passivated. The average diameter of the particles may be between 1 and 10 nm. A particular composition prepared by the methods is a passivated silicon nanoparticle composition displaying discrete optical transitions and photoluminescence.

In an embodiment, a solvent may be used to assist in solvating the precursors and capping agents. The solvent may be substance capable of dissolving the precursor and capping agents. The capping agent may act as the solvent.

In certain embodiments, the nanoparticles may include capping agents. The capping agents may include an end bound to the surface of the particle. Capping agents may assist in protecting the particle from oxidation and/or water. Capping agents may assist in solubilizing, or dispersing, the particles. In one embodiment, polar capping agents might be used to disperse particles in aqueous media. In another embodiment, organic, largely hydrocarbon, capping agents might be used to disperse particles in organic solvents. In another embodiment, a mixture of polar and organic capping agents may be used to disperse the particles in a polar organic solvent. In another embodiment, fluorinated capping agents may be used to disperse the particles in carbon dioxide, or other fluorocarbon solvents. Capping agents may assist in controlling the formation of the particles during the reaction, by decreasing aggregation of the particles as the particles form.

In some embodiments, a flow through processor may be used to form the nanoparticles. The processor may allow for the continuous production of particles on a large scale.

In certain embodiments, the nanoparticles formed by the method described herein may be used in a variety of applications. Several examples of possible applications are described herein and include: lights; light emitting diodes; flat panel displays; biological assays; biological sensors; memory devices; and transistors. The methods described herein may create Group IV particles with novel properties.

In an embodiment, a method of forming nanoparticles may include heating a mixture of a Group IV metal organometallic precursor and a capping agent at a temperature where the precursor decomposes forming the nanoparticles.

In some embodiments, it should be understood that heating the mixture in order to decompose the precursors to form nanoparticles may include heating at a temperature at or below the supercritical temperature of the capping agent or a solvent (in embodiments where the capping agent does not act as the solvent).

In certain embodiments, it should be understood that heating the mixture in order decompose the precursors to form nanoparticles may include heating at a temperature above about 300° C. and below the supercritical temperature of the capping agent or a solvent (in embodiments where the capping agent does not act as the solvent).

In other embodiments, it should be understood that heating the mixture in order to decompose the precursors to form nanoparticles may include heating at a temperature below the supercritical temperature of the capping agent or a solvent (in embodiments where the capping agent does not act as the solvent). The temperature may be not less than about 100° C. below the supercritical temperature of the fluid capping agent or a solvent (in embodiments where the capping agent does not act as the solvent).

In an embodiment, a nanoparticle may be formed by a method including heating a mixture of a Group IV organometallic precursor and a capping agent. Heating the mixture may include heating the mixture at a temperature where the precursor decomposes forming the nanoparticle.

Certain embodiments may include a nanoparticle including a Group IV metal and a capping agent coupled to the Group IV metal. The nanoparticle may have an average particle diameter of between about 1 to about 100 angstroms. The capping agent may inhibit oxidation of the nanoparticle.

An embodiment may include a method of forming nanoparticles including heating a mixture of one or more organometallic precursors and a capping agent in a supercritical fluid. The method may include decomposing the organometallic precursors, forming the nanoparticles.

In some embodiments, a nanoparticle may be formed by a method comprising heating a mixture of one or more organometallic precursors and a capping agent in a supercritical fluid. The method may include decomposing the organometallic precursors, forming the nanoparticles.

In an embodiment, a nanoparticle may include a metal and a capping agent coupled to the metal. The nanoparticle may have an average particle diameter of between about 1 to about 100 angstroms. The capping agent may inhibit oxidation of the nanoparticle.

Certain embodiments may include a method of forming nanoparticles including heating a mixture of one or more metal salts and a capping agent in supercritical water. The metal salts may decompose, forming the nanoparticles.

In other embodiments, a nanoparticle may be formed by the method comprising heating a mixture of one or more metal salts and a capping agent in supercritical water. The metal salts may decompose, forming the nanoparticles.

In an embodiment, a nanoparticle may include a metal oxide and a capping agent coupled to the metal oxide. The nanoparticle may have an average particle diameter of between about 1 to about 100 angstroms. The capping agent may inhibit oxidation of the nanoparticle.

An embodiment of a method of forming nanoparticles in a continuous manner may include injecting a mixture of an organometallic precursor and a capping agent into a reactor. The method may include heating the mixture within the reactor to a temperature wherein the precursor decomposes forming the nanoparticles. In addition the method may include removing the formed nanoparticles from the reactor while substantially simultaneously injecting additional organometallic precursors and capping agents into the reactor.

In certain embodiments, a nanoparticle may be formed by a method including heating a mixture of one or more organometallic precursors and a capping agent in a fluid at a temperature above about 300° C. and below the supercritical temperature of the fluid.

In other embodiements, a nanoparticle may be formed by a method comprising heating a mixture of one or more organometallic precursors and a capping agent in a fluid at a temperature below the supercritical temperature of the fluid. The temperature of the fluid may be not less than about 100° C. below the supercritical temperature of the fluid.

An embodiment of a light emitting device may include a plurality of nanoparticles. The nanoparticles may include a Group IV metal and a capping agent coupled to the Group IV metal. The nanoparticles may have an average particle diameter of between about 1 to about 100 angstroms. The light emitting device may include an anode electrically coupled to the plurality of nanoparticles. The light emitting device may include a cathode electrically coupled to the plurality of nanoparticles. The anode and the cathode together may be configured to conduct an applied current to the nanoparticles. The nanoparticles may produce light in response to the applied current.

An embodiment of a light emitting device may include a plurality of nanoparticles. The nanoparticles may be formed by a method including heating a mixture of a Group IV organometallic precursor and a capping agent at a temperature. Heating the mixture may decompose the precursor forming the nanoparticles. The light emitting device may include an anode electrically coupled to the plurality of nanoparticles. The light emitting device may include a cathode electrically coupled to the plurality of nanoparticles. The anode and the cathode together may be configured to conduct an applied current to the nanoparticles. The nanoparticles may produce light in response to the applied current.

Certain embodiments of a display apparatus may include a support and a plurality of light emitting devices positioned on the support. The light emitting devices may include a plurality of nanoparticles. The nanoparticles may include a Group IV metal and a capping agent coupled to the Group IV metal. The nanoparticle may have an average particle diameter of between about 1 to about 100 angstroms. The light emitting devices may include a conductive material electrically coupled to the plurality of nanoparticles. The conductive material may function to conduct an applied current to the particles. The display apparatus may include a controller functioning to control the application of current to each of the lights.

An embodiment of a system for detecting an analyte in a fluid may include a nanoparticle. The nanoparticle may include a Group IV metal and a capping agent coupled to the Group IV metal. The metal nanoparticle may have an average particle diameter of between about 1 to about 100 angstroms. The system may include a receptor which functions to interact with the analyte. The receptor may be coupled to the nanoparticle.

An embodiment of a system for detecting an analyte in a fluid may include a nanoparticle. The nanoparticle may be formed by a method comprising heating a mixture of a Group IV organometallic precursor and a capping agent. Heating the mixture may include heating the mixture at a temperature where the precursor decomposes forming the nanoparticle. The system may include a receptor which functions to interact with the analyte. The receptor may be coupled to the nanoparticle.

An embodiment of a memory device which may include a source functioning to apply an electrical charge. The memory device may include a drain functioning to hold an electric charge. The memory device may include a channel functioning to separate the source and the drain. The memory device may include a floating gate positioned above the channel. The floating gate may include a plurality of nanoparticles. Where at least a plurality of the nanoparticles may include a Group IV metal and a capping agent coupled to the Group IV metal. At least one of the nanoparticles may have an average particle diameter of between about 1 to about 100 angstroms. The memory device may include a control gate positioned substantially adjacent the floating gate. The memory device may include and a conductor comprising an oxide positioned between the control gate and the floating gate. The floating gate may be positioned between the channel and the control gate.

In an embodiment, a coherent light emitting device may include a plurality of nanoparticles. The nanoparticle may be formed by a method including heating a mixture of a Group IV organometallic precursor and a capping agent at a temperature wherein the precursor decomposes, and the nanoparticle is formed. The nanoparticles may include a metal and a capping agent coupled to the metal. At least one of the nanoparticles may have an average particle diameter of between about 1 to about 100 angstroms. The coherent light emitting device may include an excitation source functioning to apply energy to the nanoparticles in an absorbable form. The coherent light emitting device may include an optical cavity functioning to direct light. When the excitation source applies energy to nanoparticles the nanoparticles may produce light. Light produced by the nanoparticles may be directed by the optical cavity.

In an embodiment, a system for at least partially containing an electrical charge temporarily may include a cathode comprising a plurality of nanoparticles. The nanoparticle may be formed by a method including heating a mixture of a Group IV organometallic precursor and a capping agent at a temperature wherein the precursor decomposes, and the nanoparticle is formed. The nanoparticles may include a metal and a capping agent coupled to the metal. The metal may be a Group IV metal. At least one of the nanoparticles may have an average particle diameter of between about 1 to about 100 angstroms. The nanoparticles may be electroactive. The system may include an anode. The anode may include an electroactive material. The system may include a separator positioned between the cathode and the anode functioning to inhibit contact between a portion of the cathode and a portion of the anode.

In an embodiment, a system for electrically communicating with a biological entity may include a nanoparticle. The nanoparticle may be formed by a method including heating a mixture of a Group IV organometallic precursor and a capping agent at a temperature wherein the precursor decomposes, and the nanoparticle is formed. The nanoparticle may include a metal and a capping agent coupled to the metal. The metal may be a Group IV metal. At least one of the nanoparticles may have an average particle diameter of between about 1 to about 100 angstroms. At least one of the nanoparticles may produce an electric field in response to a stimulus. The system may include a receptor functioning to interact with the biological entity. The receptor may be coupled to the nanoparticle.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings.

FIG. 30 depicts a table of fluorescence lifetime measurements on Si nanoparticle dispersions. The fluorescence decay curves were fit with three exponential functions.

DETAILED DESCRIPTION

Figure 1:
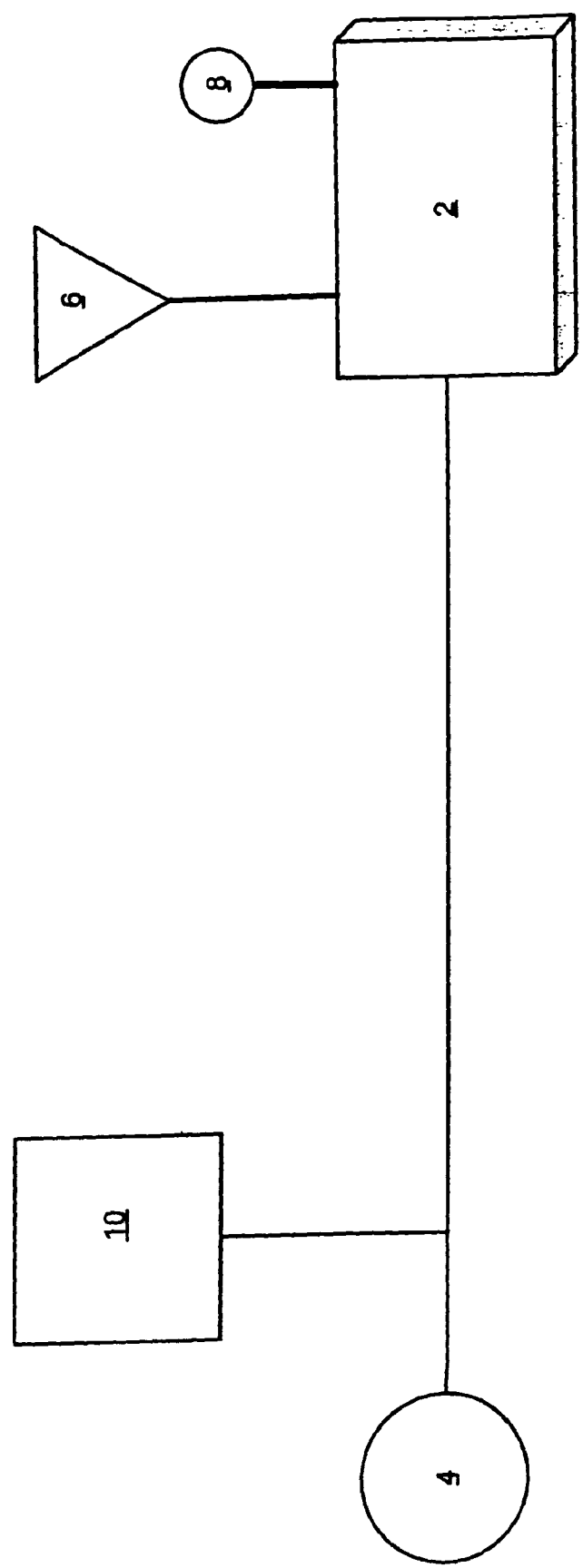
FIG. 1 depicts a schematic flow chart of an embodiment of a batch reaction method.

Nanoparticles may be prepared by using the methods described herein. In one embodiment, nanoparticles may be formed by reacting an organometallic precursor in the presence of a capping agent The organometallic precursor and capping agent may be heated at a pressure greater than 1 atm. in a reaction vessel. The reaction vessel may be made of type II titanium, or other titanium, stainless steel, or any other material rated for high temperatures and high pressures. Heating of the organometallic precursor results in the thermal degradation of the organometallic precursor, which in turn leads to the formation of nanoparticles. The precursor may degrade through a free radical mechanism, or it may degrade through thermolysis. The dimensions of the nanoparticles may be controlled by reaction conditions and the capping agent used. The reaction conditions used to control the particle size may include, for example, the temperature, pressure, precursor concentration, capping ligand concentration, solvent, precursor composition and capping agent composition. In one embodiment a free radical initiator may be added to the reaction. The nanoparticle may be controlled structure with a capping ligand or passivating ligand. It is believed that the capping agent may aid in controlling the dimensions of the formed nanoparticles by inhibiting growth of the nanoparticles. The capping agent may also prevent reactive degradation of the nanoparticles when exposed to water and oxygen and other chemical contamination.

Under the reaction conditions of high temperature and pressure, the size of nanoparticles may be controlled by altering the pressure, temperature, amount of precursor, amount of capping agent or by altering a combination of conditions and reagents to produce a narrow distribution of nanoparticle size ranges. In some embodiments, conditions may be controlled for the express purpose of producing a wide distribution of nanoparticle size ranges. It should be appreciated that the methods and compositions described can be modified to accommodate the construction of nanoparticles from a variety of thermally degradable precursors by modifying the reaction vessel, addition of a solvent, altering the capping agent, and/or reagents, or through the sequential addition of reactants after initial particle nucleation.

The organometallic precursor may be a Group IV metal that includes organic groups. As used herein a "Group IV metal" includes the elements of silicon, germanium, and tin. Generally, organometallic Group IV precursors are compounds that may be thermally degraded to form nanoparticles that are composed primarily of the Group IV metal. In some embodiments, the nanoparticle contains a mixture of Group IV elements, such as $Si_xGe_{1-x}$, $Si_xSn_{1-x}$, or $Ge_xSn_{1-x}$. Organometallic Group IV precursors include, but are not limited to organosilicon, organogermanium and organotin compounds. Some examples of Group IV precursors include, but are not limited to, alkylgermaniums, alkylsilanes, alkylstannanes, chlorosilanes, chlorogermaniums, chlorostannanes, aromaticsilanes, and aromatic germaniums and aromaticstannanes. Particular examples of organometallic silicon precursors include, but are not limited to, tetraethyl silane or diphenylsilane. Particular examples of organometallic germanium precursors include, but are not limited to, tetraethylgermane or diphenylgermane.

The capping agent may interact with an organometallic precursor during formation of the nanoparticle to assist in controlling the growth of the particle. The capping agent may bond covalently to the particle surface, or stick through weak interactions, such as hydrogen bonding. The capping agents may physisorb to the particle surface. In one embodiment, capping of the particle surfaces may occur through a combination of organic ligands and inorganic small molecules. Oxygen or sulfur may also bond to the surface in some instances. Additionally, the capping agent may assist in solubilizing the organomettalic precursor. Additionally, two or more kinds of capping agents might be added to the reaction mixture. In one embodiment, a mixture of organometallic precursors may be added to the reactor for particle formation.

Capping agents include compounds having the general formula $(R)_n$—X, where X is an atom or functional group capable of binding to the surface of the nanoparticles. The term "binding" refers to an interaction that associates the capping agent with the nanoparticles. Such interactions may include ionic, covalent, dipolar, dative, quadrupolar or van der Walls interactions. Each R group is independently hydrogen, an aryl group having between 1 and 20 carbon atoms or an alkyl group having between 1 and 20 carbon atoms. X may be an atom that includes, but is not limited to, nitrogen, carbon, oxygen, sulfur, and phosphorus. Alternatively, X may be a functional groups that includes, but is not limited to, a carboxylate, a sulfonate, an amide, an alkene, an amine, an alcohol, a hydroxyl, a thioether, a phosphate, an alkyne, an ether, or a quaternary ammonium group. Examples of capping agents include, but are not limited to, alcohols, alkenes, alkynes, thiols, ethers, thioethers, phosphines, amines, amides, carboxylates, sulfonates, or quaternary ammonium compounds.

In some embodiments, the capping agent may be an alcohol. Alcohols that may be used include n-alcohols having between 1 to 20 carbon atoms. An example of such an n-alcohol is 1-octanol. In other embodiments, the capping agent may be an alkene. Alkenes that may be used include alpha-olefins having between 1 to 20 carbon atoms, or olefins with unsaturated chains. An example of such an alkene is 1-octene. In another embodiment the capping agent may be a thiol. Thiols that may be used include 1-thiols having between 1 to 20 carbon atoms. An example of such a thiol is 1-thiooctanol.

The reaction of the organometallic precursor and the capping agents is conducted at temperature above room temperature (e.g., above about 25° C.), and at pressures above atmospheric pressure (e.g., above about 1 atm.). The temperature chosen for the reaction is such that the organometallic precursor will be thermally decomposed to produce the nanoparticles. In some embodiments, a reducing agent, such as sodium borohydride, or lithium borohydride, or hydrogen, might be added to aid nanoparticle formation. In some embodiments, the reaction may be conducted in a pressurized reaction vessel at a temperature above the boiling point of the organometallic precursor, the capping agent, or both the organometallic precursor and the capping agent. Thus, a reaction may be at a temperature above the boiling point of one or more of the reactants and be pressurized such that the solvent is kept in a liquid or diffusible state. The reaction mixture may be heated and pressurized above the critical point of the mixture, or it may be below the critical point of the mixture, either as a superheated liquid, or in the gas-liquid two-phase region of the phase diagram. The pressure under which a reaction is performed may be high enough to raise the boiling point of a solvent but still be below the critical pressure of a solvent. The temperature and pressure may be such that the precursor and capping ligands will be diffusible in the solvent In other embodiments, the reaction may be conducted in a super critical fluid. A supercritical fluid is obtained by heating a fluid above the critical temperature and at a pressure above the critical pressure for the fluid. The critical temperature and critical pressure for a fluid is known as the critical point. Above the critical point neither a liquid nor gas state exist. Instead a phase known as a supercritical fluid exists. For example, a gas enters the supercritical state when the combination of pressure and temperature of the environment in which the gas is contained is above a critical state. The critical temperature of octanol is 385° C. The critical pressure of octanol is 34.5 bar. When octanol is subjected to temperatures and pressures above 385° C. and 34.5 bar, the octanol exists in a supercritical state. The critical temperature and pressure of other components may be readily calculated or experimentally determined. The particle size may be controlled by varying the pressure of the reaction mixture under isothermal conditions above or below the critical point of the mixture. The particle size may be controlled by varying the temperature of the reaction mixture under isobaric reaction conditions above or below the critical point of the mixture.

A compound or element above the critical temperature and critical pressure is referred to as a supercritical fluid. Supercritical fluids may have high solvating capabilities that are typically associated with compositions in the liquid state. Supercritical fluids also have a low viscosity that is characteristic of compositions in the gaseous state. Additionally, a supercritical fluid maintains a liquid's ability to dissolve substances.

Many organometallic Group IV metal precursors require high temperatures (above about 300° C.) to induce the decomposition into nanoparticles. The high temperatures needed to decompose the organometallic precursors typically exceed the boiling points of the capping agent, the solvent, and the precursor itself. The use of elevated pressure or super critical conditions allows the decomposition of organometallic precursors to form nanoparticles using the capping agents described above. In one embodiment, the high temperatures are necessary to drive the reaction between the nanoparticle surface and the capping agents. In another embodiment, the capping agent may react spontaneously upon nanoparticle formation.

In some embodiments, the reaction may be conducted at a temperature and pressure that is above the critical point of the capping agent. The capping agent may, therefore, become a supercritical fluid. This allows the reaction to be conducted at a temperature that induces decomposition of the organometallic precursor and reaction of the capping agent with the forming nanoparticle. Additionally, the supercritical fluid may promote rapid reactant diffusion. Rapid diffusion of the reactants may allow diffusion-limited growth which may lead to narrow particle size distributions. Particles may also grow through a coagulative growth process to yield stable redispersible nanoparticles.

In another embodiment, the decomposition of the organometallic precursor may be conducted in the presence of a capping agent and a substantially inert solvent. Generally, a solvent will dissolve both precursor molecules and capping agents. Examples of solvents that may be used include, but are not limited to, hydrocarbons, alcohols, ketones, ethers and polar aprotic solvents (e.g., dimethyl formamide, dimethyl sulfoxide, etc). Hydrocarbon solvents include, but are not limited to aromatic and non-aromatic hydrocarbon carbons. Examples of aromatic hydrocarbon solvents include, but are not limited to benzene, toluene, and xylenes. Examples of non-aromatic hydrocarbon solvents include cyclic hydrocarbons (e.g., cyclohexane, cyclopentane, etc.) and aliphatic hydrocarbons (e.g., hexane, heptane, octane, etc.). In certain embodiments the reaction may be performed at conditions, such as temperature and pressure, which are below the critical point of solvent, but above the boiling point of the solvent. Thus, a reaction may be at a temperature above its ambient boiling point and be pressurized such that the boiling point is elevated above the temperature of the reaction conditions, thus maintaining the solvent in a liquid or diffusible state. The pressure under which a reaction is performed may be high enough to raise the boiling point of a solvent but still be below the critical pressure of a solvent. The temperature and pressure may be such that the precursor and capping ligands will be diffusible in the solvent In other embodiments the solvent may be at supercritical conditions. The temperature and pressure may be such that the precursor and capping agents will be diffusible in the solvent. Thus, reaction condition may be above and below the critical point of a solvent.

The temperatures at which the reactions are carried out are sufficient for the thermal degradation of the precursor molecules. The temperature of the reaction will vary with the characteristics of the precursor molecules. In certain embodiments the temperature may be in the approximate range of 300° C. to 800° C., in some embodiments 400° C. to 700° C. and the temperature can be approximately 450° C. to 550° C. In an embodiment the reaction may be approximately 500° C.

The pressure at which the reaction is carried out should be sufficient to maintain at least a portion of the precursor and at least a portion of the capping ligand in a diffusible state and/or a solvent in a dense liquid or gaseous state with a solvent density above 0.1 g/mL. In certain embodiments the reaction conditions may be beyond the critical point of a solvent and/or capping agent. For example, it is envisioned that supercritical octanol can be used as a capping agent. In certain embodiments pressures of approximately 2 to 500 bar may be used. In other embodiments the approximate range of pressure may be 25 to 400 bar. In certain embodiments approximately 50-350 bar is preferred.

When a solvent is used the organometallic precursor may be present in the initial reaction solution at various concentrations ranging from nanomolar to micromolar to molar concentrations. In certain embodiments a precursor may be present in the approximate range of 10 mM to 5 M, 125 to 625 mM, 250 to 500 mM, 300 to 500 mM, or 400 mM to 1 M. Additionally, the mole ratio of capping agent to the organometallic precursor may be in the approximate range of 1,000,000:1 to 1:1,000 when a solvent is used. In other embodiments the ratio may be in the approximate range of 10,000:1 to 1:10,000. In other embodiments the mole ratio of reagents may be in an approximate range from 1 to 1,000,000 parts capping agent to 1 to 10 parts precursor molecule, or in the approximate range of 500 to 50,000 parts capping agent to 1 to 10 parts precursor molecule, or in the approximate range of 800 to 10,000 parts capping agent to 1 to 10 parts precursor molecule.

Nanoparticles may be produced using a batch process, a semibatch process or a continuous flow process. FIG. 1 illustrates an embodiment of an apparatus for producing nanoparticles using a batch process. Reaction vessel 2 may be in fluid communication with high-pressure pump 4. Reaction vessel 2 may be a stainless steel cell (High Pressure Equip. Co., Buffalo, N.Y.), or an inconnel high pressure cell, or a titanium cell. Alternative high-pressure vessels may be used to carry out the methods of the invention. Alternatives include, but are not limited to, iron based alloys and titanium alloys. Reaction vessel 2 may be operatively coupled to thermal source 6 and thermometer 8. Reagents are pumped into reaction vessel 2 from a reagent reservoir 10. Reagent reservoir 10 may include the solvent, precursor, and capping agent. Once the reagents are pumped into reaction vessel 2 reaction vessel 2 may be pressurized and heated to the appropriate temperature and pressure. After allowing sufficient time for the thermal degradation of a precursor molecule and the subsequent formation of nanoparticles the reaction may be cooled and brought to ambient pressures. The reaction may occur in a matter of seconds, or in some embodiments, the reaction occurs in a matter of several hours. The reaction time, or the residence time in the reactor may dictate the particle size, with longer residence times leading to larger particle sizes. The product is removed from the vessel 2 for further processing. The product may then be sprayed, purified, extracted, and/or size fractionated.

Products may be isolated and dried to remove the solvents and/or volatile reaction products. The dried products may then be redispersed in an appropriate solvent, such as chloroform or hexane. Alternative solvents for redispersion include but are not limited to hydrocarbons, ethers, alcohols, ketones, and compressed fluids such as ethane, propane or carbon dioxide. In particular embodiments the capping agents may be tailored for redispersion in water, carbon dioxide, fluorocarbons, and other organic and polar solvents.

After the reaction is at least partially completed, the reaction vessel may include a mixture of nanoparticles and unreacted organometallic precursors. If no solvent is used, the nanoparticles may be dissolved or suspended in the capping agent If a solvent is used, the nanoparticles may be dissolved or suspended in the solvent. The size distribution of the nanoparticles is typically determined by the reaction conditions and reagents. To narrow the size distribution of particles various separation techniques may be used. The nanoparticles may be separated from the unreacted reagents by a variety of techniques.

In an embodiment, the nanoparticles may be isolated from the reaction compartment by flushing with a solvent. The solvent may be an organic solvent, or a polar solvent, depending on the nanoparticle solubility. The reactor may be flushed once, or several times, to remove the nanoparticle. Because nanoparticles have an average diameter of less than about 100 nm, the addition of a solvent causes the particles to become "dispersed" within the solvent. When dispersed in a solvent, the nanoparticles may exist as individual particles that are separated form other nanoparticles by the solvent. Particles may be removed from the solvent by treating with a second solvent. The second solvent may induce aggregation of the nanoparticles. Aggregation of the nanoparticle may cause particles to associate with each other to form aggregates of particles. These aggregates may be filtered to remove the solvent and other impurities in the reaction mixture.

During formation of nanoparticles, a nanoparticles having a large average particle size distribution may be obtained. In some embodiments, the size distribution of particles may be narrowed by the choice of solvents used for the isolation process. As described above, nanoparticles may be dispersed in a solvent. The addition of a second solvent may induce aggregation of the nanoparticles. In some embodiments, the second solvent may induce only a portion of the nanoparticle having a narrow particle size distribution to be isolated. For example, if the nanoparticles formed after reaction of the organometallic precursor have a average particle size ranging from 1 to about 100 nm, the addition of a second solvent may induce aggregation of only nanoparticles in the 2540 nm range. In this example, nanoparticles having an average particle size greater than 40 nm or less than 25 nm do not aggregate and remain dispersed in the solvents. The aggregated particles may be removed by filtration. By varying the solvent used, the size of the nanoparticles that aggregate may be altered allowing easy isolation of nanoparticles having a specific particle size distribution. Aggregated nanoparticles may be collected through centrifugation, filtering, or other means of collecting a solid from a slurry. Selective extraction may be carried out using polar/nonpolar miscible solvent pairs, including, but not limited to, chloroform/ethanol, or hexane/ethanol, or water/ethanol.

In other embodiments chromatography may be used to size fractionate nanoparticles of the present invention. Chromatography methods may be used to separate nanoparticles based on size, shape, charge, hydrophobicity, or other characteristics that distinguish the nanoparticles. In some embodiments liquid chromatography may be used. The liquid chromatography may be conducted at ambient pressures or at high pressures using high pressure liquid chromatography (HPLC). The column may be packed with size exclusion gel that separates small unreacted byproducts from the larger particles. In other embodiments, the column may consist of, but is not limited to, an ion exchange resin, a reverse chromatography packing, or silica. Any suitable size-exclusion or reverse-phase chromatographic packing may be used for the separation. In one embodiment, Bio-Beads™, (Bio-Rad, Hercules, Calif.) may be used.

Figure 3:
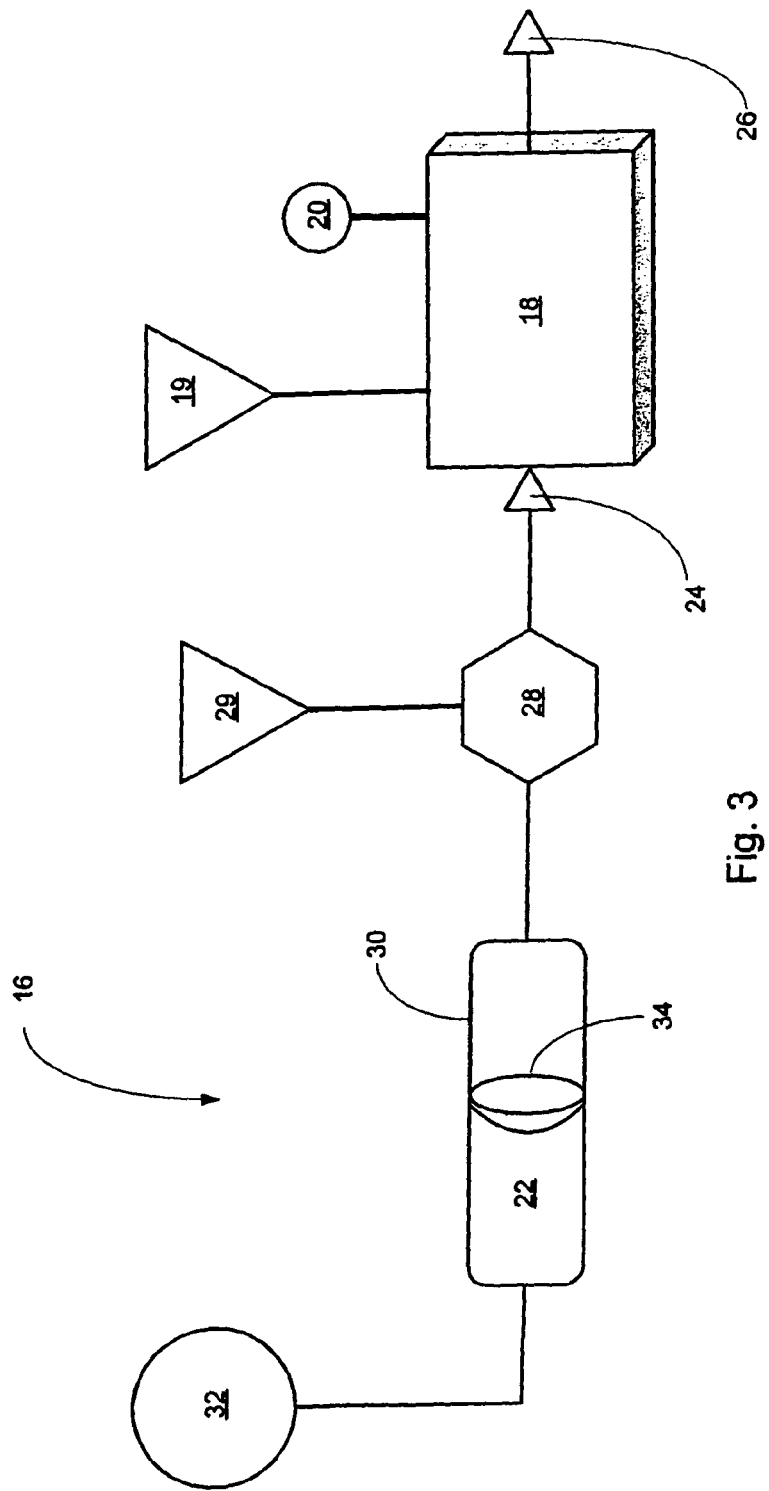
FIG. 3 depicts a schematic of an embodiment of a continuous flow production system.

In another embodiment, a flow process may be used for the manufacture of nanoparticles. A flow process offers a way to produce nanoparticles continuously. FIG. 3 depicts a schematic of an embodiment of a continuous flow production system. In an embodiment, continuous flow system 16 may include reactor 18, a first heater 19 coupled to reactor 18, a temperature monitor 20 coupled to reactor 18, and injector 22 coupled to reactor 18. Reactor 18 may include inlet 24 and outlet 26. First heater 19 may function to control the temperature of the reactor during use. Temperature monitor 20 may function to monitor the reaction temperature during use. Injector 22 may function to inject the reagents into the reactor 18 at pressure greater than 1 atm.

In certain embodiments, reactor 18 may be a high-pressure reaction vessel. Certain embodiments use a stainless steel cell (High Pressure Equip. Co., Buffalo, N.Y.), or an inconnel high pressure cell. Alternative high-pressure vessels may be used to carry out the methods of the invention. Alternatives include, but are not limited to, iron based alloys and titanium. First heater 19 may be used to control the temperature of reactor 18. In one embodiment, a first heater may be a heating tape. Other types of heaters include, but are not limited to heating mantles, oil baths, metal baths, resistive heaters, and hot air heaters.

In an embodiment, reactor 18 may be of a length such that precursors decompose to form nanoparticles during the time the precursors are in reactor 18. The flow rate of the precursors and capping agents may be adjusted to ensure the reaction runs to completion.

Temperature monitor 20 may be coupled to reactor 18 and include a device for observing the temperature of the reaction within reactor 18. The temperature monitor should also be capable of withstanding the potentially harsh conditions therein. A non-limiting example of a temperature monitor is a platinum resistance thermometer.

In an embodiment, continuous flow system 16 may also include mixing chamber 28. Mixing chamber 28 may be coupled to inlet 24 and may include second heater 29 functioning to preheat precursor, capping agent, and solvent before injecting the mixture into reactor 18. Injector 22 may be coupled to mixing chamber 28 and function to inject the solvent into mixing chamber 28 at the appropriate pressure. Mixing chamber 28 may include a second heater which may function to control the temperature of mixing chamber 28. One skilled in the art may envision numerous means of controlling the temperature of mixing chamber 28 known to the art.

Continuous flow system 16 may include injector 22. In some embodiments, injector 22 may be coupled to reactor 18, in other embodiments injector 22 may be coupled to mixing chamber 28, or in other embodiments injector 22 may be coupled to mixing chamber 28 and reactor 18. When injector 22 is coupled to mixing chamber 28 and reactor 18 there may exist a system for controlling the flow from injector 22 to mixing chamber 28 and reactor 18. Injector 22 may function to transfer a solvent over a range of pressures necessary to solvate the nanoparticles precursors and the capping agent. Injector 22 may include tube 30 and pump 32. Tube 30 may include a moveable member or piston 34 positionable within tube 30 and adapted to inhibit material from moving within tube 30 from one side of piston 34 to another side of piston 34. Pump 32 may function to transfer material including a fluid or a gas in an end of tube 30 on one side of piston 34. The fluid or gas may exert a force on positionable piston 34, moving piston 34 and subsequently exerting a force on a solvent located in tube 30 on an opposite side of piston 34.

In some embodiments, continuous flow system 16 may be sealed from outside contamination and under an inert atmosphere. Use of an inert atmosphere may reduce the extent of incidental oxidation of the surface of the crystalline composition.

Figure 2:
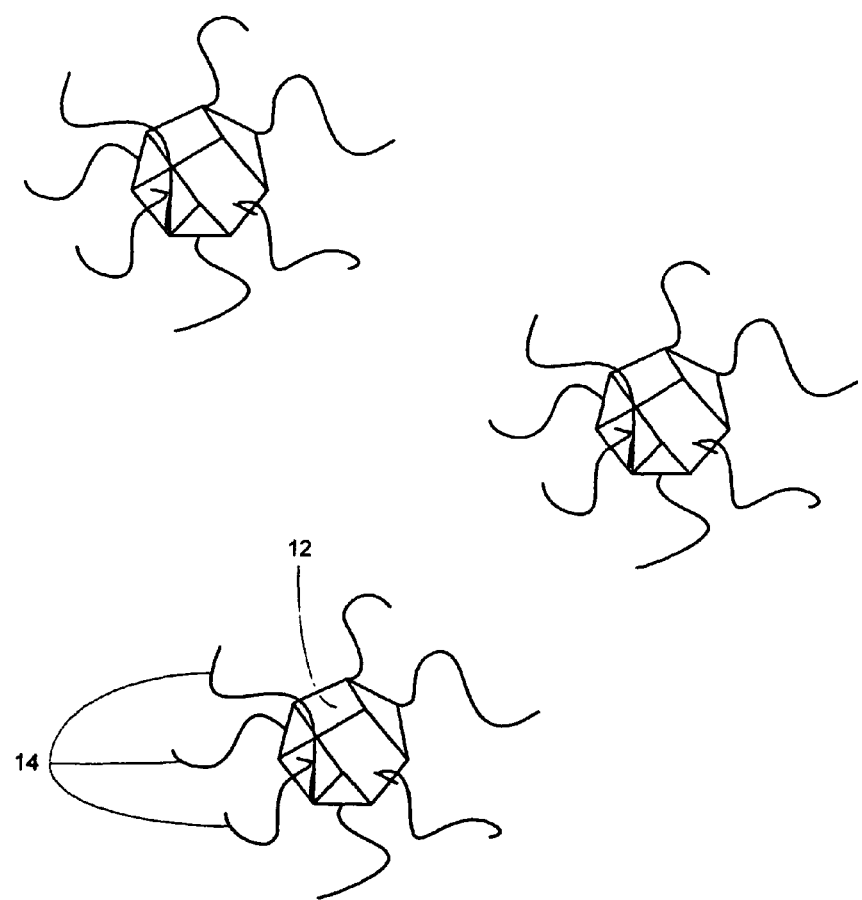
FIG. 2 depicts an embodiment of the invention showing a sterically stabilized nanoparticle with attached capping ligands.

FIG. 2 illustrates an example of sterically stabilized nanoparticles 12. Shown in FIG. 2 are capping agents 14 coupled to the nanoparticles. Capping agents 14 may be flexible organic molecules, alkanes are a non-limiting example, that typically provide repulsive interactions between nanoparticles 12 in solution. The repulsive nature of capping agents 14 typically prevents uncontrolled growth and aggregation of nanoparticle 12. Generally, the core of nanoparticle 12 tends to be well defined and faceted. However, in other embodiments, the particles may be spherical or ellipsoidal. In one embodiment, the nanoparticle core may be amorphous.

Nanoparticles produced using the method described herein may be structurally, chemically, and optically characterized. For example, nanoparticles may be characterized by transmission electron microscopy (EM), energy-dispersive X-ray spectroscopy (EDS), Fourier transform infrared spectroscopy (FTIR), UV-visible absorbance, and luminescence (both PL and PLE) spectroscopy data. In certain embodiments, nanoparticles may be crystalline cores coated by hydrocarbon ligands bound through covalent alkoxide bonds or interactions of a thiol group with the nanoparticle surface. In other embodiments the nanoparticle cores may be bonded covalently through an Si—C linkage. The nanoparticles may have residual oxygen, or sulfur on their surfaces. The nanoparticles typically luminesce with size-tunable color, from the blue (approximately 15 Å diameter for silicon nanoparticles) to green (approximately 25 to 40 Å diameter for silicon nanoparticles) into the yellow, orange and red for particles that can be in up to 80 Å in diameter. The nanoparticles may exhibit charge transfer between neighboring particles. Typically, the emission color depends also on the excitation energy, either by photo or electrical means.

In one embodiment, nanoparticles may be stimulated so as to emit light. Discrete optical transitions also may appear in the absorbance and photoluminescence excitation (PLE) spectra of the nanoparticles, which is generally consistent with quantum confinement effects in semiconductors. The particle distribution is typically within a standard deviation about the mean particle diameter. The appearance of discrete optical transitions, or peaks, in the absorbance and/or luminescence spectra typically indicates a narrow size distribution, as the optical properties of the nanoparticles themselves are size-dependent. Furthermore, the appearance of discrete peaks typically indicates the homogeneous chemical nature of nanoparticles, including core chemistry, crystallinity, surface chemistry and chemical coverage. In certain embodiments particle size distribution may affect the appearance of discrete transitions in the optical spectra Typically in these small particles, the energy levels have separated significantly compared to bulk silicon, making these transitions observable, an effect of quantum confinement. In certain embodiments particle surface chemistry may affect the appearance of discrete transitions in the optical spectra and may broaden the PL emission energies.

In some embodiments, nanoparticles may exhibit previously unobserved discrete electronic absorption and luminescence transitions due to quantum confinement effects. Nanoparticles described herein may exhibit discrete electronic absorption and luminescence transitions due to quantum confinement effects that are dependent upon the size of the nanoparticles. Differences in the discrete optical properties due to differences in the size of the nanoparticles may translate into differently sized nanoparticles emitting light at different wavelengths and colors. Several non limiting examples include: silicon nanoparticles with an average diameter of about 2 nm emitting a blue light; silicon nanoparticles with an average diameter of about 3.5 nm emitting a green light; silicon nanoparticles with an average diameter of about 4.5 nm emitting a yellow light; silicon nanoparticles with an average diameter of about 6 nm emitting an orange light; and silicon nanoparticles with an average diameter of about 7-8 nm emitting a red light. In certain embodiments, the surface chemistry may shift the emission energies to slightly lower values. For example, 2 nm silicon nanoparticles may emit green light, or even in the case of very heavy surface oxidation, for example, although the surface coating is not limited to oxygen, these particles may emit orange or red light. Studies confirm that silicon clusters as small as 15 Å may behave as indirect semiconductors. The method for nanoparticle formation may be applied to other materials, such as nanowires, that typically require temperatures greater than the boiling point of available solvents under ambient pressure, typically greater than 350° C., for crystal formation. Absorbance of the compositions may range from approximately 1000 nm to approximately 350 nm. In particular embodiments, the compositions may be excited electronically. The compositions may display photoluminescence at 300 nm to 1000 nm. Generally, photoluminescence decays by less than 50% when exposed to the atmosphere for 30 days. In particular embodiments of the invention the size of nanoparticles typically produced are in the approximate range of 10 Å to 200 Å and larger. In other embodiments the size of the nanoparticles typically produced are in the approximate range of 15 to 40 Å. Size distributions that display discrete optical transitions typically are 15 to 25 Å and may be luminescent at 350 to 500 nm.

In some embodiments, nanoparticles may exhibit shorter photoluminescence lifetimes than those previously observed for the same element For example, porous silicon and oxide capped silicon nanoparticles have previously exhibited microsecond scale photoluminescence lifetimes. Examples of silicon nanoparticles formed by methods described herein exhibit a photoluminescence lifetime (greater than 96% of the total photoluminescence lifetimes) of less than or equal to 20 ns. An example of an octanethiol-capped silicon nanoparticles exhibits characteristic lifetimes with a fast component (~100 picoseconds) and two slow components with lifetimes ranging from 2 to 6 ns. The slow components photoluminescence lifetimes observed for the octanethiol-capped silicon nanoparticles example are at least three orders of magnitude faster than those previously found for porous silicon and silicon nanoparticles. The measured lifetime relates to the radiative and non-radiative electron-hole recombination processes. Faster electron-hole recombination processes may be better for certain applications such as light emitting devices or light emitting diodes (LEDs) and optical switches. Coating the nanoparticles with a different wider band gap semiconductor, such as CdS or ZnS, may reduce the non-radiative rates. Coating the nanoparticles with a smaller band gap semiconductor like Ge may increase the photoluminescence lifetime in the particles. For certain applications, the photoluminescence lifetime may be increased through the use of different capping ligands.

Nanoparticles described herein may be relatively stable when charging the nanoparticles with electrons or electron holes. Stability of the nanoparticles during charging with electrons and electron holes may make the nanoparticles suitable for floating gate memory. In another embodiment, stability of the nanoparticles during charging may make these materials suitable for photocatalytic or battery applications.

Nanoparticles described herein may exhibit quantized, or discrete, charging. Quantized charging may allow for use of the nanoparticles in multi-valued logic applications. The nanoparticles may exhibit reversible multiple charge transfers. Reversible charge transferring of nanoparticles may allow for light emission by charge injection, or electrogenerated chemiluminescence. The nanoparticles may emit light under repetitive electrode potential cycling or pulsing between nanoparticles oxidation and reduction. In electrogenerated chemiluminescence experiments, electron transfer annihilation of electrogenerated anion and cation radicals results in the production of excited states:

(1)

(2)

In this case, $R^-$ and $R^+$ refer to negatively and positively charged silicon nanoparticles electrogenerated at an electrode (for example, Pt), which then react in solution to give the excited state $R^*$ as illustrated in reaction 1 and 2 herein. This property may form the basis for sensor technologies.

Nanoparticles of other metals may be formed by heating organometallic precursors in the presence of a capping agent. For example, Group II-VI and Group III-V nanoparticles may also be prepared by using methods similar to those described above for Group IV metals. Additionally, nanoparticles of Group II, Group III, Group V, and Group VI metals may be formed using methods similar to those described above for the Group IV metals. In one embodiment, nanoparticles may be formed by reacting one or more organometallic precursors in the presence of a capping agent. The organometallic precursors and capping agent may be heated at a pressure greater than 1 atm. in a reaction vessel. Heating of the organometallic precursors results in the thermal degradation of the organometallic precursor, which in turn leads to the formation of nanoparticles. The precursors may degrade through a free radical mechanism, or it may degrade through thermolysis. The dimensions of the nanoparticles may be controlled by reaction conditions and the capping agent used. The reaction conditions used to control the particle size may include, for example, the temperature, pressure, precursor concentration, capping ligand concentration, solvent, precursor composition and capping agent composition. In one embodiment a free radical initiator may be added to the reaction. It is believed that the capping agent may aid in controlling the dimensions of the formed nanoparticles by inhibiting growth of the nanoparticles. The capping agent may also prevent reactive degradation of the nanoparticles when exposed to water and oxygen and other chemical contamination.

A Group II organometallic precursor may be a Group II metal that includes organic groups. As used herein a "Group II metal" includes the elements of zinc, cadmium, and mercury. Group II organometallic precursors include, but are not limited to organozinc, organocadmium and organomercury compounds. Some examples of Group II organometallic precursors include, but are not limited to, alkylzincs, alkylcadmiums, alkylmercurys, arylzincs, arylcadmium and arylmercury. Examples of organometallic zinc precursors include, but are not limited to, dimethyl zinc, diethyl zinc, and diphenyl zinc. Examples of organometallic cadmium precursors include, but are not limited to, dimethyl cadmium, diethyl cadmium, and diphenyl cadmium. Examples of organometallic mercury precursors include, but are not limited to, dimethyl mercury, diethyl mercury, and diphenyl mercury. Organometallic zinc and organometallic mercury precursors may be formed by the reaction of metallic mercury or zinc with an alkyl or aryl halide by known methods. Organometallic cadmium precursors may be formed by the reaction of cadmium halides with Grignard reagents (e.g., RMgX) by known methods.

A Group VI organometallic precursor may be a Group VI metal that includes organic groups. As used herein a "Group VI metal" includes the elements of selenium tellurium. Group VI organometallic precursors include, but are not limited to organoselenides, organotellurides. Some examples of Group VI precursors include, but are not limited to, dialkylselenides, dialkyltellurides, diarylselenides, diaryltellurides, dialkyldiselenides, dialkylditellurides, diaryldiselenides, diarylditellurides. Examples of organometallic selenium precursors include, but are not limited to, dimethylselenide, diethylselenide, diphenylselenide, dimethyldiselenide, diethyldiselenide, and diphenyldiselenide. Examples of organometallic tellurium precursors include, but are not limited to, dimethyltelluride, diethyltelluride, diphenyltelluride, dimethylditelluride, diethylditelluride, and diphenylditelluride. Organometallic selenium and tellurium precursors may be formed by the reaction of sodium selenide or sodium telluride with alkyl or aryl halides by known methods.

A Group III organometallic precursor may be a Group III metal that includes organic groups. As used herein a "Group III metal" includes the elements of boron, aluminum, gallium, indium, and thallium. Group III organometallic precursors include, but are not limited to organogallium compounds, organoindium compounds, and organothallium compounds. Some examples of Group III precursors include, but are not limited to, trialkylgallium compounds, trialkylindium compounds, trialkylthallium compounds, triarylgallium compounds, triarylindium compounds, triarylthallium compounds. Examples of organometallic gallium precursors include, but are not limited to, trimethylgallium and triphenylgallium. Examples of organometallic thallium precursors include, but are not limited to, trimethylthallium and triphenylthallium. Examples of organometallic indium precursors include, but are not limited to, trimethylindium and triphenylindium. Organometallic gallium, indium, and thallium precursors may be formed by the reaction of the appropriate metal halide (e.g., $GaCl_3$, $InCl_3$, or $TlCl_3$) with Grignard reagents (e.g., RMgX) or trialkyl- or triaryl aluminum compounds by known methods.

A Group V organometallic precursor may be a Group V metal that includes organic groups. As used herein a "Group V metal" includes the elements of phosphorus, arsenic, and antimony. Group V organometallic precursors include, but are not limited to organophosphorus compounds, organoarsenic compounds, and organoantimony compounds. Some examples of Group III precursors include, but are not limited to, trialkylphosphorus compounds, trialkylarsenic compounds, trialkylantimiony compounds, triarylphosphorus compounds, triarylarsenic compounds, triarylantimony compounds. Examples of organometallic phosphorus precursors include, but are not limited to, trimethylphosphine and triphenylphosphine. Examples of organometallic arsenic precursors include, but are not limited to, trimethylarsenide and triphenylarsenide. Examples of organometallic antimony precursors include, but are not limited to, trimethylantimony and triphenylantimony. Organometallic phosphorus compounds are commercially available. Organometallic gallium, indium, and thallium precursors may be formed by the reaction of the appropriate metal halide (e.g., $GaCl_3$, $InCl_3$, or $TiCl_3$) with Grignard reagents (e.g., RMgX) or trialkyl- or triaryl aluminum compounds by known methods.

Nanoparticles may be formed by taking one or more of the Group II, III, IV, V, or VI organometallic precursors and heating them in the presence of a capping agent. In one embodiment, the organometallic precursor and the capping agent may be reacted at supercritical conditions. The reaction may be conducted at or above the critical point of the capping agent. Alternatively, a solvent may be used. The reaction may be conducted above the critical point of the solvent, the capping agent, or both the solvent and the capping agent. The solvent and capping agent are as defined previously.

Nanoparticles of any of the Group II, III, V, V or VI may be formed as described above. In another embodiment, nanoparticles composed of mixtures of Group II, III, IV, V, and VI. Mixtures include mixtures within a group and mixtures between groups. Mixtures within in a group may be formed by heating two or more organometallic precursors of the same group in the presence of a capping agent. For example, silicon-germanium nanoparticles may be formed by heating a mixture of a silicon organometallic precursor (e.g., diphenylsilane) and a germanium organometallic precursor (e.g., diphenylgermane), a capping agent, and, optionally, a solvent. In one embodiment, the reaction is conducted at supercritical conditions. The decomposition of the organometallic precursors may lead to formation of silicon-germanium nanoparticles.

In another embodiment, nanoparticles that include mixtures of elements from different groups may be formed. One common group of semiconductor materials are the Group II-VI semiconductors. These materials are typically composed of mixtures of Group II metals and Group VI metals. Group II-VI nanoparticles may be formed by heating a mixture of one or more Group II organometallic precursors, one or more Group VI organometallic precursors, a capping agent, and, optionally, a solvent Decomposition of the organometallic precursors may lead to Group II-VI nanoparticles. In one embodiment, the reaction is conducted at supercritical conditions. For example, cadmium-selenide nanoparticles may be produced by heating a mixture of a cadmium organometallic precursor (e.g., dimethyl cadmium) and a selenium organometallic precursor (e.g., diphenyldiselenide) in the presence of a capping agent.

Group III-V nanoparticles may be formed by heating a mixture of one or more Group III organometallic precursors, one or more Group V organometallic precursors, a capping agent, and, optionally, a solvent. Decomposition of the organometallic precursors may lead to Group III-V nanoparticles. In one embodiment, the reaction is conducted at supercritical conditions. For example, gallium-arsenide nanoparticles may be produced by heating a mixture of a gallium organometallic precursor (e.g., trimethyl gallium) and an arsenic organometallic precursor (e.g., trimethyl arsenide) in the presence of a capping agent. In another example, Indium-gallium-arsenide nanoparticles may be formed by heating a mixture of a gallium organometallic precursor (e.g., trimethyl gallium). an arsenic organometallic precursor (e.g., trimethyl arsenide) and an indium organometallic precursor (e.g., trimethyl indium) in the presence of a capping agent. Other materials that may be formed include, but are not limited to, indium-phosphide, indium-aresenide, and gallium-phosphide.

Group IV-V nanoparticles may be formed by heating a mixture of one or more Group IV organometallic precursors, one or more Group V organometallic precursors, a capping agent, and, optionally, a solvent. Decomposition of the organometallic precursors may lead to Group IV-V nanoparticles. In one embodiment, the reaction is conducted at supercritical conditions. For example, phosphorus doped silicon nanoparticles may be produced by heating a mixture of a silicon organometallic precursor (e.g., diphenylsilane) and a phosphorus organometallic precursor (e.g., triphenyl phosphine) in the presence of a capping agent.

Group IV-III nanoparticles may be formed by heating a mixture of one or more Group IV organometallic precursors, one or more Group III organometallic precursors, a capping agent, and, optionally, a solvent Decomposition of the organometallic precursors may lead to Group IV-III nanoparticles. In one embodiment, the reaction is conducted at supercritical conditions. For example, boron doped silicon nanoparticles may be produced by heating a mixture of a silicon organometallic precursor (e.g., diphenylsilane) and a boron organometallic precursor (e.g., triphenylborane) in the presence of a capping agent.

Group IV nanoparticles that are doped with rare earth elements may also be formed by heating one or more Group IV organometallic precursors, one or more rare earth elements, a capping agent, and, optionally, a solvent. Decomposition of the organometallic precursors may lead to Group IV nanoparticles that are doped with one or more rare earth elements. In one embodiment, the reaction is conducted at supercritical conditions. Rare earth elements include lanthanum, cerium, praseodymium, neodymium, promethium, samarium, europium, gadolinium, terbium, dysprosium, holmium, erbium, thulium, ytterbium, and lutetium. For example, ytterbium doped silicon nanoparticles may be produced by heating a mixture of a silicon organometallic precursor (e.g., diphenylsilane) and an ytterbium precursor in the presence of a capping agent.

Other metal precursors of other metal groups (including the transitional metals) may be heated to form nanoparticles. Many complexes of metals with small organic molecules and carbon monoxide may be formed. For examples, many metals may form complexes with one or more cycopentadienes to form metallocenes. Many metallocenes exhibit some solubility in organic solvents. Metallocenes may be decomposed by heating to high temperatures. When heated to high temperatures in the presence of a capping agent, and, optionally a solvent nanoparticles may be formed. In some embodiments, the reaction is conducted above the supercritical point of the capping agent and/or solvent. Examples of metallocenes include, but are not limited to, ferrocene, cobaltocene, nickelocene, titanocene dichloride, zirconocene dichloride, and uranocene. When decomposed these metallocenes may lead to iron, cobalt, nickel, titanium, zirconium, or uranium nanoparticles respectively. The formation of metal nanoparticles may be aided by the addition of a reducing agent Reducing agents include, but are not limited to, hydrogen and hydride compounds. Hydride compounds include, but are not limited to, lithium aluminum hydride, lithium borohydride, and sodium borohydride.

Metal salts may also be used as precursors for the formation of metal nanoparticles and/or metal oxide nanoparticles. In one embodiment, metal salts (e.g., metal nitrates and metal acetates) may be hydrolyzed in supercritical water to form nanoparticles of the metal or metal oxide nanoparticles. Capping agents may be used to control whether a metal nanoparticle or a metal oxide particle may be formed. For example, copper nitrate may be decomposed in supercritical water to form copper (I) oxide nanoparticles in the absence of a capping agent. When a capping agent (e.g., 1-hexanethiol) is added to copper nitrate in supercritical water the predominant product is a copper nanoparticle. Additionally, the addition of an oxidant or reducing agent may influence the products produced. Other factors, including but not limited to, precursor concentration, solution pH, and capping ligand may affect the crystal structure, size, morphology, and degree of agglomeration of the nanoparticles. Metal alloy nanoparticles may be made by hydrolyzing mixtures of metal salts.

Nanoparticles may be modified by further treatment after they have been formed. For example, silicon or germanium nanoparticles may be modified after synthesis using standard ion implantation techniques or ion diffusion techniques. For example, silicon nanoparticles may be doped by ion implantation of phosphorus to form n-type semiconductor materials.

Additionally, nanoparticles may be further modified by additional growth after synthesis. For example, after formation of a nanoparticle, a coating layer having the same composition or a different composition may be formed on the nanoparticle. The coating composition may be formed by placing the nanoparticles in the presence of a coating precursor. The coating precursor may be an organometallic precursor. Upon decomposition of the organometallic precursor, the material may form a coating on the nanoparticle. Growth of the coating may be regulating by the presence of capping agents, as described above. For example, germanium nanoparticles may be coated with a silicon coating layer. The silicon coating layer may be grown on the germanium nanoparticle using standard deposition techniques. Alternatively, the silicon may be grown on the germanium nanoparticle by placing the nanoparticle in a reactor and treating the particle with an organometallic silicon precursor. Upon decomposition of the organometallic silicon precursor, silicon may form a coating on the germanium particle. The thickness of the coating may be controlled by the reaction conditions used and the nature of the capping agent Applications:

Floating Gate Memory

In some embodiments, nanoparticles may be used in floating gate or flash memory applications. Non-volatile memory such as electrically programmable read-only memory (EPROM) and electrically-erasable programmable read-only memory (EEPROM) are used for storing data in computer systems. EPROM and EEPROM memory includes a plurality of memory cells having electrically isolated gates, referred to as floating gates. Data is stored in the memory cells in the form of a charge on the floating gates. Charge is transported to or removed from the floating gates by program and erase operations, respectively.

Another type of non-volatile memory is flash memory. Flash memory is a derivative of EPROM and EEPROM. Although flash memory shares many characteristics with EPROM and EEPROM, the current generation of flash memory differs in that erase operations are done in blocks.

A typical flash memory includes a memory array composed of a plurality of memory cells arranged in row and column fashion. Each of the memory cells includes a floating gate field-effect transistor capable of holding a charge. The cells are usually grouped into blocks. Each of the cells within a block may be electrically programmed in a random basis by charging the floating gate. The charge may be removed from the floating gate by a block erase operation. The charge may be negative or positive. The data in a cell is determined by the presence or absence of the charge in the floating gate.

Flash memories have the potential of replacing hard storage disk drives in computer systems. The advantages would be replacing a complex and delicate mechanical system with a rugged and easily portable small solid-state non-volatile memory system. There are also the possibilities that flash memories might be used to replace DRAMs. Flash memories have very high potential densities and more speed of operation, particularity in the erase operation, than DRAMS. Flash memories might then have the ability to fill all memory needs in future computer systems.

Figure 4:
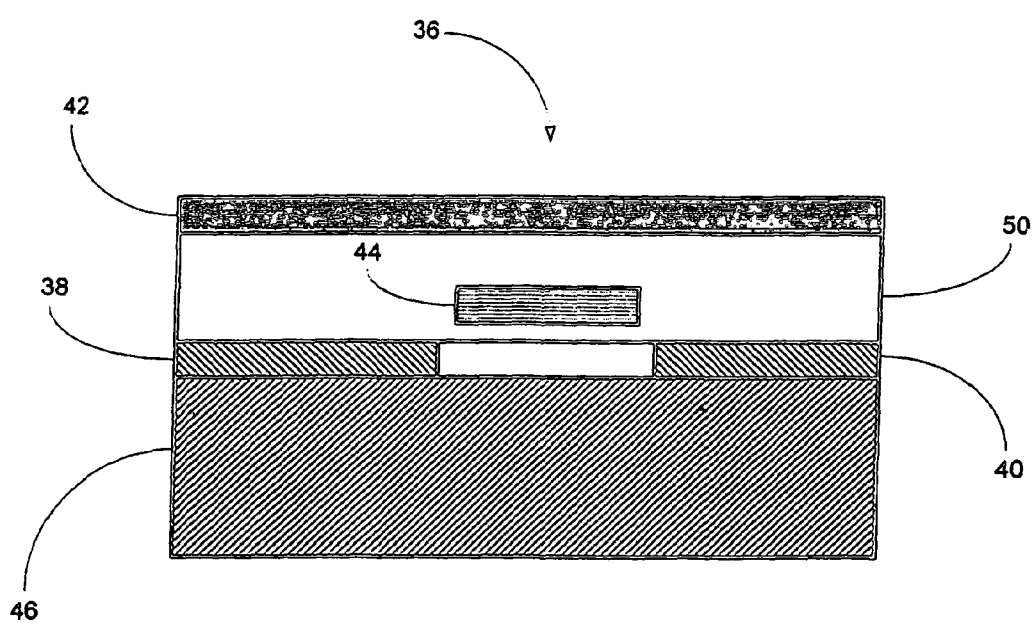
FIG. 4 depicts an embodiment of a floating gate memory device.

FIG. 4 depicts an embodiment of a floating gate field effect transistor or floating gate memory device 36. Floating gate memory device 36 may include source 38, drain 40, control gate 42, and floating gate 44. Source 38 may be formed from an N+ type of high impurity concentration. Drain 40 may be formed from an N+ type of high impurity concentration. Source 38 and drain 40 may be formed in substrate 46. Substrate 46 may be formed of a P-type semiconductor of low impurity concentration.

In some embodiments, source 38 and drain 40 may be separated from one another by a channel 48. Channel 48 may function as a conduit for electron flow. In one embodiment, the channel will be a Group IV nanowire. Floating gate 44 may be positioned between channel 48 and control gate 42. Floating gate 44 may be electrically isolated. Data can be written into floating gate memory device 36 by injecting electrons through channel 48 or substrate 46 into floating gate 44. Reversing the flow of electrons sends electrons out of floating gate 44 erasing the stored data. Writing data to non-volatile memory may function differently beginning by setting up an electric field across barrier layer 50 to attract electrons in channel 48. In another embodiment, energy may be supplied to the electrons to overcome the barrier 50. Either method may increase the threshold voltage of the floating gate memory device 36. Variation of the threshold voltage caused by the change in stored electric charges within floating gate 44 can represent different logic states, non limiting examples are '0' and '1'. To erase stored data in a non-volatile memory device a high electric field may be set up between Source 38 and control gate 42. Consequently, electrons trapped in floating gate 44 can now penetrate neighboring barrier layer 50 causing the threshold voltage to drop. This change in the threshold voltage may represent another logic state.

In some embodiments, floating gate 44 may include the nanoparticles described herein. The nanoparticles may be used as discrete nanoparticles. In another embodiment the nanoparticles may be spin-coated as a thin film to form floating gate 44. In another embodiment the nanoparticles may be drop cast as a thin film to form floating gate 44. In one embodiment, an oxide, or other dielectric material may be grown over the particles. In another embodiment, an insulating polymer or other organic molecular material might be laid on top of the particles forming the floating gate 44. The nanoparticles may exhibit quantized charging. Quantized charging means that electron injection may occur as discrete charging events with discrete threshold voltages. Quantized charging may allow for use of the nanoparticles in multi-valued logic applications. The nanoparticles may exhibit reversible multiple charge transfers. Traditional memory units only have two different logic states usually represented as '0' and '1'. Memory devices including nanoparticles described herein may be capable of attaining more than two logic states due to the nanoparticles ability to exhibit quantized charging. The basic design of memory devices is described in further detail in U.S. Pat. No. 6,331,463 B1 which is incorporated herein by reference.

In some embodiments, the particles forming the floating gate 44 will be size-monodisperse with standard deviations approximately less than 10% about the mean diameter. These particle may organize spatially into a lattice. In one embodiment, two or more distinct particle sizes will form the floating gate 44. These particles may organize spatially into bidisperse particle arrays. The particles making up the floating gate 44 may be deposited by spin-coating, spraying from solution, spraying through the rapid expansion from supercritical solution (RESS), or drop casting. The particles in the floating gate 44 may be embedded in a conducting, or an insulating, polymer. In another embodiment, the particles may be embedded in a thin gate oxide. In one embodiment, the particles making up the floating gate 44 might be evaporated and deposited from an aerosol. In embodiments with the floating gate 44 consisting of distinct classes of sizes, for example, a bimodal size distribution of particles, discrete charging events may occur due to the size dependence of the Coulomb charging of the particles. The term Coulomb charging refers to the repulsion between electrons within the nanoparticle core due to the small size of the particles. Coulomb charging leads to discrete voltage-dependent charging events, and may be utilized for multi valued logic applications, or other digital applications that use information stored as memory states higher than binary. A floating gate 44 may consist of a bimodal size distribution of nanoparticles, either the Group IV particles described herein, or possibly other nanoparticle materials, including ferromagnetic particles and ferroelectric particles.

Light Emitting Devices

Other applications using nanoparticles exhibiting discrete optical properties may include light emitting devices and applications thereof. Specific interest has been focused on the development of inexpensive and efficient light emitting diodes (LEDs).

Light emitting devices such as light emitting diodes (LEDs) have been constructed in the past using P-doped and N-doped materials. However, such devices are generally only capable of emitting color of a particular wavelength based on the semiconductor materials used in the diode. Light emitting devices have also been made using a polymeric material such as poly-(p-phenylene vinylene) (PPV) as a hole transport layer between a hole injection electrode and an electron injection electrode. However, such devices are also limited to emission of a single color, based on the type of light emitting polymeric material utilized. Thus, to vary the color, one must use a different polymer, which prevents, or at least complicates, the display of light of various colors. Furthermore, since such polymeric materials do not function as electron transport media, the recombination of holes and electrons, which results in such light emission, occurs adjacent the electron injection electrode, which tends to lower the efficiency of the device as a light source.

Nanoparticles may be used in the formation of the emissive layer in LEDs. In one embodiment, silicon nanoparticles may be used in a light emitting diode system. Silicon at nanometer dimensions has different properties than bulk silicon used in semiconductor chips. Bulk silicon does not emit light; while, silicon nanoparticles at the sub-10 nm level may exhibit luminescence over the entire visible spectrum. The specific wavelength emitted by the silicon nanoparticles may be dependent on the size of the particles. For example, 10.5 nm silicon nanoparticles emit blue light; 8 nm silicon nanoparticles emit red light.

In an embodiment, running a current across an ordered distribution of nanoparticles having particles having a average particle diameter between about 1.5 nm to about 8 nm. In one embodiment, variations in voltage, however, may not effect the color of the light emitted by the nanoparticles. This embodiment may consist of a device with size-monodisperse nanoparticles—i.e., particles with a standard deviation about the mean diameter of 50% or less, or 20% or less, or 5% in some cases. In another embodiment, a device may emit voltage-tunable color. This device may consist of a mixture of particle sizes. One example device might consist of a bimodal size distribution. Another example device might have bimodal nanoparticles that are spatially organized with either the small particles closer to the anode and the larger particles closer to the cathode, or the small particles closer to the cathode and the larger particles closer to the anode. In one embodiment, the color of the emission is voltage tunable due to charge transfer between the nanoparticles and the polymer. In this device, the particles may be embedded in the polymer layer. In one embodiment, the nanoparticles may be sandwiched between a hole transporting layer and an electron transporting layer. The charge transporting layers may be conducting polymers, or conducting small molecules, or molecular crystals. In one embodiment, a gate electrode serves to modulate the color of light emission from the particles. A gate electrode may be used to improve the efficiency of light emission in another embodiment.

In one embodiment, a light may be formed having a broad size distribution of silicon nanoparticles. The broad size distribution may be advantageous in that the combination of wavelengths emitted by the different size particles may produce a white light. The silicon nanoparticles may be embedded in a polymer matrix. The polymer matrix is not, however, necessary for the silicon nanoparticles to function effectively as the emissive layer. The size distribution of silicon nanoparticles may allow the emission of white light. The nanoparticles themselves may emit with size-independent quantum yields and lifetimes. Clusters of nanoparticles may produce a broad emission band. If energy transfer occurs between neighboring nanoparticles, it does not result in the selective emission from only the largest particles with the lowest energy gap between the highest occupied and lowest unoccupied molecular orbitals (HOMO and LUMO). This situation is qualitatively different than known technology using CdSe nanoparticles.

Figure 5:
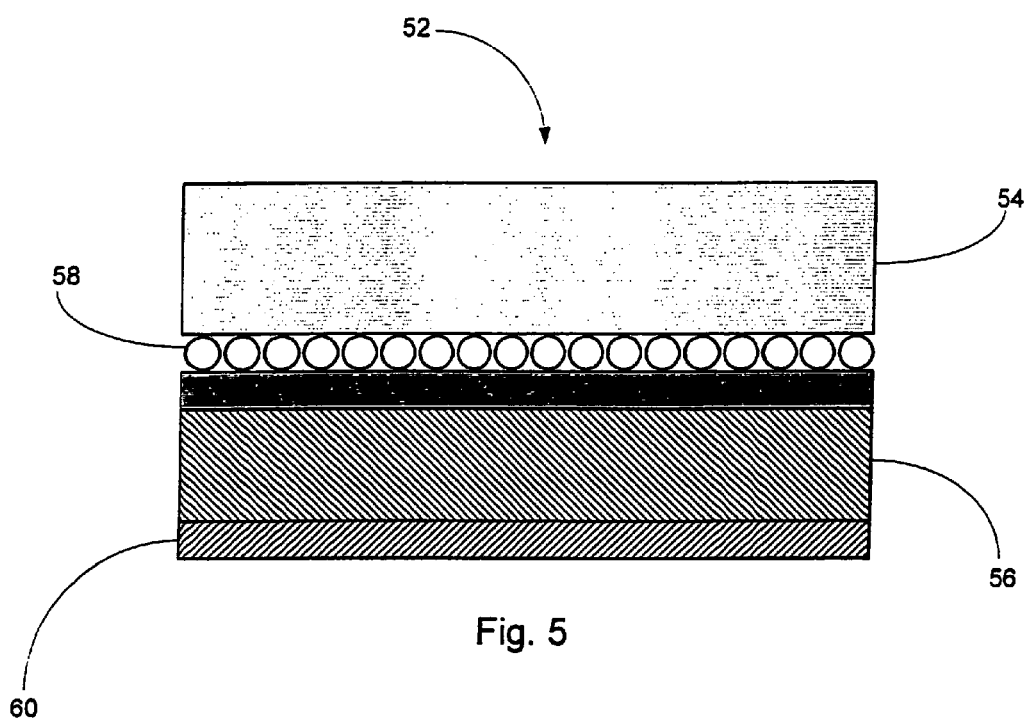
FIG. 5 depicts an embodiment of a basic design for a light emitting device.

FIG. 5 depicts an embodiment of a basic design for light emitting device 52 including nanoparticles as described herein. light emitting device 52 may include first electrode 54, second electrode 56, and emissive layer 58. Emissive layer 58 may include the nanoparticles exhibiting discrete optical properties as described herein. Emissive layer 58 may include a polymer wherein the nanoparticles may be suspended. However, nanoparticle based light emitting devices 52 may not require a polymer to emit, in contrast to many organic LEDs. Polymers may inflict losses through absorption, scattering, and poor electron-hole interfaces. Emissive layer 58 may be positioned adjacent first electrode 54. First electrode 54 may function as a cathode. Emissive layer 58 may be positioned adjacent second electrode 56. Second electrode 56 may function as an anode.

In an embodiment, second electrode 56 may include substrate 60. Substrate 60 may include a transparent conductive oxide layer. Non-limiting examples of the transparent conductive oxide layer may include indium tin oxide, tin oxide, or a translucent thin layer of Ni or Au or an alloy of Ni and Au. The basic design of light emitting devices is described in further detail in U.S. Pat. No. 5,977,565 which is incorporated herein by reference.

In an embodiment, the nanoparticles may emit light by optical stimulation. In this device, an optical excitation source is used in place of electrical stimulation. However, in another embodiment, a combination of optical excitation and electrical stimulation may be used to enhance device performance, such as overall energy efficiency or perhaps color tenability.

Lasers

An extension of the application of nanoparticles in light emitting devices is the use of nanoparticle based light emitting devices for coherent light generation and optical gain applications. The basic problem impeding the efficient operation of optically-pumped solid-state lasers is that the typical solid-state laser materials consist of a wide bandgap insulating host material doped with optically active impurity atoms. The impurities are typically either rare-earth ions ($Nd^{3+}$, $Er^{3+}$) or the transition metals ions ($Cr^{3+}$, $Ti^{3+}$). The absorption spectrum of such ions is characterized by the lines associated with the transitions between the shielded (and thus narrow) f or d atomic levels. However, most of the pump sources for such lasers, such as high pressure gas discharge or incandescent lamps, are characterized by their extremely wide emission spectrum. Therefore, only a small percentage of the pumped light is actually absorbed by the laser material. For a small diameter laser rod, this is typically less than 10%. As a result, the flashlamp pumped solid-state laser usually requires a bulky power supply and a water cooled system. Besides inefficiency, this renders the laser system useless for applications where portability is a key requirement.

In recent years, the laser diode has emerged as a promising alternative to flashlamp pumping of solid-state lasers. The high pumping efficiency compared to flashlamps, stems from the better spectral match between the laser-diode emission and the rare-earth absorption bands. As a result, the thermal load on both the laser rod and the pump is reduced. The system weight and power consumption are also substantially reduced with increased reliability. However, the cost of the diode laser arrays makes it expensive. In addition, the laser diodes require high current power supplies that are usually heavy rendering the lasers impractical for airborne and space applications. Therefore, scientists have been trying to harness an alternative energy pump source.

In response to the need for a more practical and efficient energy pump source the light emitting devices based on the nanoparticles described herein may be used. In an embodiment, the nanoparticles may emit light by optical stimulation. In this device, an optical excitation source is used in place of electrical stimulation. Optical excitation sources may include natural sources such as sunlight or from manmade sources, for example flashlamps. However, in another embodiment, a combination of optical excitation and electrical stimulation may be used to enhance device performance, such as overall energy efficiency or perhaps color tenability. Other sources of excitation include an electron beam from, for example, an electron gun.

In some embodiments, the nanoparticles may include doping agents to increase efficiency. Examples of appropriate doping agents include rare earth ions and transition metal ions.

In certain embodiments, the nanoparticles may be coated or embedded in materials acting as a support for the nanoparticles. The support material may have a lower refractive index than that of the nanoparticles. The support material may also be transparent to the exciting radiation.

Figure 9:
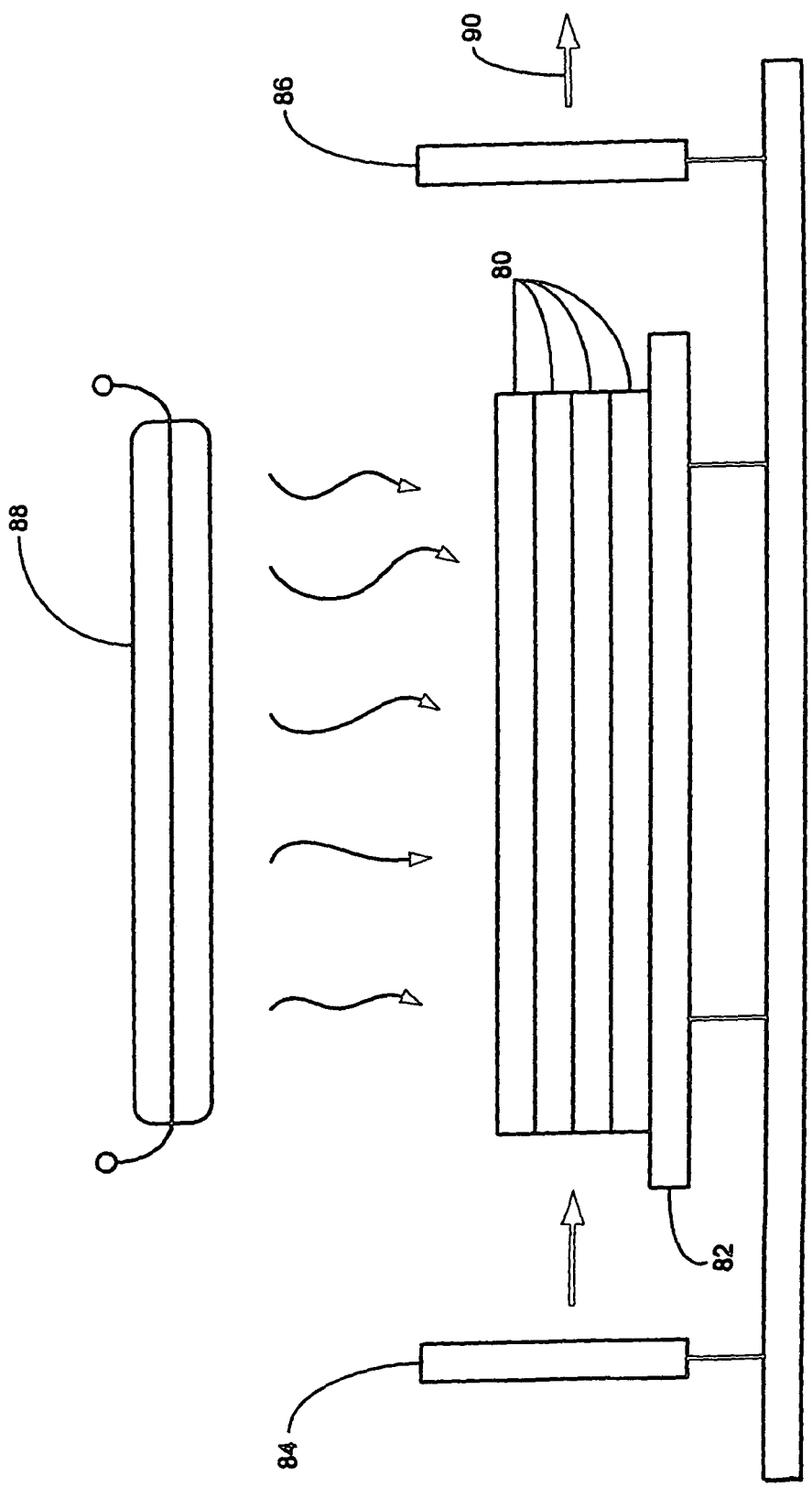
FIG. 9 depicts an embodiment of a basic design for a laser with an optical excitation source.

FIG. 9 depicts an embodiment of a basic design for laser assembly or coherent light emitting device 78. Laser assembly 78 may include nanoparticle layers 80, substrate 82, mirrors 84 and 86 and lamp 88. Nanoparticle layers 80 may be positioned on substrate 82. Substrate 82 may act as a support base for nanoparticle layers 80. Mirrors 84 and 86 may form an optical cavity for laser assembly 78. Mirror 84 may be reflective towards radiation on the right side, effectively 100%. The left side of mirror 84 may or may not be reflective to assist in controlling radiation entering the optical cavity. Mirror 86 may be slightly transparent (about 1%) to allow laser radiation between mirrors 84 and 86 to exit as a beam in a controlled manner. Lamp 88 may be positioned to illuminate nanoparticle layers 80 on substrate 82. Nanoparticle layers 80 absorb the light from lamp 88 exciting the nanoparticles causing the nanoparticles to emit light into the optical cavity where it is trapped. The trapped light is then outputted as laser beam 90 from mirror 86.

In some embodiments, nanoparticle layers 80 may be tailored to match the emission source. In an embodiment where the emission source is a broadband emission source, there may be multiple layers of nanoparticles 80 as depicted in FIG. 9. As shown in FIG. 9 there may be four nanoparticle layers 80. In this embodiment, where the emission source is a low pressure gas discharge lamp (with a wide bandwidth emission), first nanoparticle layer 80 (first layer distinguished as being closest to lamp 88) may include relatively smaller sizes of the nanoparticles described herein. The result of using the smaller nanoparticles being that their bandgap is larger thereby lowering the absorption edge and rendering the layer more absorptive of the longer wavelength radiation. Second nanoparticle layer 80 (adjacent first nanoparticle layer 80), may include nanoparticles of a somewhat larger size, with the result that the second layer will be more absorptive of shorter wavelength radiation. Third nanoparticle layer 80 (adjacent second nanoparticle layer 80), may include nanoparticles of a somewhat larger size than the second layer, with the result that the third layer will be more absorptive of shorter wavelength radiation than the second layer. Finally fourth nanoparticle layer 80 (positioned between the third layer and substrate 82) may have the largest nanoparticle sizes and thus will have an absorption edge at the shortest wavelengths (which tend to penetrate deeper). In this way, more of the energy of the incident radiation from lamp 88 will be absorbed thereby improving the absorption efficiency of the system.

In other embodiments there may be fewer nanoparticle layers 80 (for example, 1, 2, or 3) or there may be more than four nanoparticle layers 80. The narrower the bandwidth of lamp 88, the fewer nanoparticle layers 80 necessary. In other embodiments there may be only one nanoparticle layer 80 including a wide distribution of size ranges to absorb a broader bandwidth of light Nanoparticle layers 80 may be oriented in any direction and not necessarily the direction depicted in FIG. 9.

In other embodiments, an excitation source may be used to assist the nanoparticle layer(s) to emit light. The excitation source may include any type of energy capable of inducing the nanoparticles to emit light. Non limiting examples of an excitation source are flashlamps, sunlight, and electricity.

Figure 10:
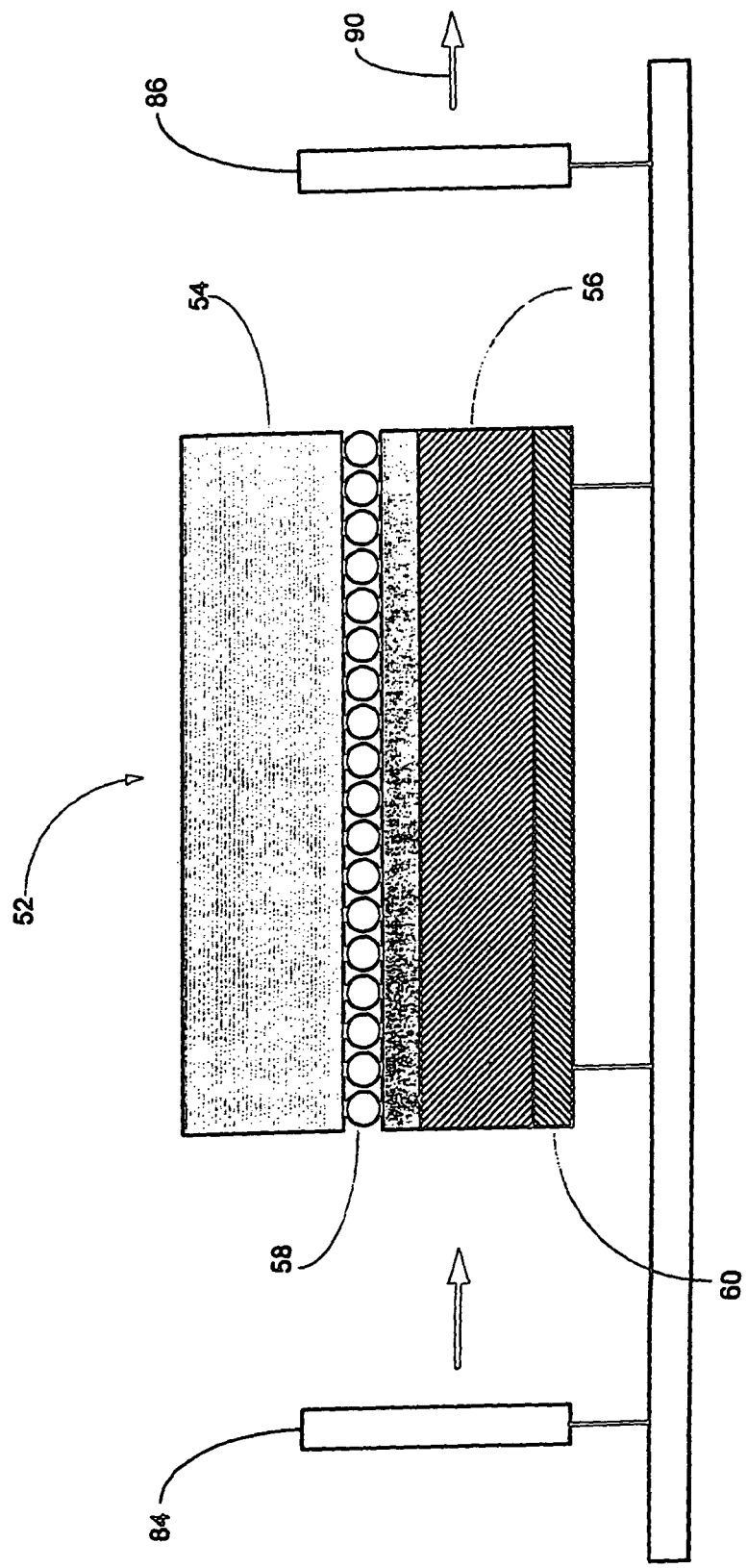
FIG. 10 depicts an embodiment of a basic design for a laser using an electrical excitation source.

FIG. 10 depicts an embodiment of a basic design for a laser using an electrical excitation source. This embodiment traps light in an optical cavity as described herein for the embodiment depicted in FIG. 9. The difference is that the nanoparticles are not excited optically but electrically. In this embodiment a devise similar to light emitting device 52 described herein and depicted in FIG. 5 may be incorporated to emit the light which is trapped in the optical cavity. Light emitting device 52 may be electrically coupled to a power source (not shown). Multiple light emitting devices 52 may form an array between mirrors 84 and 86. light emitting devices 52 may be oriented in any direction and not necessarily the direction depicted in FIG. 10. The basic design of coherent light emitting devices (commonly known as lasers) and various embodiments are described in further detail in U.S. Pat. No. 5,422,907 which is incorporated herein by reference.

Various uses for the nanoparticle based lasers described herein may be envisioned by those skilled in the art. An example of a use for the nanoparticle based laser may be as an optical switch in communications arrays or in information processing, for example in computers. Further general information regarding the structure and formation of optical switches may be found in U.S. Pat. No. 6,337,762 B1 which is incorporated herein by reference.

Displays

An extension of the application of nanoparticles in light emitting devices is the use of nanoparticle based light emitting devices in display devices. Display devices, such as flat panel displays, are currently produced using liquid crystal technology. The current liquid crystal technology currently in use in flat panel displays are limited due to manufacturing expense, high power consumption, and technical limitations such as a relatively narrow viewing angle. Organic LEDs (OLED), molecular and polymer based, are also currently under consideration as a replacement for the liquid crystal technology. Unfortunately, OLEDs are limited by short lifetimes and a catastrophic sensitivity to water and oxygen. OLED lifetimes decrease even more with increasing brightness (and increasing current), which has relegated them to small display applications such as cell phone screens.

Figure 6:
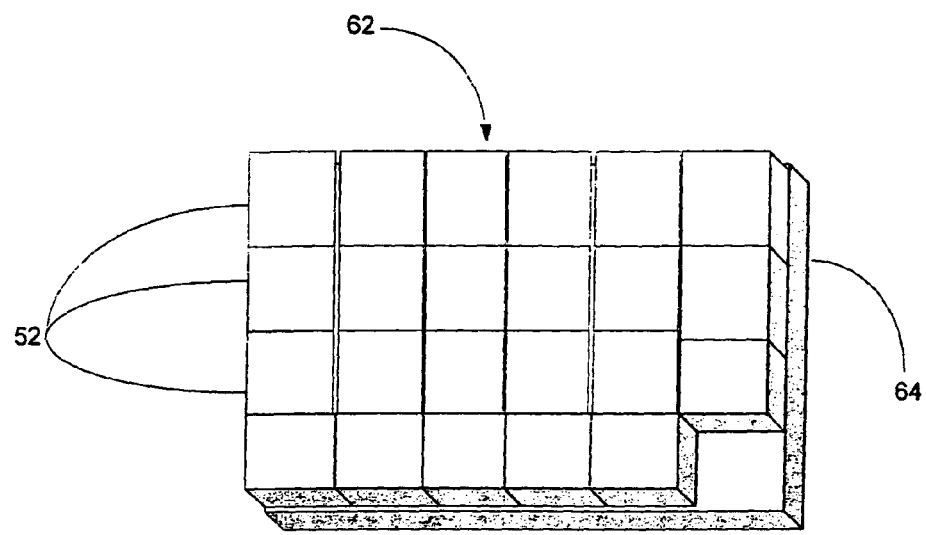
FIG. 6 depicts an embodiment of a basic design for a flat panel display.

FIG. 6 depicts an embodiment of display 62 including a plurality of light emitting devices that include nanoparticles as described herein. Display 62 may be a flat panel display. Display 62 may include a support 64. The use of discrete nanoparticles may allow nanoparticle based light emitting devices 52 to be mounted on flexible support 64. Flexible support 64 may allow for the formation of a flexible display which might be more difficult to damage and easier to transport. The display may include sets of different colored nanoparticle based light emitting devices 52. Nanoparticle based light emitting devices 52 may function as described herein. The colors of the nanoparticle based light emitting devices 52 may include any combination of colors capable of producing alone or in combination the colors necessary for the envisioned application of display 62. Commonly used colors may include red, blue, and green.

In another embodiment, display 62 may include one or more layers of colored transparent layers of nanoparticle based light emitting devices 52. The colored transparent layers of nanoparticle based light emitting devices 52 may emit light alone or in combination to achieve colors not possible when individual colored layers are used. The colored transparent layers of light emitting devices 52 may emit light from a portion of light emitting devices 52 within a particular layer or from the entire colored layer.

Figure 7:
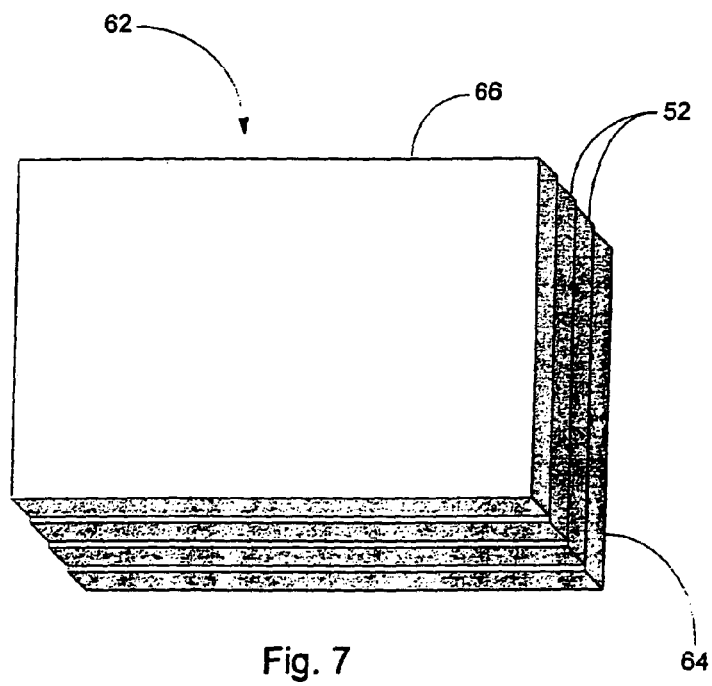
FIG. 7 depicts an embodiment of a basic design for a flat panel display including multiple layers of transparent light emitting devices.

FIG. 7 depicts an embodiment of a basic design for a flat panel display including multiple layers of transparent nanoparticle based light emitting devices. Some embodiments of display 62 may include electrical connectors that provide electrical power or signals to the individual light emitting devices. The application or absence of an electrical signal may determined whether the light emitting devices 52 emit light or remain in an unlighted state.

In an embodiment, a display may include an input to receive display information. The input may function to control the intensity of the light emitted by the light emitting diodes. The input may function to control the color of the light emitted by the display screen by controlling which of the light emitting devices are activated at a given time. The input may control the color of the light emitted in any number of ways. In one embodiment, one or more of several different colored light emitting devices may be signaled to emit simultaneously combining to appear as if a different color, other than of the actual light emitting devices themselves is being emitted. The input means may function to control what portion of the light emitting devices forming the array emit light.

Some embodiments of a display may include a transparent cover 66. Transparent cover 66 may be positioned over at least a portion of the light emitting diodes forming the array. Transparent cover 66 may function to assist in protecting portions of the display from physical damage. Transparent cover 66 may also serve additional functions such as reducing glare caused by lighting, natural or man made, not associated with the display panel itself.

Sensing Elements

There are many possible applications for the method and/or products thereof described herein. In an embodiment, the nanoparticles may be used to provide information about a biological state or event or to detect an analyte in a fluid. Traditional methods for detecting biological compounds in vivo and in vitro rely on the use of radioactive markers. These labels are effective because of the high degree of sensitivity for the detection of radioactivity. However, many basic difficulties exist with the use of radioisotopes. Such problems include the need for specially trained personnel, general safety issues when working with radioactivity, inherently short half-lives with many commonly used isotopes, and disposal problems due to full landfills and governmental regulations. As a result, current efforts have shifted to utilizing non-radioactive methods of detecting biological compounds. These methods often consist of the use of fluorescent molecules as tags (e.g. fluorescein, ethidium, methyl coumarin, and rhodamine) as a method of detection. However, problems still exist when using these fluorescent markers. Problems include photobleaching, spectral separation, low fluorescence intensity, short half-lives, broad spectral linewidths, and non-gaussian asymmetric emission spectra having long tails.

Fluorescence is the emission of light resulting from the absorption of radiation at one wavelength (excitation) followed by nearly immediate reradiation usually at a different wavelength (emission). Fluorescent dyes are frequently used as tags in biological systems. For example, compounds such as ethidium bromide, propidium iodide, Hoechst dyes (e.g., benzoxanthene yellow and bixbenzimide ((2'-[4-hydroxyphenyl]-5-[4-methyl-1-piperazinyl]-2,5'-bi-1H-benzimidazol) and (2'-[4-ethoxyphenyl]-5-[4-methyl-1-piperazinyl]-2,5'-bi-1H-benzimidazol)), and DAPI (4,6-diamidino-2-phenylindole) interact with DNA and fluoresce to visualize DNA. Other biological components can be visualized by fluorescence using techniques such as immunofluorescence that utilizes antibodies labeled with a fluorescent tag and directed at a particular cellular target. For example, monoclonal or polyclonal antibodies tagged with fluorescein or rhodamine can be directed to a desired cellular target and observed by fluorescence microscopy. An alternate method uses secondary antibodies that are tagged with a fluorescent marker and directed to the primary antibodies to visualize the target.

There are chemical and physical limitations to the use of organic fluorescent dyes. One of these limitations is the variation of excitation wavelengths of different colored dyes. As a result, simultaneously using two or more fluorescent tags with different excitation wavelengths requires multiple excitation light sources. This requirement thus adds to the cost and complexity of methods utilizing multiple fluorescent dyes.

Another drawback when using organic dyes is the deterioration of fluorescence intensity upon prolonged exposure to excitation light. This fading is called photobleaching and is dependent on the intensity of the excitation light and the duration of the illumination. In addition, conversion of the dye into a nonfluorescent species is usually irreversible. Furthermore, the degradation products of dyes are organic compounds that may interfere with biological processes being examined.

Another drawback of organic dyes is the spectral overlap that exists from one dye to another. This is due in part to the relatively wide emission spectra of organic dyes and the overlap of the spectra near the tailing region. Few low molecular weight dyes have a combination of a large Stokes shift, which is defined as the separation of the absorption and emission maxima, and high fluorescence output. In addition, low molecular weight dyes may be impractical for some applications because they do not provide a bright enough fluorescent signal. The ideal fluorescent label should fulfill many requirements. Among the desired qualities are the following: (i) high fluorescent intensity (for detection in small quantities), (ii) a separation of at least 50 nm between the absorption and fluorescing frequencies, (iii) solubility in water, (iv) ability to be readily linked to other molecules, (v) stability towards harsh conditions and high temperatures, (vi) a symmetric, nearly gaussian emission lineshape for easy deconvolution of multiple colors, and (vii) compatibility with automated analysis. At present, none of the conventional fluorescent labels satisfies all these requirements. Furthermore, the differences in the chemical properties of standard organic fluorescent dyes make multiple, parallel assays quite impractical since different chemical reactions may be involved for each dye used in the variety of applications of fluorescent labels.

Thus, there is a need for a fluorescent label that satisfies the above-described criteria for use in assay systems.

Figure 8:
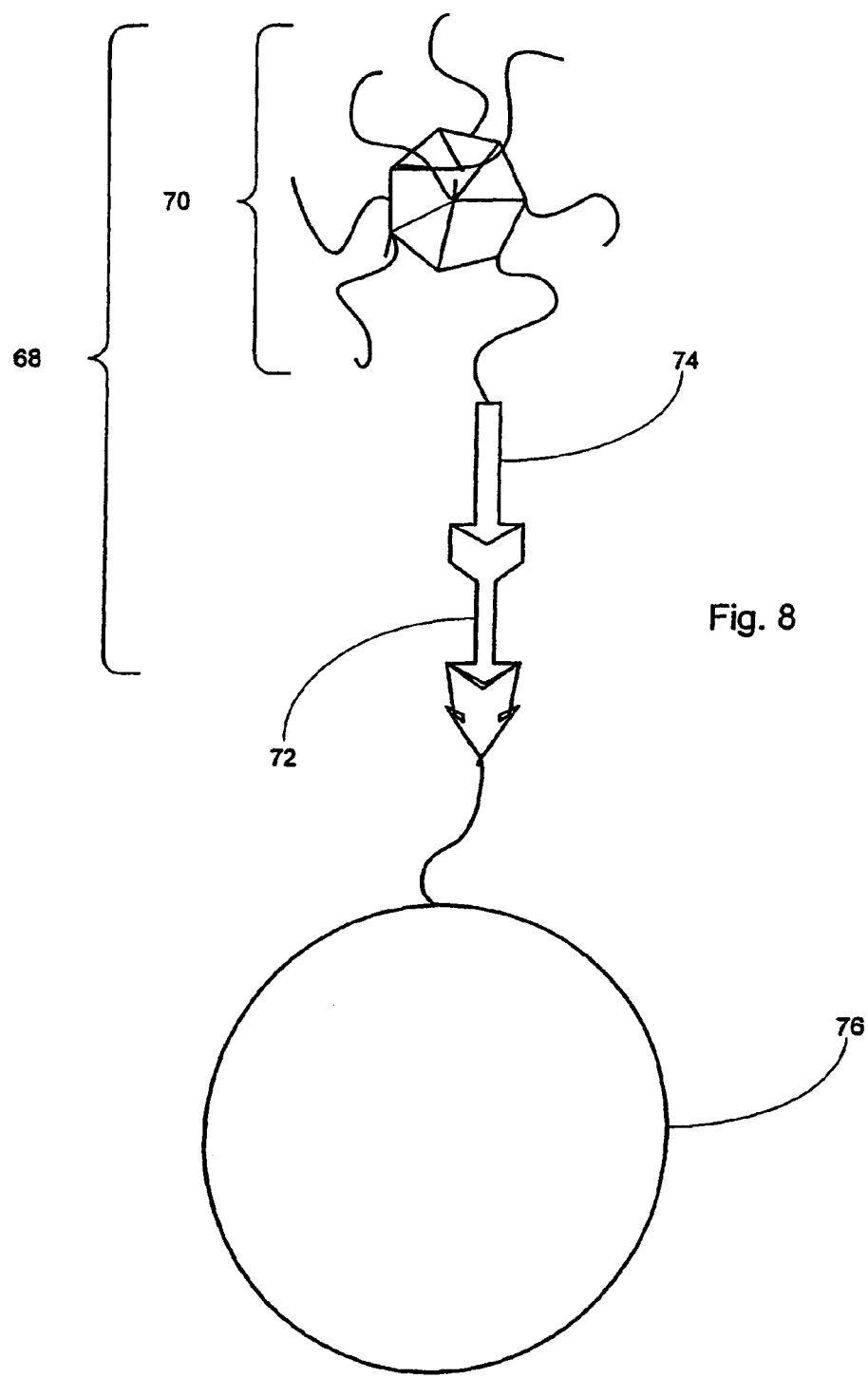
FIG. 8 depicts a schematic representation of an embodiment of a nanoparticle labeled analyte.

FIG. 8 depicts a schematic representation of an embodiment of a nanoparticle labeled analyte. Sensing element 68 may include indicator 70, receptor 72, and linker 74. Nanoparticles formed by any of the methods described herein may better satisfy the above criteria than more widely known traditional methods. Sensing element 68 may include the nanoparticles as described herein and in some embodiments possess both the ability to bind analyte 76 of interest and to create a signal. Sensing element 68 may include receptor molecules 72 which posses the ability to bind analyte 76 of interest and to create a modulated signal. Alternatively, the sensing elements may include receptor molecules and indicators. The receptor molecule may posses the ability to bind to an analyte of interest. Upon binding analyte 76, receptor 72 may cause indicator 70 to produce a signal. Receptor molecules 72 may be naturally occurring or synthetic receptors formed by rational design or combinatorial methods.

Sensing element 68, in some embodiments, possesses both the ability to bind analyte 76 and to create a signal. Upon binding analyte of interest 76, receptor molecule 72 may cause indicator molecule 70 to produce the signal. Indicator 70 may produce a distinct signal in addition to the nanoparticles included in sensing element 68. In alternate embodiments the nanoparticles themselves may be use as indicator 70. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner. The forces which drive association/recognition between molecules include the hydrophobic effect, anion-cation attraction, electrostatic attractions, covalent binding, steric interactions, chiral interactions, and hydrogen bonding. The relative strengths of these forces depend upon factors such as the solvent dielectric properties, the shape of the host molecule, and how it complements the guest. Upon host-guest association, attractive interactions occur and the molecules stick together. The most widely used analogy for his chemical interaction is that of a "lock and key." The fit of the key molecule (the guest) into the lock (the host) is a molecular recognition event.

Sensing element 68, in one embodiment, is capable of both binding the analyte(s) of interest and creating a detectable signal. In one embodiment, sensing element 68 will create an optical signal when bound to analyte of interest 76. In one embodiment, a detectable signal may be caused by the altering of the physical properties of indicator ligand 70 bound to receptor 72. In one embodiment, two different indicators are attached to receptor 72. When analyte 76 is captured by receptor 72, the physical distance between the two indicators may be altered such that a change in the spectroscopic properties of the indicators is produced. This process, known as Forster energy transfer, is extremely sensitive to small changes in the distance between the indicator molecules. In another embodiment the optical signal might be created through electron or hole donation from the nanoparticle to the analyte, or from the analyte to the nanoparticle. The analyte may quench the nanoparticle fluorescence. The nanoparticle may donate an electron to a redox active species in solution, which quenches that nanoparticle fluorescence, or changes color to be detected by absorbance measurements, or may itself fluorescence or have its fluorescence quenched.

In one embodiment, a redox enzyme is attached via covalent or noncovalent binding to the nanoparticle. The nanoparticle serves as a photoreceptor. When light with sufficient energy shines on the particle, an exciton may form, or an excited electron, or an excited hole might form. The electron or the hole may be transferred to the enzyme to provide the energy necessary to drive an enzymatically catalyzed redox reaction. The redox enzyme may be an NAD or NADH dependent enzyme, or an FAD or an FADH dependent enzyme. The enzyme may be stereospecific to produce a desired stereoisomer.

In another embodiment, indicator ligand 70 may be preloaded onto the receptor 72. Analyte 76 may then displace indicator ligand 70 to produce a change in the spectroscopic properties of sensing elements 68. In this case, the initial background absorbance is relatively large and decreases when analyte 76 is present. Indicator ligand 70, in one embodiment, has a variety of spectroscopic properties in addition to those imparted by the nanoparticles described herein which may be measured. These spectroscopic properties include, but are not limited to, ultraviolet absorption, visible absorption, infrared absorption, fluorescence, and magnetic resonance. In one embodiment, the indicator is a dye having either a strong fluorescence, a strong ultraviolet absorption, a strong visible absorption, or a combination of these physical properties. When indicator 70 is mixed with receptor, receptor 72 and indicator 70 interact with each other such that the above mentioned spectroscopic properties of indicator 70, as well as other spectroscopic properties may be altered. The nature of this interaction may be a binding interaction, wherein indicator 70 and receptor 72 are attracted to each other with a sufficient force to allow the newly formed receptor-indicator complex to function as a single unit. The binding of indicator 70 and receptor 72 to each other may take the form of a covalent bond, an ionic bond, a hydrogen bond, a van der Waals interaction, or a combination of these bonds.

For example, analytes 76 within a fluid may be derivatized with a fluorescent tag before introducing the stream to sensing elements 76. As analyte molecules are adsorbed by the sensing element, the fluorescence of the sensing element may increase. The presence of a fluorescent signal may be used to determine the presence of a specific analyte. Additionally, the strength of the fluorescence may be used to determine the amount of analyte 68 within the stream. The basic design of using nanoparticles in biological assays is described in further detail in U.S. Pat. No. 6,306,610 B1 which is incorporated herein by reference.

Receptors

A variety of natural and synthetic receptors may be used. The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers. Natural based synthetic receptors include receptors which are structurally similar to naturally occurring molecules. Polynucleotides are relatively small fragments of DNA which may be derived by sequentially building the DNA sequence. Peptides may be synthesized from amino acids. Unnatural biopolymers are chemical structure which are based on natural biopolymers, but which are built from unnatural linking units. Unnatural biopolymers such as polythioureas and polyguanidiniums may be synthesized from diamines (i.e., compounds which include at least two amine functional groups). These molecules are structurally similar to naturally occurring receptors, (e.g., peptides). Some diamines may, in turn, be synthesized from amino acids. The use of amino acids as the building blocks for these compounds allow a wide variety of molecular recognition units to be devised. For example, the twenty natural amino acids have side chains that possess hydrophobic residues, cationic and anionic residues, as well as hydrogen bonding groups. These side chains may provide a good chemical match to bind a large number of targets, from small molecules to large oligosaccharides.

In one embodiment, a polymer particle might be loaded with superparamagnetic particles, or ferromagnetic particles, or paramagnetic particles, that respond to applied magnetic fields. The Group IV nanoparticles might be attached to the magnetic polymer beads through standard chemistry. In one embodiment, the polymer particle serves as a transporter of the Group IV nanoparticles to desired locations. In one embodiment, these materials might be used for therapeutic purposes. A magnetic field may be applied to direct the nanoparticle location within the body. In one embodiment, the Group IV nanoparticles will serve as photoreceptors for therapeutic purposes. Light might be shined on the patient and absorbed by the particles to drive redox reactions within the body to destroy cancer cells. In another embodiment, heat might be generated locally by the nanoparticles upon light absorption to destroy the neighboring cells. The light source for these applications may be an ultrafast femtosecond laser, or a cw laser. Two photon absorption may lead to the therapeutic benefits of this treatment.

Linkers

In some embodiments, the receptor and/or indicators may be coupled to the nanoparticles by a linker group. A variety of linker groups may be used. The term "linker", as used herein, refers to a molecule that may be used to link a receptor to an indicator; a receptor to a nanoparticle or another linker, or an indicator to a nanoparticle or another linker. A linker is a hetero or homobifunctional molecule that includes two reactive sites capable of forming a covalent linkage with a receptor, indicator, other linker or nanoparticle. The capping agent described herein may function as the linger. Suitable linkers are well known to those of skill in the art and include, but are not limited to, straight or branched-chain carbon linkers, heterocyclic carbon linkers, or peptide linkers. Particularly preferred linkers are capable of forming covalent bonds to amino groups, carboxyl groups, or sulfhydryl groups or hydroxyl groups. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Sulfhydryl-binding linkers include reactive groups such as sulfhydryl groups, acrylates, isothiocyanates, isocyanates and the like. Hydroxyl binding groups include reactive groups such as carboxyl groups, isocyanates, isothiocyanates, esters, haloalkyls, and the like. In certain embodiments, an end of the linker is capable of binding to a crystalline composition formed from a Group IV metal element. The use of some such linkers is described in U.S. Pat. No. 6,037,137 which is incorporated herein by reference.

Biological Circuitry

In some embodiments, the nanoparticles may be coupled to a biological entity. The biological entity may be a cell, a nerve cell or a network of neurons. The biological entity may be a skin cell, or a cell from another part of the body. The cell may be a single cell microorganism, or a mammalian cell. Connecting the nanoparticles to neurons, or other biological entities, may function in the same way as described herein using receptors and/or linkers. However, nanoparticles described herein may be capable of interacting electrically with cells. Nanoparticles may interact electrically with cells to provide stimulation. Upon light absorption, nanoparticles may generate local electric fields, or drive redox reactions at the cell surface, or create local pH gradients, which may affect the cell metabolism or the cell physiology. The local stimulation may induce the production of certain chemical products within the cell. The integration of biological systems and microelectronics offers a completely new strategy for next-generation heterojunction applications, such as neuronal memory devices and prosthetics that control cells directly. By using the appropriate receptor the nanoparticle may be coupled to a specific type of cell or neuron or positioned at specific site on a cell. By using linkers with very short length scales nanoparticles may be coupled to the cell within nanometers of the cell surface. These linkers may be strands of RNA, DNA, short amino acid sequences, polypeptides, fatty acids, proteins, antibodies, or other small molecules. Positioning nanoparticles within close proximity to the cell reduces the deleterious effects of cell membrane counter-ion charge screening. The particles may be coated with molecules that induce the cellular uptake of the nanoparticles. In one embodiment, the nanoparticles might be functionalized with a protein such as transferring to enable cellular uptake. In another embodiment, the nanoparticles may be coated with molecular receptors that direct the placement of the nanoparticles within the cell. Either within the cell, or adsorbed to the surface of the cell, optically activated nanoparticles experience electron-hole separation the nanoparticles may produce electric fields, or the potential to drive local redox reactions, which may affect the viability of the cell, the metabolism, or metabolic products. Electric fields produced by nanoparticles may induce changes in the local cell potential, effectively forming an example of biological circuitry.

Li Batteries

Lithium based batteries generally use electrolytes containing lithium ions. The anodes for these batteries may include lithium metal (lithium batteries), or compositions that intercalate lithium (lithium ion batteries). The compositions that intercalate lithium, for use in the cathodes, generally are chalcogenides such as metal oxides that can incorporate the lithium ions into their lattice.

Figure 11:
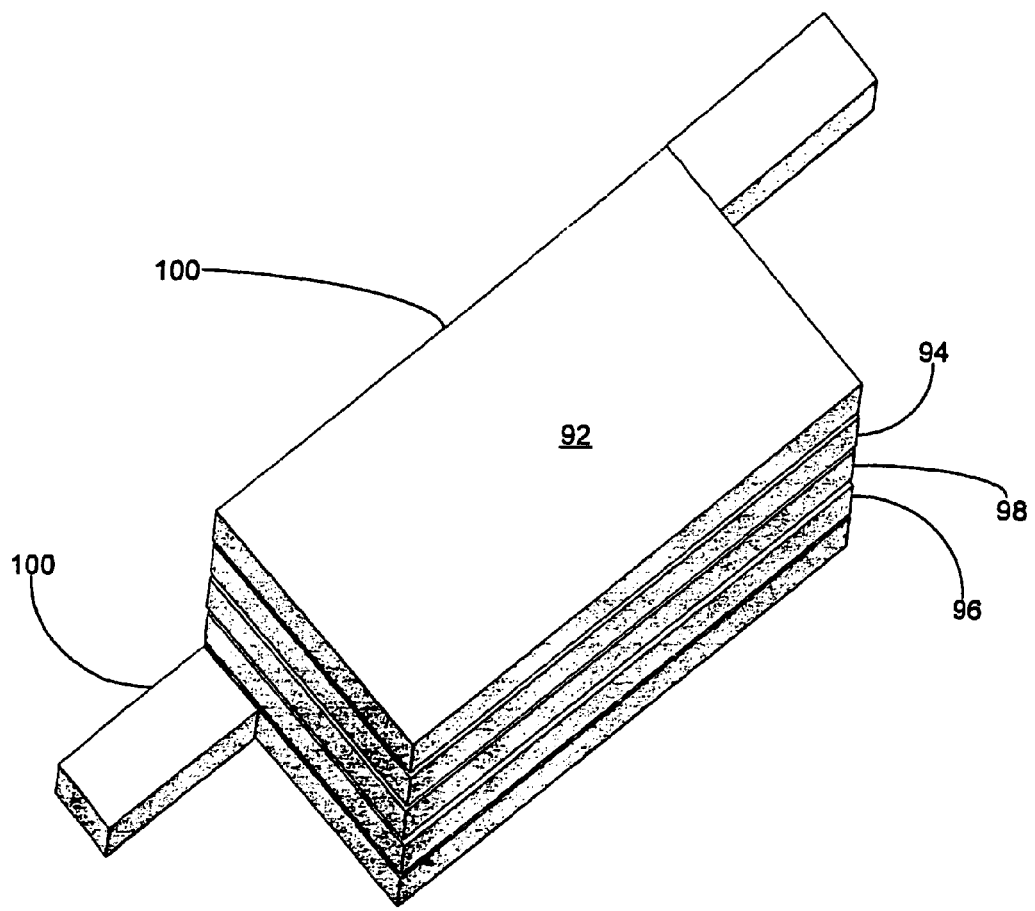
FIG. 11 depicts a schematic of an embodiment of a battery based on the nanoparticles described herein.

FIG. 11 depicts a schematic of an embodiment of a battery based on the nanoparticles described herein. A typical lithium battery 92 includes an anode 94, a cathode 96 and separator 98 between anode 94 and cathode 96. A single battery may include multiple cathodes and/or anodes. Electrolyte can be supplied in a variety of ways as described further below.

Lithium has been used in reduction/oxidation reactions in batteries because they are the lightest metal and because they are the most electropositive metal. Metal oxides are known to incorporate lithium ions into their lattice structure through intercalation or similar mechanisms such as topochemical absorption. Thus, many metal oxides may be effective as an electroactive material for a cathode in either a lithium or lithium ion battery.

Lithium intercalated metal oxides are formed in the battery during discharge. The lithium leaves the lattice upon recharging, i.e., when a voltage is applied to the cell such that electric current flows into the cathode due to the application of an external current to the battery. Intercalation generally is reversible, making metal oxide based lithium batteries suitable for the production of secondary batteries.

In one embodiment, cathode 96 may include electroactive nanoparticles held together with a binder. Any of the nanoparticle described herein may be used in cathode 96 for lithium battery 92. For example, metal oxide nanoparticles produced using the methods described herein may be held together with a binder to produce cathode 96. Nanoparticles for use in cathode 96 generally may have any shape, e.g., roughly spherical nanoparticles or elongated nanoparticles. Cathode 96 may include a mixture of different types of nanoparticles (e.g., vanadium oxide and titanium oxide nanoparticles).

Cathode 96 optionally may include electrically conductive particles in addition to the electroactive nanoparticles. These supplementary, electrically conductive particles generally are also held by the binder. Suitable electrically conductive particles include conductive carbon particles such as carbon black, metal particles such as silver particles and the like. These particles may also be nanoparticles, produced by any of the methods described herein.

High loadings of nanoparticles can be achieved in the binder. Nanoparticles may make up greater than about 80 percent by weight of the cathode, and in some embodiments greater than about 90 percent by weight. The binder may be any of various suitable polymers such as polyvinylidene fluoride, polyethylene oxide, polyethylene, polypropylene, polytetrafluoroethylene, polyacrylates and mixtures and copolymers thereof.

Anode 94 of battery 92 may be constructed from a variety of materials that are suitable for use with lithium ion electrolytes. In the case of lithium batteries 92, anode 94 can include lithium metal or lithium alloy metal either in the form of a foil, grid or metal particles in a binder.

Lithium ion batteries use particles having a composition that may intercalate lithium. The particles may be held with a binder in the anode. Suitable intercalation compounds include, for example, graphite, synthetic graphite, coke, mesocarbons, doped carbons, fullerenes, niobium pentoxide and tin oxide, Lithium batteries may also include collectors 100 that facilitate flow of electricity from the battery. Collectors 100 are electrically conductive and may be made of metal such as nickel, iron, stainless steel, aluminum and copper and may be metal foil or preferably a metal grid. Collector 100 may be on the surface of their associated electrode or embedded within their associated electrode.

Separator 98 is an electrically insulating material that provides for passage of at least some types of ions. Ionic transmission through the separator provides for electrical neutrality in the different sections of the cell. Separator 98 generally prevents electroactive compounds in cathode 96 from contacting electroactive compounds in anode 94.

A variety of materials may be used for separator 98. For example, separator 98 may be formed from glass fibers that form a porous matrix. Alternatively, separators 98 may be formed from polymers such as those suitable for use as binders. Polymer separators may be porous to provide for ionic conduction. Alternatively, polymer separators may be solid electrolytes formed from polymers such as polyethylene oxide. Solid electrolytes incorporate electrolyte into the polymer matrix to provide for ionic conduction without the need for liquid solvent.

Electrolytes for lithium batteries or lithium ion batteries may include any of a variety of lithium salts. In some embodiments, lithium salts have inert anions and are nontoxic. Suitable lithium salts include, but are not limited to, lithium hexafluorophosphate, lithium hexafluoroarsenate, lithium bis(trifluoromethyl sulfonyl imide), lithium trifluoromethane sulfonate, lithium tris(trifluoromethyl sulfonyl) methide, lithium tetrafluoroborate, lithium perchlorate, lithium tetrachloroaluminate, lithium chloride and lithium perfluorobutane.

If a liquid solvent is used to dissolve the electrolyte, the solvent may be inert and may not dissolve the electroactive materials. Generally appropriate solvents include, but are not limited to, propylene carbonate, dimethyl carbonate, diethyl carbonate, 2-methyl tetrahydrofuran, dioxolane, tetrahydrofuran, 1,2-dimethoxyethane, ethylene carbonate, .gamma.-butyrolactone, dimethyl sulfoxide, acetonitrile, formamide, dimethylformamide and nitromethane.

The shape of the battery components may be adjusted to be suitable for the desired final product, for example, a coin battery, a rectangular construction or a cylindrical battery. The battery generally includes a casing with appropriate portions in electrical contact with current collectors and/or electrodes of the battery. If a liquid electrolyte is used, the casing inhibits the leakage of the electrolyte. The casing may help to maintain the battery elements in close proximity to each other to reduce resistance within the battery. A plurality of battery cells may be placed in a single case with the cells connected either in series or in parallel. Further general information regarding the structure and formation of lithium batteries may be found in U.S. Pat. No. 6,130,007 which is incorporated herein by reference.

EXAMPLES

The following examples are included to demonstrate certain embodiments. It should be appreciated by those of skill in the art that the techniques disclosed in the examples which follow represent techniques discovered which function well in the practice of the disclosure herein. However, those of skill in the art should, in light of the present disclosure, appreciate that many changes can be made in the specific embodiments which are disclosed and still obtain a like or similar result without departing from the spirit and scope of the invention.

The following non-limiting examples demonstrate that by using a Si surface-passivating solvent heated and pressurized, the necessary temperatures can be reached to degrade the Si precursor while maintaining solvation of the capping ligand to arrest particle growth. A temperature of 500° C. promotes Si crystallization. In certain embodiments a supercritical (sc) solvent can be used to provide a solvent with a high diffusion coefficient, on the order of $10^{-3}$ to $10^{-4}$ cm$^2$ s$^{-1}$, for rapid reactant diffusion. Supercritical solvents may be used in preparation of narrow particle size distributions, in which the particle growth is diffusion-limited. Using the methods of the invention highly stable Si nanoparticles ranging from approximately 10 to 200 Å in diameter can be produced.

Material and Methods

Diphenylsilane and anhydrous 1-octanol and hexane, packaged under nitrogen, were obtained from Aldrich Chemical Co. (St. Louis, Mo.) and stored in a nitrogen glovebox.

Organic-passivated Si nanoparticles were prepared by thermally degrading diphenylsilane in mixtures of octanol and hexane (octanol:$T_c$=385° C.,$P_c$=34.5 bar, hexane: $T_c$=235° C., $P_c$=30 bar) well above the critical point at 500° C. and 345 bar in an inconnell high-pressure cell. The presence of Si particles was observed by the formation of a yellow solution; no color change was observed in the absence of diphenylsilane. When diphenylsilane was degraded in the presence of sc-ethanol rather than sc-octanol, the solution quickly turned from orange to brown and then clear as polydisperse micron-sized Si particles formed and settled on the walls of the reaction vessel. This result suggests that, unlike ethanol, the bound octanol chains provide sufficient steric stabilization to prevent aggregation. The sc-octanol quenches the reaction and passivates the Si nanoparticle surface.

A typical preparation begins inside a glovebox. Diphenylsilane solution (250-500 mM in octanol) is loaded into an inconnell high-pressure cell (0.2 mL) and sealed under a nitrogen atmosphere. After removing the cell from the glovebox, it is attached via a three-way valve to a stainless steel high-pressure tube (~40 cm$^3$) equipped with a stainless steel piston. Deionized water is pumped into the back of the piston with an HPLC pump (Thermoquest) to inject oxygen-free octanol through an inlet heat exchanger and into the reaction cell to the desired pressure, between 140 and 345 bar. The cell is covered with heating tape (2 ft) and heated to 500° C. (±0.2° C.) within 15-20 min with use of a platinum resistance thermometer and a temperature controller. The reaction proceeds at these conditions for 2 h. Chloroform is used to extract the Si nanoparticles from the cell upon cooling and depressurization. The nanoparticle dispersion is subsequently dried and the organic-stabilized Si nanoparticles are redispersed in hexane or chloroform. The small 15 Å diameter particles also redisperse in ethanol. The larger Si nanoparticles, with slightly broader size distributions, are produced by increasing the Si:octanol mole ratio with hexane as a solvent; a typical Si:octanol mole ratio is 1000:1. The reaction yield in percent conversion of Si precursor to Si incorporated in the nanoparticles varies from 0.5% to 5%.

In another experiment Si nanoparticles were synthesized via thermal degradation of a silicon precursor in supercritical hexane. 1.5 mL of a stock Si precursor solution (250 mM diphenylsilane and 25 mM octanethiol in hexane) was loaded into a 10 mL cylindrical titanium reactor in a nitrogen glove box. All chemicals used for the synthesis were degassed to remove oxygen and stored in a nitrogen rich environment. The titanium reactor was sealed, removed from the glove box, wrapped with high temperature heating tape and heated to 500° C. The reaction proceeded at 500° C. and 83 bar for 30 minutes. The reactor was then allowed to cool to room temperature over the course of approximately 2.5 hours. The product was extracted with chloroform and precipitated in excess ethanol to remove reaction byproducts. The nanoparticles could be redispersed in a variey of organic solvents for further manipulation for later analysis.

A JEOL 2010 transmission electron microscope with 1.7 Å point-to-point resolution operating with a 200 kV accelerating voltage with a GATAN digital photography system was used for transmission electron microscopy. In situ elemental analysis was performed on the nanoparticles with an Oxford energy dispersive spectrometer. Electron diffraction images were obtained with the JEOL 2010 operating at 200 kV. Absorbance spectra were recorded with a Varian Cary 500 UV-Vis-NIR spectrophotometer with Si nanoparticles dispersed in ethanol or hexane. The extinction coefficients, $\epsilon$, were determined for the nanoparticles from the relationship between the measured absorbance (A=$\epsilon$cl), the path length (l=10 cm), and the Si concentration determined from dry weights. The quantity $\epsilon c$ is the absorption coefficient, $\alpha$ Luminescence measurements were performed with a SpeX Fluorolog-3 spectrophotometer. The PL and PLE spectra were corrected with quinine sulfate as a standard. Quantum yields were calculated by comparison with 9,10 diphenylanthracene. FTIR measurements were obtained with a Perkin-Elmer Spectrum 2000 FTIR spectrometer. FTIR spectra were acquired from dried films of silicon nanoparticles deposited on Zinc Selenide windows.

Example 1

Transmission Electron Microscopy

A TEM image of an organic-monolayer stabilized 40 Å diameter Si nanoparticle exhibits a crystalline core with a well-defined faceted surface. The lattice spacing was 3.1 Å, characteristic of the distance separating the (111) planes in diamond-like Si. Si nanoparticle may propagate through a radical mechanism as shown:

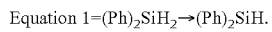

Equation 1=$(Ph)_2SiH_2 \rightarrow (Ph)_2SiH$.

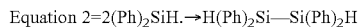

Equation 2=$2(Ph)_2SiH. \rightarrow H(Ph)_2Si—Si(Ph)_2H$

The benzene rings may help stabilize the diphenylsilane radical intermediates by delocalizing the electron charge. These free radicals can react to form Si—Si bonds. The octanol molecules subsequently displace the phenyl groups and cap the Si particle surface. There are other possible mechanisms that include the formation and degradation of other intermediate products, such as triphenyl and tetraphenyl silane. Furthermore, this reaction may not proceed through a free radical mechanism.

Example 2

Extraction of Silicon Nanoparticles

Size-monodisperse 15 Å diameter Si nanoparticles were obtained by reacting diphenylsilane in pure octanol with subsequent redispersion in ethanol. A fraction of the sample is made up of larger Si nanoparticles that form during the reaction that do not resuspend in ethanol due to their hydrophobicity, whereas the extreme surface curvature of the 15 Å diameter nanoparticles provides ethanol with "access" to the polar Si—O—C capping layer termination to enable the size-selective dispersion of 15 Å diameter Si nanoparticles. The 15 Å diameter nanoparticles are barely perceptible in TEM images obtained with samples dispersed on a carbon-coated TEM grid. Low-resolution images of aggregates of these 15 Å diameter nanoparticles show that the samples contain little size variation. For comparison, TEM images of larger Si nanoparticles with diameters ranging from 25 to 35 Å produced by performing the synthesis in sc-hexane with increased Si:octanol mole ratios clearly reveal highly crystalline cores and faceted surfaces. Crystalline lattice planes are observed in nanoparticles as small as 25 Å. Electron diffraction from these nanoparticles also confirmed that the nanoparticles consist of crystalline Si cores with diamond lattice structure.

A variety of other techniques were used to characterize the Si nanoparticles, including, Fourier transform infrared spectroscopy (FTIR), UV-vis absorbance, and PL and PLE spectroscopy.

Example 3

In Situ Energy-Dispersive X-ray Spectroscopy

In situ energy-dispersive X-ray spectroscopy (EDS) measurements of the nanoparticles imaged by TEM revealed Si in high abundance with the presence of oxygen and carbon as well. A quantitative analysis of the elemental ratios was not possible since the supporting substrate was carbon containing a measurable amount of residual oxygen.

Figure 12:
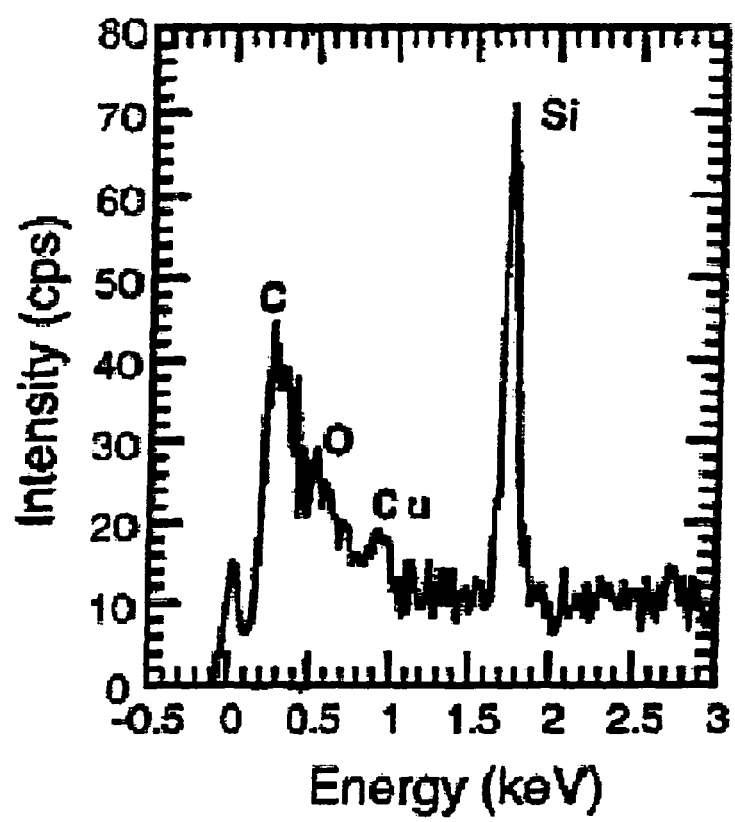
FIG. 12 depicts an example of energy-dispersive X-ray spectroscopy analysis of an exemplary nanoparticle composition.

FIG. 12 illustrates an example of energy-dispersive X-ray spectroscopy (EDS) analysis of an exemplary nanoparticle composition. The EDS data of the exemplary nanoparticle. The copper (Cu) peak results from the copper TEM grid used as a support. Other peaks shown are the carbon (C), oxygen (O) and silicon (Si) peak Example 4

X-ray Photoelectron Spectroscopy

X-ray photoelectron spectroscopy (XPS), however, provides an elemental analysis of the particles which gives an indication of how the nanoparticles are capped with the organic ligands. XPS data for 15 Å diameter Si nanoparticles, which reveals that the sample contains a Si:C ratio of 0.70:1.

Figure 13:
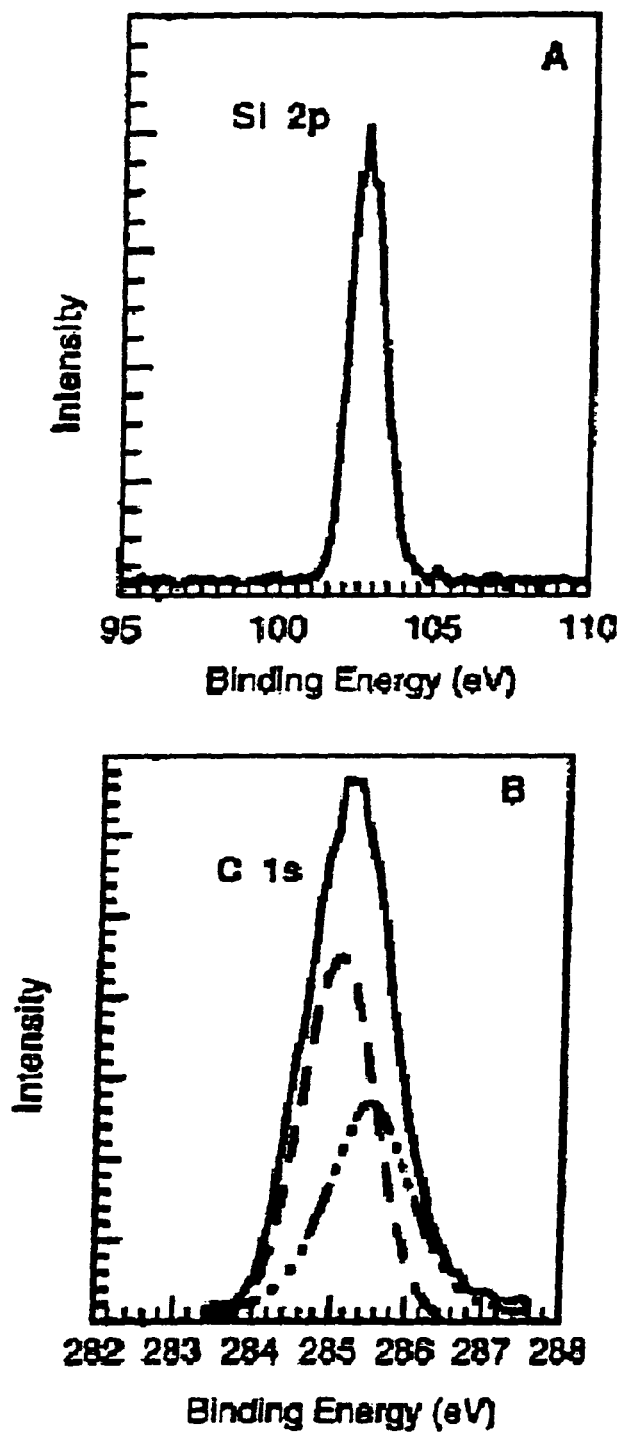
FIG. 13 depicts an example of X-ray Photoelectron spectroscopy analysis of an exemplary nanoparticle composition.

By using a shell approximation, $d_p = a_{si}(3N_{si}/4\pi)^{1/3}$, where $a_{si}$ is the lattice constant (5.43 Å), the number of Si atoms, $N_{si}$, in a nanoparticle can be calculated. Particles with 15 Å diameter ($d_p$) have approximately 88 atoms. The Si:C ratio determined from XPS can be used to calculate approximately the area occupied on the nanoparticle surface by each capping ligand. With the Si:C ratio equal to 0.7, the 15 Å cluster with 88 core Si atoms has 125 C atoms surrounding it. Each ligand has 8 carbons. Therefore, each particle is surrounded by approximately 16 capping ligands. Dividing the particle surface area by 156 indicates that each ligand occupies an average of 44 Å$^2$. This value is about twice that expected for a close-packed monolayer of ligands surrounding the nanoparticles. Therefore, XPS indicates that the ligands coat the nanoparticles with approximately 50% surface coverage. An estimate of the surface coverage of the largest 20 Å diameter nanoparticles in the sample size distribution gives an area per molecule of 33 Å$^2$, for approximately 70% surface coverage. FIG. 13A and FIG. 13B illustrate examples of X-ray Photoelectron spectroscopy (XPS) analysis of an exemplary nanoparticle composition. In particular, XPS of an exemplary 15 Å diameter silicon nanoparticles deposited on a graphite substrate. (A) Si 2p region in the spectrum (modified area is 592.2 counts) and (B) Carbon 1s region (single line) and its deconvoluted peaks from the graphite substrate (dashed line) and the capping ligand (dotted and dashed line). The modified area of the C 1s curve due to the capping ligand is 850.5 counts. The silicon-to-carbon ratio (Si:C) for this particular example is 0.70:1.

Example 5

Fourier Transformed Infra-Red Spectroscopy

FTIR spectra show that the nanoparticles are most likely terminated with a combination of hydrogen and hydrocarbon chains, bound through an alkoxide (Si—O—C) linkage. Four characteristic methylene and terminal methyl stretching modes $v_{a(CH2)}=2928$ cm$^{-1}$, $v_{a(CH2)}$-2855 cm$^{-1}$, $v_a(CH_3jp)=$ 2954.5 cm$^{-1}$, $v_a(CH_2FR)=2871$ cm$^{-1}$, reveal that a hydrocarbon steric layer has indeed adsorbed to the particle surface. The notable absence of the hydroxyl stretch ($v_{(O—H)}=3300$ cm$^{-1}$) and the presence of the strong doublet corresponding to the Si—O—CH$_2$— stretching modes, $v_{(Si-O-CH2-)}=1100$-1070 cm$^{-1}$, suggests covalent alkoxide bonding to the Si nanoparticle surface. Siloxane Si—O—Si stretches typically occur at slightly lower wavenumber (1085 and 1020 cm$^{-1}$); however, the presence of residual oxide on the nanoparticle surfaces cannot be completely excluded based on these data alone. The absence of the very strong characteristic aryl-Si stretching mode, at $v_{(Si-Ph)}=1125$-1090 cm$^{-1}$, confirms precursor degradation. The lack of the strong $v_{(Si-C-Si)}=1080$-1040 cm$^{-1}$ stretching mode eliminates the possibility that the Nanoparticles consist of a Si—C core, or that the alkane layer is directly adsorbed to the Si surface. Strong Si TO (transverse optical) phonon bands occur between 450 and 520 cm$^{-1}$, indicating that the particles are composed of Si only. Strong peaks between 750 and 850 cm$^{-1}$ can possibly be assigned to a variety of Si—H stretching modes. There is also a possible carbonyl stretch at $v\_1700$ cm$^{-1}$ that could result from octanol adsorption through a Si—C=O linkage if alcohol oxidation to the aldehyde occurs. On the basis of XPS and FTIR data, the nanoparticle surface is coated mostly by the hydrocarbon ligands. However, the remaining 30% to 50% of the surface is coated with a combination of hydrogen, Si—C=O, and possibly a small portion of oxide.

Figure 14:
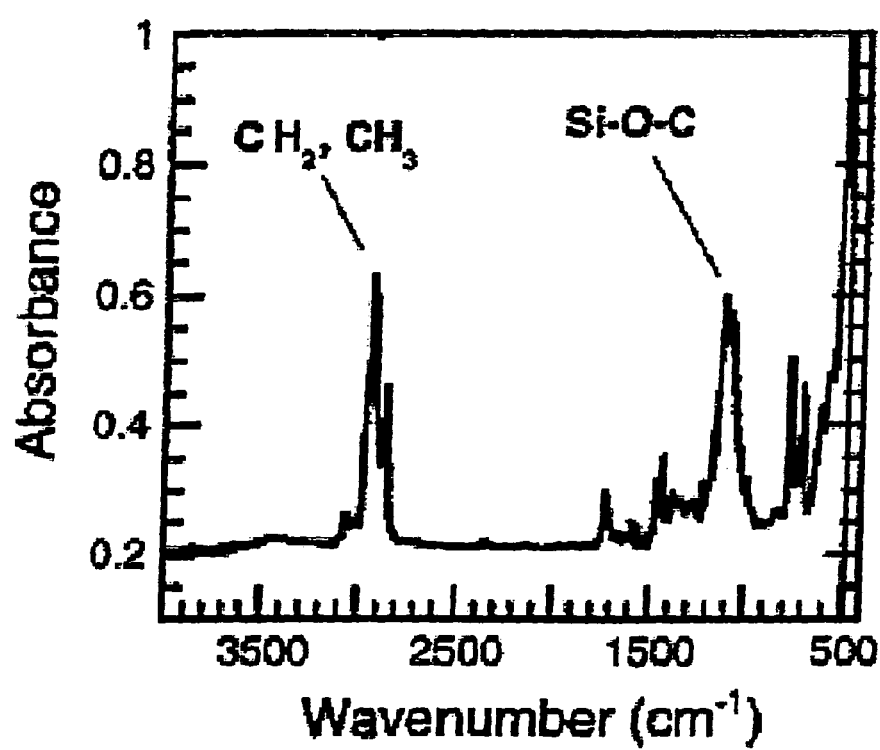
FIG. 14 depicts an example of Fourier transformed infrared spectroscopy analysis of an exemplary nanoparticle composition.

FIG. 14 illustrates an example of Fourier transformed infrared spectroscopy (FTIR) analysis of an exemplary nanoparticle composition. The spectrum reveals that the sterically stabilizing hydrocarbon chains are covalently linked to the Si surface through alkoxide linkages. These covalent linkages give rise to highly stable optical properties in the presence of ambient oxygen and water.

Example 6

Optical Properties

The Si nanoparticles photoluminesce with overall quantum yields as high as 23% at room temperature. Several closely spaced discrete features appear in the PLE spectra of the 15 Å diameter nanoparticles, which are mirrored by a few meV in the absorbance spectra. The nanoparticles exhibit size-dependent PL and PLE spectra, with the smaller nanoparticles (approximately 15 Å diameter) emitting in the near-UV and the larger nanoparticles (approximately 25 to 40 Å diameter) emitting green light. For all sizes, the absorption coefficient α was found to increase quadratically with incident energy, $\alpha \sim [hv-E_2]^2$, near the absorption edge, which is characteristic of a predominantly indirect transition. Comparison of the extinction coefficients for bulk Si with those measured for the 15 Å diameter nanoparticles. The indirect Γ→X transition remains the lowest energy transition, increasing from 1.2 eV (bulk Si) to 1.9 eV due to quantum confinement. It should be noted that it appears that the direct Γ→Γ transition has red shifted to 3.2 eV from 3.4 eV and the L→L transition energy has blue-shifted from 4.4 eV to 4.7 eV, in quantitative agreement with empirical pseudopotential calculations by Ramakrishna and Friesner, although these assignments cannot be made conclusively. Further comparison of the extinction coefficients measured for the nanoparticles with values for bulk Si reveals an overall lifting of the critical point degeneracies (direct transitions at k=0 and away from k=0), as predicted by both empirical pseudopotential and tight-binding calculations, and an oscillator strength enhancement. These results contrast the spectra for slightly larger, more polydisperse Si nanoparticles, ranging in size from 25 to 40 Å in diameter, which exhibit monotonically increasing featureless absorbance spectra. A slight exciton peak, however, does seem to appear in the PLE spectra for the larger nanoparticles at 2.6 eV (470 nm).

The Si nanoparticle PL was remarkably stable in the presence of atmospheric oxygen, especially when considering the sensitivity of the optical properties of porous-Si to surface chemistry, such as oxidation. The sc-technique provides Si nanoparticles with sufficiently robust surface passivation to prevent strong interactions between the Si cores and the surrounding solvent to enable efficient luminescence from Si. Comparison between the PL and PLE spectra reveals a Stokes shift of approximately 100 meV with respect to the lowest energy peak in the PLE spectra. The relatively broad PL peak has a characteristic lifetime of 2 ns, indicating that various nonradiative processes are important in the nanoparticles. It is worth noting that the low-energy PL peak observed by Brus et al. for ~20 Å diameter oxide-coated Si nanoparticles at 1.6 eV was not observed in any of these samples.

Figure 15:
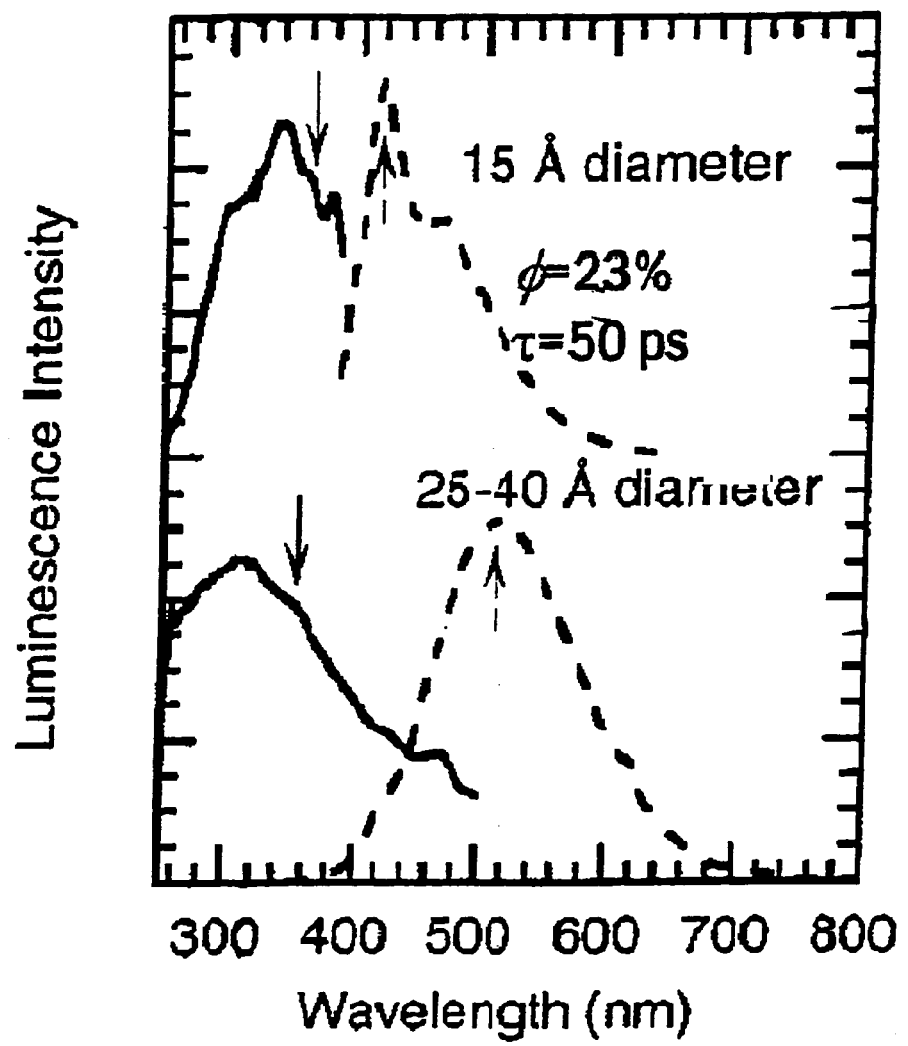
FIG. 15 depicts an example of photoluminescence (PL) and photoluminescence excitation (PLE) spectral analysis of exemplary nanoparticle compositions.

FIG. 15 illustrates an example of photoluminescence (PL) and photoluminescence excitation (PLE) spectral analysis of exemplary nanoparticle compositions. Room temperature PL are depicted as solid lines with the excitation energy marked by a solid arrow and PLE are depicted as dashed lines with the detection energy marked by dashed arrows. The spectra of exemplary 15 Å nanoparticles are compared with spectra of slightly larger particles with a broader size distribution.

Figure 16:
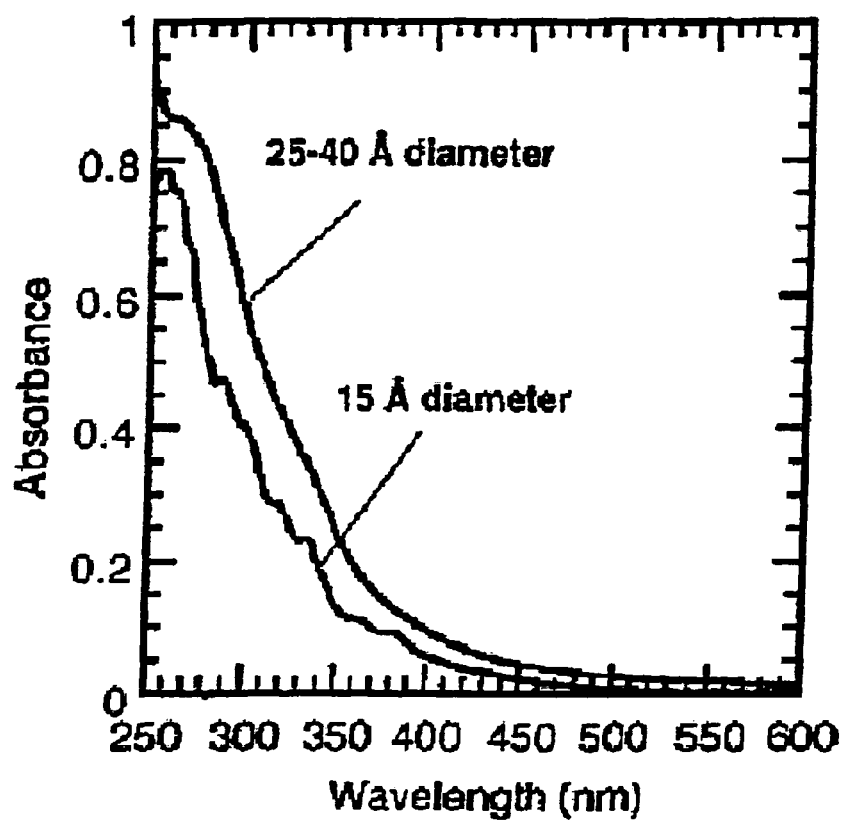
FIG. 16 depicts an example of an absorbance profile of exemplary nanoparticle compositions.

FIG. 16 illustrates an example of an absorbance profile of exemplary nanoparticle compositions. The absorbance spectra were insensitive to solvent polarity, indicating that the absorbance is due to an exciton state and not a charge-transfer transition between bound ligands. Mote the blue shift in the absorbance edge, and the appearance of discrete optical transitions in the spectra of exemplary 15 Å nanoparticles compared to the larger, more polydisperse nanoparticles.

Figure 17:
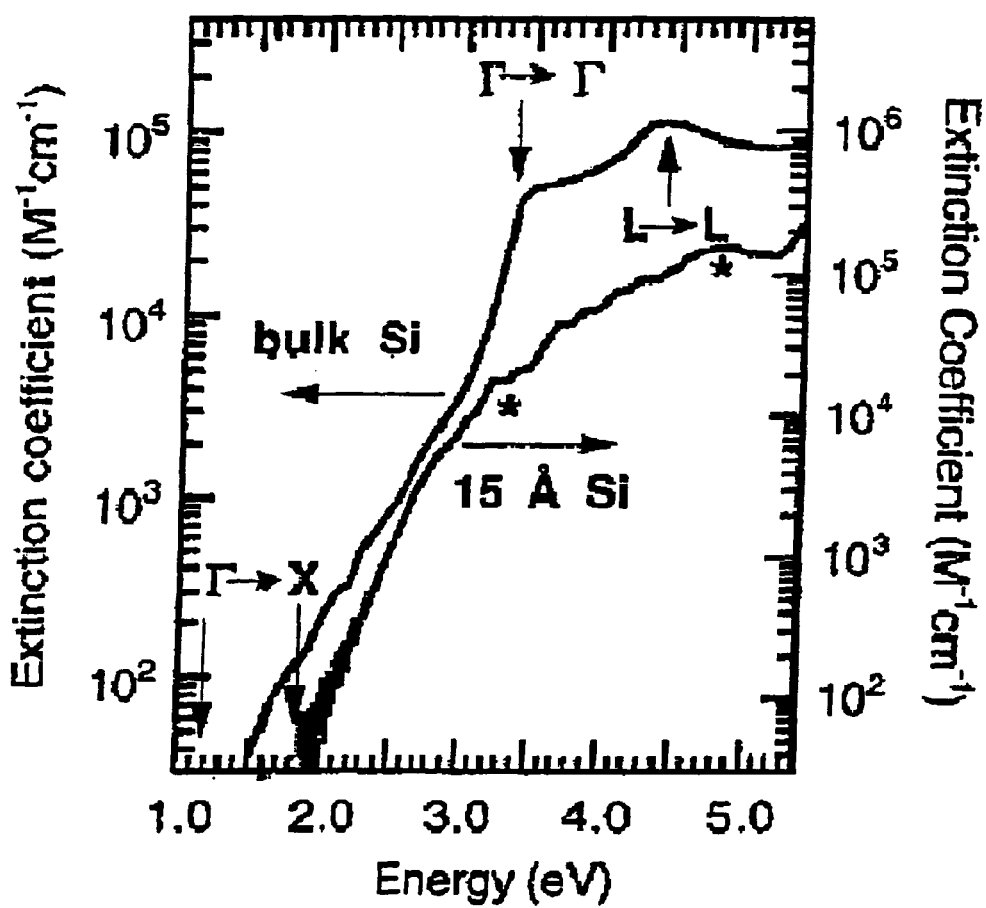
FIG. 17 depicts a comparison between the extinction coefficients of bulk silicon as compared to the extinction coefficient of an exemplary nanoparticle composition.

FIG. 17 illustrates a comparison between the extinction coefficients of bulk silicon as compared to the extinction coefficient of an exemplary nanoparticle composition. The absorption edge corresponds to the indirect Γ to X transition and the two peaks in the bulk Si spectra correspond to the Γ to Γ and L to L critical points at 3.4 and 4.3 eV, respectively. Note the apparent blue shift of the Γ to X and L to L transitions in the nanoparticles due to quantum confinement and the apparent red shift of the Γ to Γ transition, as predicted by Ramakrishna and Friesner, 1992.

Figure 21:
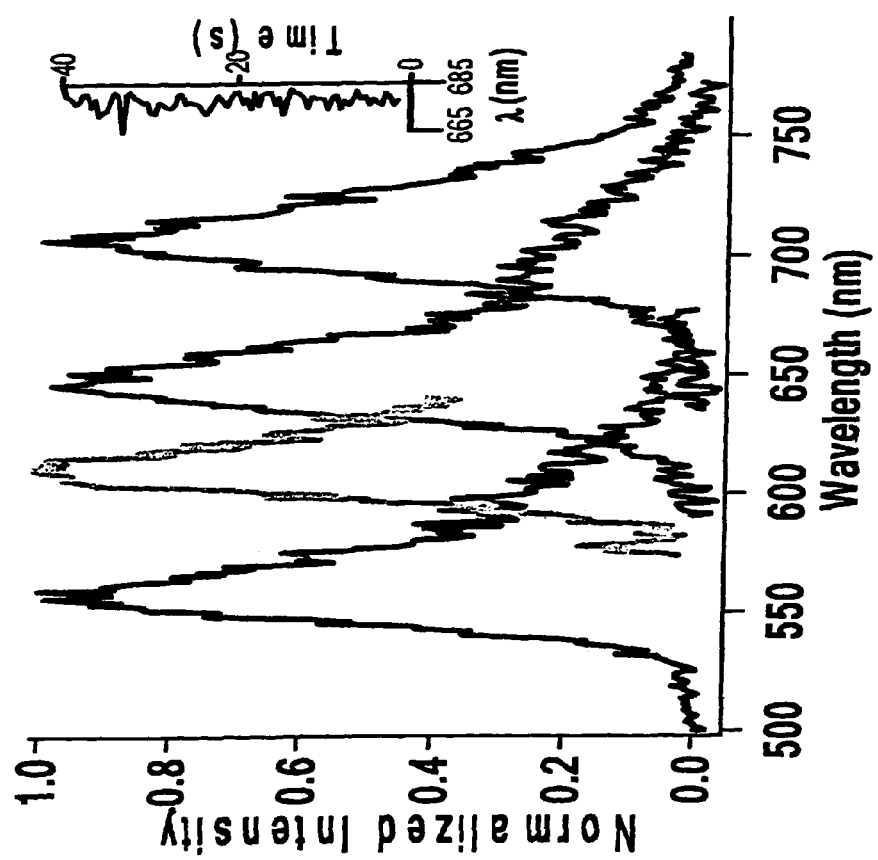
FIG. 21 depicts examples of single dot PL spectra.

FIG. 21 illustrates four single dot PL spectra of four different nanoparticles at room temperature, showing the narrow line widths. The peak widths are very sharp compared to previously studied nanocrystalline silicon. Inset: Mean spectral trajectory of a single particle showing that spectral diffusion is not observable within the experimental accuracy of the instrumentation The origin of the photoluminescence in Si nanoparticles is quite complex and remains actively debated. The PL spectrum is clearly size dependent, with the larger particles emitting lower energy light than the smaller particles, consistent with the general perception of quantum confinement effects in Si. The PL from Si nanoparticles, however, has been shown to be highly sensitive to surface chemistry, especially the presence of oxide on the nanoparticle surface. Indeed, the PL spectrum of the 15 Å diameter nanoparticles is complicated by the presence of two prominent peaks in the 15 Å nanoparticle spectrum: one at 2.95 eV (419 nm) and one at 2.65 eV (467 nm). Furthermore, the PL was found to depend on the excitation wavelength, with 3.4 eV (363 nm) excitation yielding the highest quantum yield and the sharpest PL. Increasing the excitation energy from 3.4 eV to 4.4 eV (281 nm) led to a decrease in the intensity of the highest energy feature with respect to the low-energy "satellite" peak, and a decrease in the overall quantum yield. Although the peaks cannot be assigned conclusively at this time, it can be proposed that the higher energy peak is intrinsic to quantum confinement in Si nanoparticles and the lower energy peak results from the presence of oxygen on the particle surface. Calculation of the PL energy due to intrinsic quantum confinement in Si can in some cases differ from the PL energy due to surface states, specifically Si=O. For nanoparticles greater than 3 nm in diameter, the intrinsic and surface state emission energies are the same, with emission at 2 eV (620 nm). However, 15 Å diameter nanoparticles were predicted to give rise to intrinsic PL at 2.8 eV, and surface state PL resulting from the presence of oxygen at 2.3 eV (537 nm). The PL spectra of the Si nanoparticles are consistent with this interpretation. It should be noted, however, that peak splitting due to separate direct and phonon-assisted absorption and emission events has been observed for porous Si and may provide an alternative explanation.

Example 7

Single Dot Spectroscopy Methods

Single dot spectroscopy measurements were conducted using a confocal optical microscope in an epi-illumination configuration. Samples consist of Si nanoparticles dispersed on a glass coverslip by spin coating very dilute nanoparticle suspension in chloroform. The excitation laser beam from an Ar+ laser was focused by an oil immersion objective (1.2 NA) to a diffraction limited spot on the sample coverslip. A computer-controlled piezo stage scans the sample. The sample photoluminescence was collected through the same objective, filtered with a holographic notch filter to remove residual excitation light, and detected by an avalanche photodiode (APD). Alternatively, the emission spectra are obtained by directing the light output to a polychromator equipped with an intensified charged-coupled device (ICCD) to record the intensity as a function of wavelength.

Figure 24:
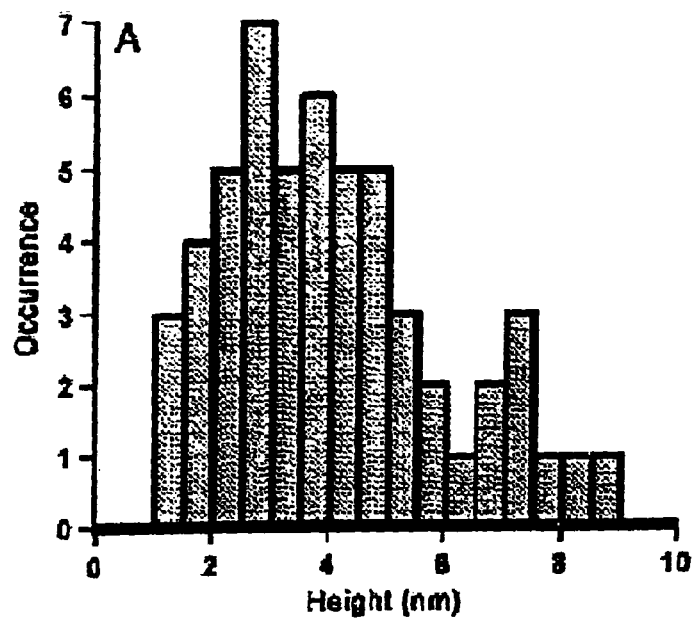
FIG. 24 depicts an example of an atomic force microscopy (AFM) histogram showing a silicon nanoparticle height distribution.
Figure 25:
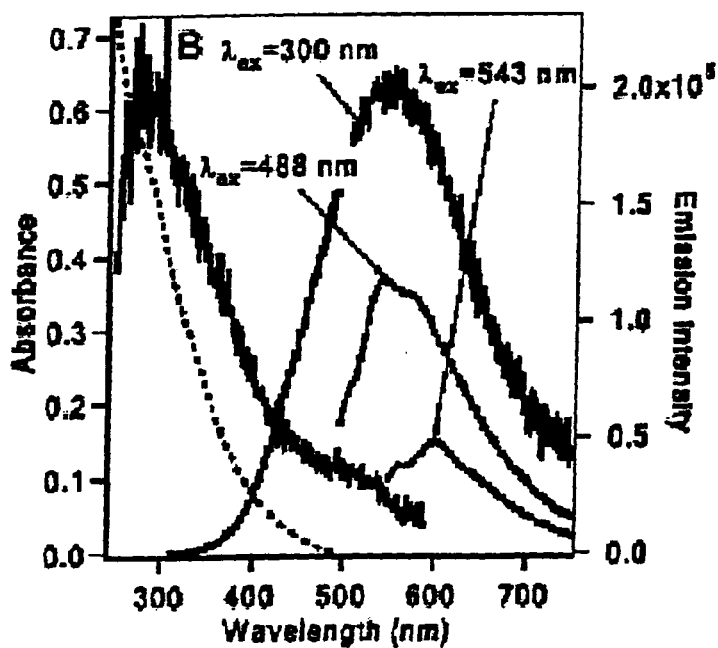
FIG. 25 depicts an example of room temperature absorbance, PLE and PL spectra for silicon nanoparticles.

In order to obtain PL spectra from individual Si nanoparticles with a range of sizes in a single experiment, octanethiol-coated Si nanoparticles were synthesized with a broad size distribution, having an average diameter of 4.65±1.36 nm as determined by TEM (based on 361 dots) and 4.35±2.02 nm determined by AFM height profiles of the sample (FIG. 24). The PL spectra obtained from the nanoparticles dispersed in chloroform were correspondingly broad. For example, the PL peak shown in FIG. 25 shifts as a function of excitation wavelength largely due to the broad size distribution of the sample. At longer excitation wavelengths, only the larger nanoparticles with lower HOMO-LUMO energies are excited and the emission peak shifts to longer wavelengths. The absorbance spectra and the photoluminescence excitation (PLE) spectra are featureless, due in part to the indirect nature of the Si band gap, but primarily due to the broad size distribution of the nanoparticles. At the single particle level, however, the PL spectra is narrow, exhibiting peaks with FWHM of 1596+/−502 cm$^{-1}$ (~200 meV) (See FIG. 21).

Figure 26:
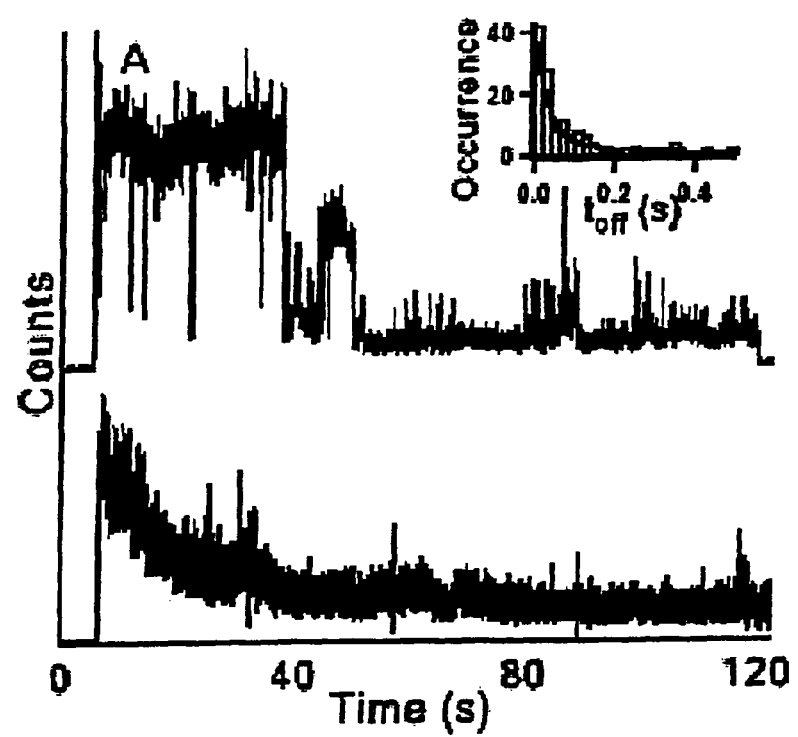
FIG. 26 depicts an example of blinking—a comparison between the blinking of a single dot (top) and the blinking of a cluster (bottom); inset shows a histogram of the "off" times for the single dot blinking.

As has been found for many single molecule systems, and other nanoparticles such as CdSe and InP, the Si nanoparticles exhibit fluorescence intermittency, or "blinking", with a stochastic switching on and off of the PL signal. Although the mechanism for blinking in nanoparticles is not known, the "on" state can be viewed as an optically coupled ground and excited state, whereas the "off" state is aseptically "dark" state. The emission from a cluster of particles exhibited intensity blinking against a gradually decaying background signal as shown in FIG. 26. One obvious test therefore involved the inspection of the time-resolved spectra for a gradually decaying background signal. In cases with few particles, a decaying background did not appear; however, the blinking behavior exhibited multiple intensity steps. In the single particle case, the blinking spectra clearly exhibited monotonic time-dependent PL intensities. As a secondary indicator, the PL peak energy fluctuation was examined. When multiple particles produced the emission, the spectra fluctuated in energy as different sized particles blinked on and off. Therefore, the blinking behavior and peak fluctuation were used to rigorously determine if the measured spectra were truly a result of individual nanoparticles (See FIG. 27 through FIG. 29).

The spectral line widths of the single Si dot PL were as narrow as 150 meV. Although three times broader than the room temperature line widths measured for single CdSe nanoparticles, these linewidths represent the narrowest measured to dat for Si nanostructures. The four peaks shown in FIG. 21 represent typical narrow spectra measured from octanethiol capped Si nanoparticles. Spectra determined to originate from individual nanoparticles did not show measurable spectal diffusion (FIG. 21 inset), suggesting that these organiocapped Si nanoparticles are stable against degradation in air. With excitation at 488 nm, the emission peak maxima shift through the visible, from ~525 nm up to ~700 nm. Due to experimental constraints, excitation wavelengths shorter than 488 nm were not accessible, however, the ensemble spectra clearly show that blue emission results from particles on the small end of the size distribution. Silicon can be made to emit visible light across all frequencies in the visible spectrum by tuning the particle size. This is rather remarkable, given that the bulk band gap of Si is in the near-IR at 1.1 eV.

Figure 27:
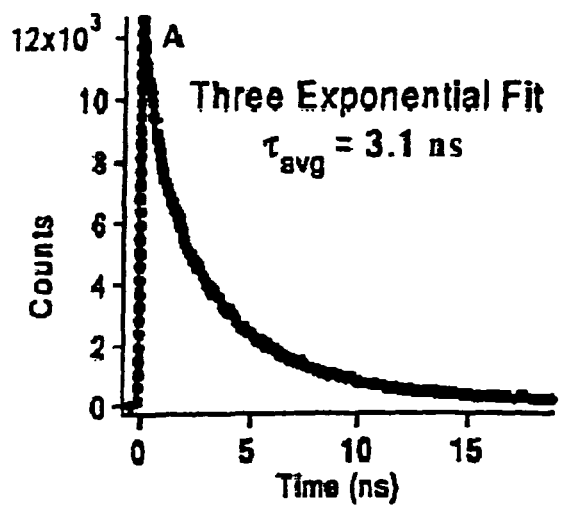
FIG. 27 depicts an example of an average room temperature lifetime measurement of the ensemble.

In order to gain a better understanding of the nature of the light emitting state in these organic-monolayer passivated nanoparticles, PL lifetimes were measured and the radiative rate was determined. 17 Microsecond scale PL lifetime, observed previously in por-Si and oxide capped Si nanoparticles, was not detected in our sample. Instead, it is estimated that 98±2% of the total PL exhibit a lifetime of less than or equal to 20 ns. FIG. 27 shows the time-resolved decay of the PL of the Si nanoparticles dispersed in chloroform. It was necessary to implement three exponentials to fit the data: $I(t) = A_1 e^{-t/\tau_1} + A_2 e^{-t/\tau_2} + A_3 e^{-t/\tau_3}$, where $I(t)$ is the measured PL intensity as a function of time, t, after the excitation pulse. Table I (See FIG. 30) lists the fitted constants, $A_1, A_2, A_3, \tau_1, \tau_2, \tau_3$, as a function of detection wavelength. The octanethiol-capped Si nanoparticles examined here exhibit characteristic lifetimes with a fast component (~100 ps), and two slow components with lifetimes ranging from 2 to 6 ns—at least three orders of magnitude faster than those previously found for por-Si and Si nanoparticles. Although the lifetimes of por-Si are characteristically orders of magnitude shorter than those of bulk Si—giving rise to relatively efficient PL—they are nonetheless characteristic of an indirect bandgap transition.

Figure 28:
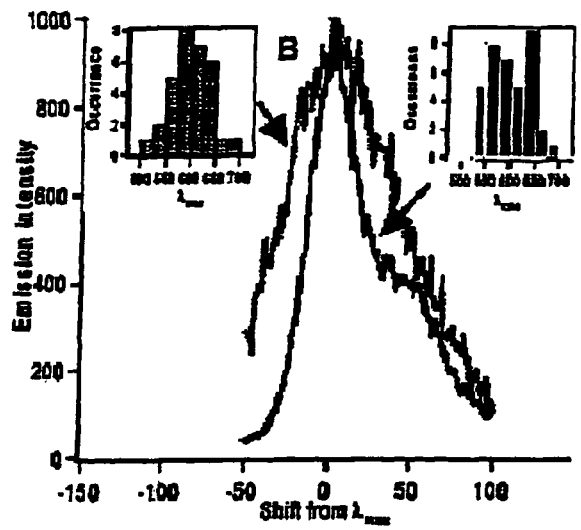
FIG. 28 depicts an example of an observation of "molecular" (——) and "continuum" (----) like single nanocrystal spectra Average of 37 molecular type spectra and 31 continuum type spectra from single nanoparticles excited at 488 nm. Each spectra was shifted so that its maximum was at zero before averaging. Histogram insets of spectral maxima (ëmax) of continuum type and molecular type spectra, respectively.

FIG. 28 depicts an example of an observation of "molecular" (——) and "continuum" (----) like single nanocrystal spectra Average of 37 molecular type spectra and 31 continuum type spectra from single nanoparticles excited at 488 nm. Each spectra was shifted so that its maximum was at zero before averaging. Histogram insets of spectral maxima ($\lambda_{max}$) of continuum type and molecular type spectra, respectively.

Figure 29:
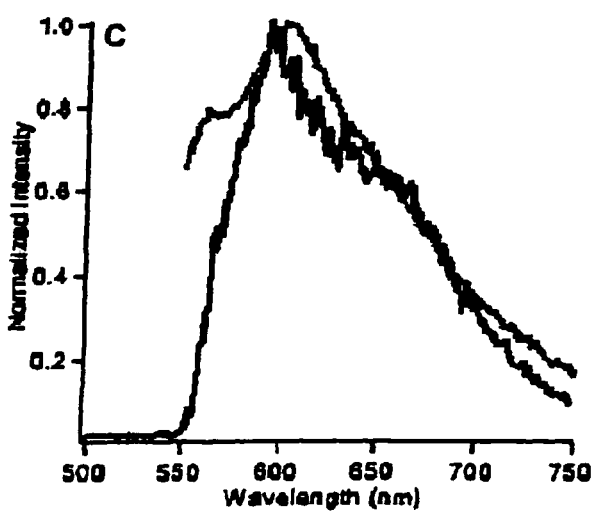
FIG. 29 depicts an example of a comparison of the measured ensemble spectra (——) to the reconstructed ensemble spectra. reconstructed from the single dot spectra (——) of 68 individual silicon nanoparticles.

FIG. 29 depicts an example of a comparison of the measured ensemble spectra (----) to the reconstructed ensemble spectra. reconstructed from the single dot spectra (——) of 68 individual silicon nanoparticles. As a last check to ensure that the single nanocrystal spectra presented in this study indeed represent the ensemble, the PL spectrum was reconstructed from the histogram of PL peak intensity and position of individual nanoparticles. The ensemble spectra appear very similar to the reconstructed spectra, as shown in FIG. 29.

Example 8

Fluorescence Decay and Fluorescence Quantum Yield Measurements

Fluorescence decays were obtained by time-correlated single photon counting (TCSPC) with 488-nm with vertically polarized excitation pulses ($\Delta t \sim 200$ fs, repetition rate 3.8 MHz) from a mode-locked Ti:sapphire laser system (Coherent Mira 900, Coherent Pulse Picker Model 9200, Inrad SHG/THG model 5-050). Emission was collected at 90° with respect to the incident excitation axis through a Glan-Taylor polarizer set at the 'magic angle' of 54.7°. Long pass filters and/or narrow band interference filters were used to block scattered laser light Detection electronics included a microchannel plate detector (Hamamatsu R3809U-50), constant fraction discriminators (Tennelec TC454), time-to-amplitude converter (Tennelec TC864), and multichannel analyzer (Ortec TRUMP MCB). The emission wavelength was selected using 10 nm-width bandpass filters. The emission decay curves were evaluated by an iterative nonlinear least squares fitting procedure. The decay data was fit to a sum of exponential decays convoluted with the instrument response (~50 ps FW. The quality of the fit was evaluated by the reduced $\chi^2$.

The fluorescence quantum yield of Si nanoparticles dispersed in chloroform was measured relative to Rhodamine 6G in ethanol (QY=95%) using 488 nm excitation on a fluorometer (SPEX) in a right-angle geometry. The absorbance of both Si suspension and R6G solution at 488 nm were adjusted to ~0.06. The fluorescence spectra were corrected for detector response.

Example 9

Formation of Sensing Elements/Analyte Complexes

Synthesis of CdS Quantum Dots (and Peptide Coated CdS Dots): Dots were synthesized using previously published methods [H. M. Chen, X. F. Huang, L. Xu, J. Xu, K. J. Chen, D. Feng, Superlattices Microstruct. 2000, 27, 1.]. Briefly, carboxyl-stabilized CdS nanoparticles were synthesized by arrested precipitation at room temperature in an aqueous solution using mercaptoacetic acid as the colloidal stabilizer. All chemicals were used as obtained from Sigma Chemical Co. (St Louis, Mo.). Nanoparticles were prepared from a stirred solution of 0.036 g CdCl2 (1 mM) in 40 mL of pure water. The pH was lowered to 2 with mercaptoacetic acid, and then raised to 7 with concentrated NaOH. Then, 40 mL of 5 mM $Na_2$—$S.9H_2O$ (0.023 g) was added to the mixture. The solution turned yellow shortly after sulfide addition due to CdS nanoparticle formation. For peptide coated dots, peptide (0.041 mg/mL final solution) was added to the solution until dissolved in the initial step (with the $CdCl_2$). Additional peptide densities were not tested, but will be the focus of future studies aimed at improving binding between the cell and the qdots.

CdS Morbidity Studies: SK-N—SH neuroblastoma cells (American Type Culture Collection #HTB-11) were incubated with CdS dots at concentrations of $3 \times 10^{-11}$, $1.5 \times 10^{-11}$, and $0.75 \times 10^{-11}$ M in Dulbecco's minimum essential medium (DMEM) cell culture medium (Sigma). These concentrations reflect multiples of the relative number of qdots added to the cells in the attachment procedure, up to ten times in excess. After adjustment to biocompatible salt concentrations (9 g/L), cell death did not occur with CdS qdot addition. Cells were studied for five days for proliferation and attachment. No differences from controls were observed.

Conjugation of Quantum Dots to IgG Antibody: Goat IgG antibody (Jackson Immunochemistry) was covalently linked to CdS qdots at the carboxyl terminus of the qdot capping ligands. Antibody was added to MES (2-N-morpholino) ethanesulfonic acid, Sigma) 50 mM buffer at a concentration of 0.3 mg/mL. Then, an equal volume of 1.2 µM (80 mL batch diluted to 480 mL) qdots was added to the solution. After a 15 min incubation period, EDAC (1-ethyl-3-(3-dimethylaminopropyl)-carbodiimide hydrochloride, Sigma) was added at 4 mg/mL. Next, the pH was adjusted to pH6.5±0.2. Following 2 h in an orbital shaker, the reaction was quenched using glycine at 7.5 mg/mL. Conjugated qdots were isolated via repeated centrifugation (3000 g) and stored in phosphate buffered saline (PBS) at pH7.4. Control experiments exposing qdots to antibody without EDAC revealed noticeable physisorption of IgG on qdots, as evidenced by pellet formation during centrifugation. However, absorbance measurements of these nanoparticles revealed substantially less IgG binding than in the presence of EDAC. Raising the pH above 6.5, the physisorbed antibody dissociated from the nanoparticles. Therefore, prior to all nerve cell labeling experiments, the nanoparticles were transferred to 1 mL of PBS (pH 7.4). As a result of the crosslinking chemistry in the qdot±antibody conjugation step, some agglomeration of particles occurred; however, the aggregates were small enough to remain suspended in solution.

Attachment of Quantum Dot-Complexes to Cells: Qdot-complexes were attached to cells using standard immunocytology techniques [M. C. Willingham, in Methods in Molecular Biology, Vol. 115, Immunocytochemical Methods and Protocols (Ed: L. C. Javois), Humana Press, Totowa, N.J. 1999, Ch. 16.]. Briefly, cells were placed on 22×22 mm no. 1 thickness coverslips using imaging chambers (Sigma) to retain fluid. Cells were cultured in DMEM media (Sigma) at 37° C. and 5% $CO_2$ in sterile conditions. After the cells attained ~70% confluency, cells were washed with 10 mM PBS (pH 7.4) five times. Then, the cells were blocked with 5% bovine serum albumin (BSA) in PBS (BSA±PBS) for 30 min at 4° C. Following blocking, cells were washed five times in PBS. For antibody attachment, primary antibody was added at 10 lg/mL in BSA±PBS and incubated for 30 min at 4° C. Cells were then washed five times with PBS. Then, antibody-qdot conjugate was added to cells to fill the imaging chamber (~0.25 mL/chamber). Cells were incubated for 30 min at 4° C. then washed with PBS five times. For peptide attachment, the imaging chamber was filled with peptide±qdot conjugate solution (~0.25 mL/chamber) taken from the 80 mL batch described above. Cells were incubated for 30 min at 4° C., then washed five times with PBS. Following staining, cells ere stored in Dulbecco's PBS (with $Ca^{2+}$ and $Mg^{2+}$, GIBCO) at 4° C.

Figure 18:
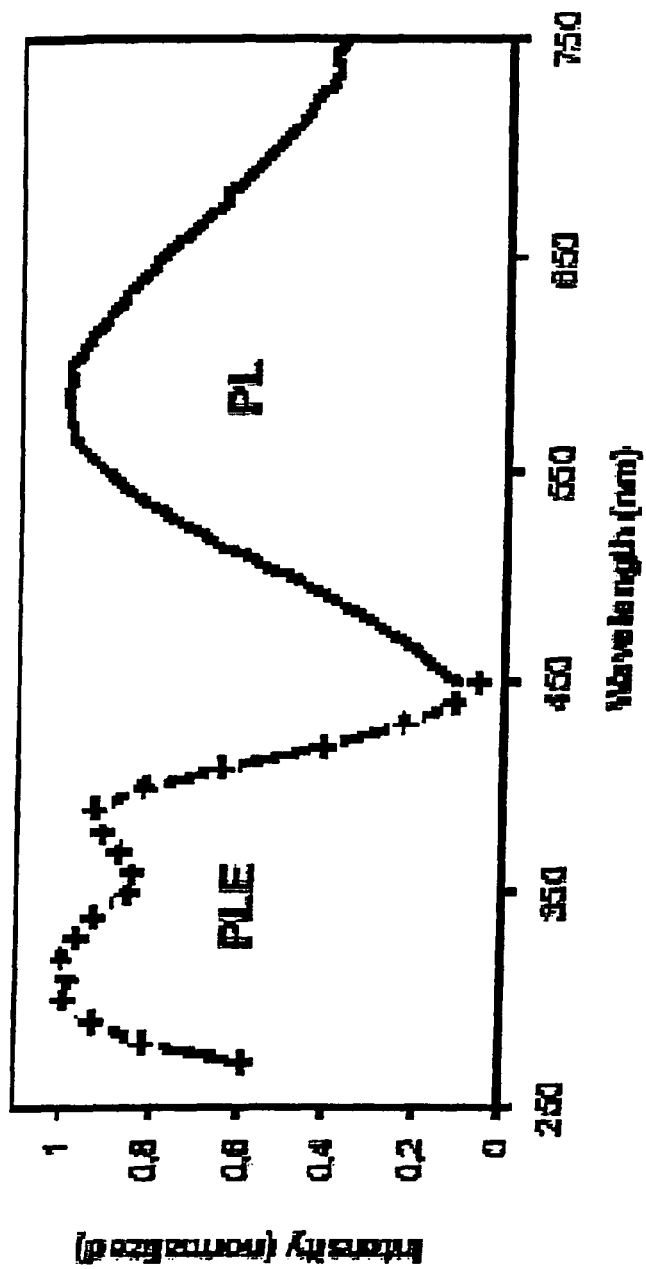
FIG. 18 depicts an example of room temperature photoluminescence (PL) and photoluminescence excitation (PLE) spectra of CdS qdots.

FIG. 18 depicts an example of room temperature photoluminescence (PL) ($\lambda_{exc}$=400 nm) and photoluminescence excitation (PLE) ($\lambda_{em}$=600 nm) spectra of CdS qdots dispersed at pH 7.4 in PBS.

Figure 19:
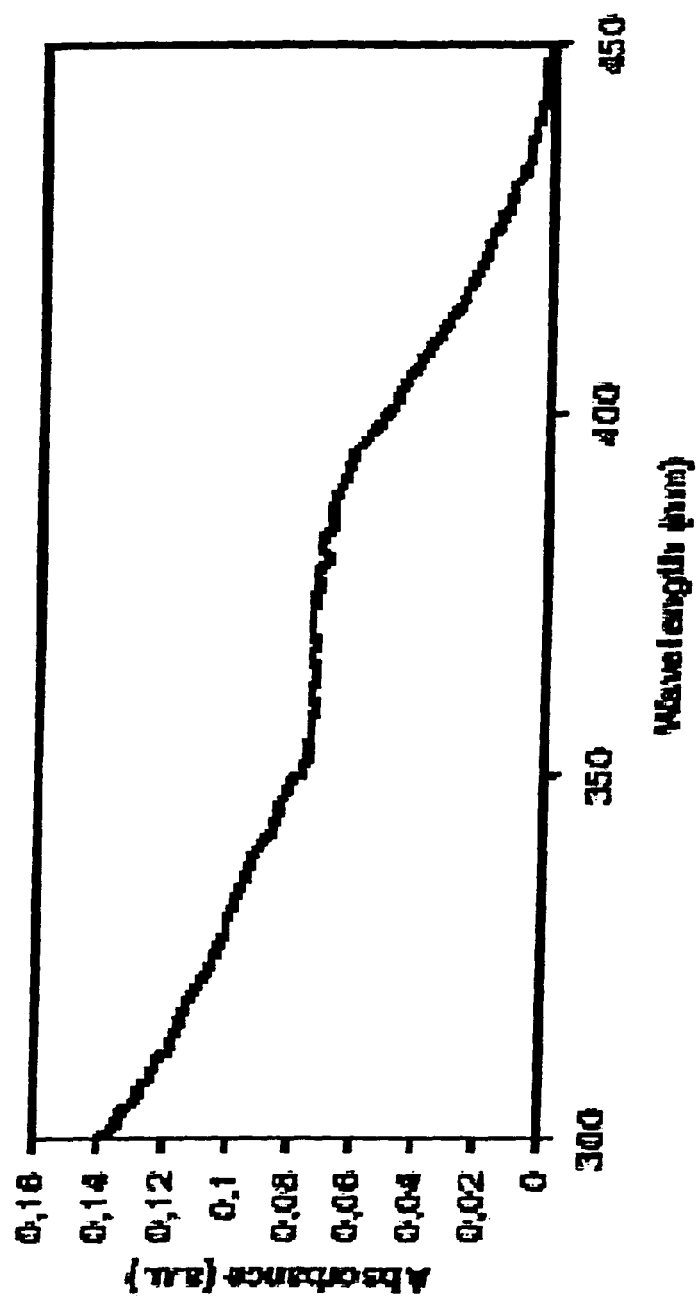
FIG. 19 depicts an example of room temperature absorbance spectrum of an aqueous dispersion of CdS quantum dots.

FIG. 19 depicts an example of room temperature absorbance spectrum of an aqueous dispersion of CdS qdots. The exciton peak at absorbance spectrum of an aqueous dispersion of CdS qdots. The exciton peak at 380 nm (3.6 eV) corresponds to an average particle size of ~30 angstroms.

Figure 20:
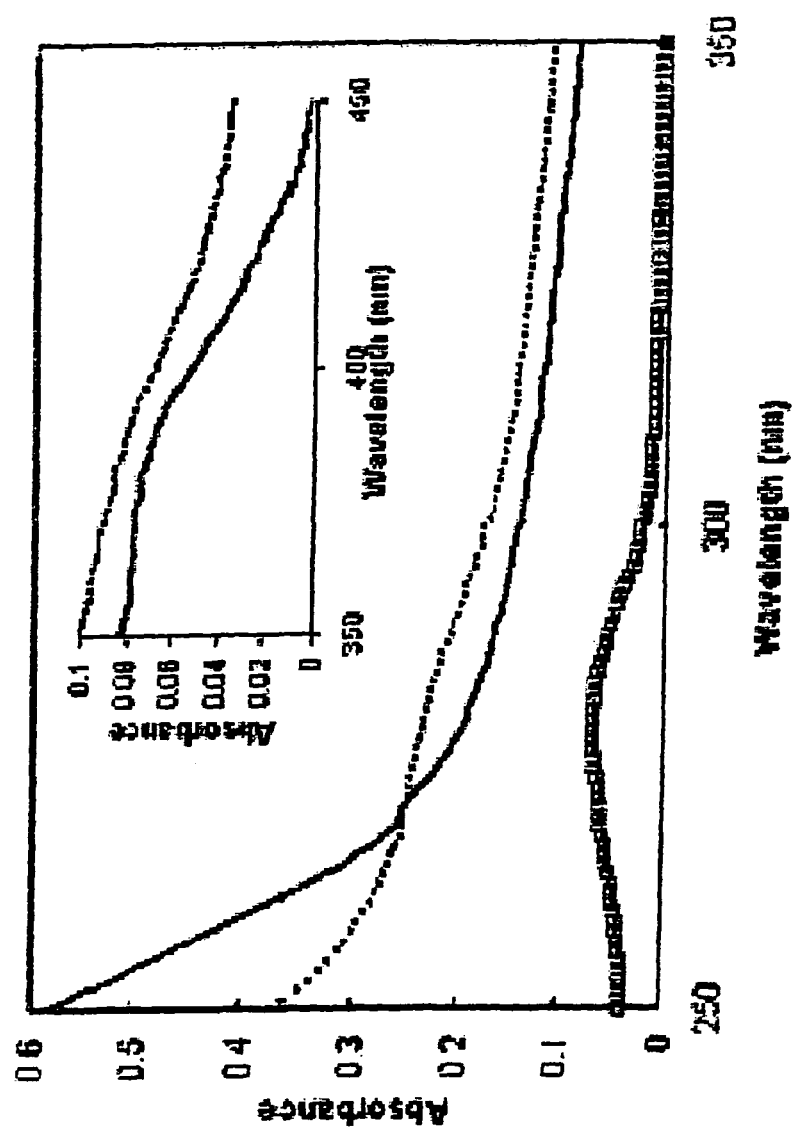
FIG. 20 depicts an example of room temperature absorbance spectra of CdS qdots and CdS/antibody complexes.

FIG. 20 depicts an example of room temperature absorbance spectra of CdS qdots and CdS/antibody complexes. IgG absorbs at 280 nm (squares). After binding IgG, the qdot absorbance spectrum (dashed) also exhibits this feature, which is absent in bare qdots (solid). Inset: CdS qdots bound to IgG (dashed) exhibit the same exciton peak as bare qdots (solid) at 380 nm. The absorbance of antibody-qdot complexes is slightly reduced due to less than 100% reaction yields. All materials were dispersed in PBS buffer (pH 7.4).

Example 10

Synthesis of Organic Monolayer-Stabilized Copper Nanoparticles in Supercritical Water Nanoparticle Synthesis: Copper(II) nitrate hemipentahydrate (Aldrich), copper(II) acetate monohydrate (Acros), and 1-hexanethiol (95%, Aldrich) were used as received without further purification. The experimental apparatus consisted of a pumping system and a ⅞-in.-i.d., 4-in.-long 316 stainless steel reaction cell (10 mL). For reactions without thiols, the cell was initially loaded at ambient conditions with 1.0 mL of pure water. For reactions with thiols, 900 μL of pure water with 100 μL of 1-hexanethiol was used (initial water:thiol mole ratio ~70:1). The cell was sealed and heated to 400° C. and ~173 bar using heating tape (Barnstead/Thermolyne) and an Omega temperature controller. The cell temperature was measured with a K-type thermocouple (Omega). A 0.02 M copper precursor solution was injected into the cell via 1/16-in.-i.d. stainless steel tubing by an HPLC pump (Beckman model 100A) at 4 mL/min until the operating pressure reached 413 bar. The solution reacts immediately upon entering the reactor, as observed visually in a separate experiment with an optical cell. The products precipitate upon cooling the reaction. The nanoparticles were removed from the cell with either deionized water (uncapped particles) or chloroform (organic capped particles). In the case of the thiol capped nanoparticles, unreacted precursor was removed by extraction with water. The nanoparticles were filtered (Fisher, qualitative P5) to remove large agglomerates of uncapped nanoparticles and dried using a rotary evaporator (Buchi). The nanoparticles redisperse in either deionized water (uncapped particles) or chloroform (organic capped particles).

Phase Behavior of Supercritical Water and 1-Hexanethiol: The water and 1-hexanethiol phase equilibria were studied in a titanium grade 2 optical cell equipped with sapphire windows. Under the reaction conditions of 400° C. and ~413 bar (50 μL of 1-hexanethiol in 150 μL of water), water and 1-hexanethiol are miscible. This miscibility is consistent with the phase diagram for n-alkanes in water (n-pentane and n-heptane).

Characterization Method: Gas chromatography (GC) measurements of hexanethiol were recorded with a Hewlett-Packard 5890A gas chromatograph Fourier transform infrared (FTIR) spectroscopy measurements were performed using a Perkin-Elmer Spectrum 2000 spectrometer with the nanoparticles dispensed on PTFE cards. Lowresolution transmission electron microscopy (TEM) images were obtained on a JEOL 200CX transmission electron microscope operating with a 120-kV accelerating voltage, while high-resolution transmission electron microscopy (HRTEM) images and selected area electron diffraction (SAED) patterns were obtained with a Gatan digital photography system on a JEOL 2010 transmission electron microscope with 1.7-Å point-to-point resolution operated with a 200-kV accelerating voltage. All samples were prepared on Electron Microscope Sciences 200-mesh carbon-coated aluminum grids by dispersing suspended nanoparticles onto the grid and evaporating the solvent. The measured lattice separations were indexed against standards for copper, $Cu_2O$, and CuO. UV-visible absorbance spectroscopy was performed using a Varian Cary 300 UV-visible spectrophotometer with the capped nanoparticles dispersed in chloroform. X-ray photoelectron spectroscopy (XPS) was performed on a Physical Electronics XPS 5700, with a monochromatic Al X-ray source (Ka excitation at 1486.6 eV). For XPS, the amples were deposited on a silicon wafer (cleaned with a 50:50 mixture of ethanol/HCl), vacuum-dried at 25° C. to remove all residual solvent, and stored under nitrogen.

Figure 22:
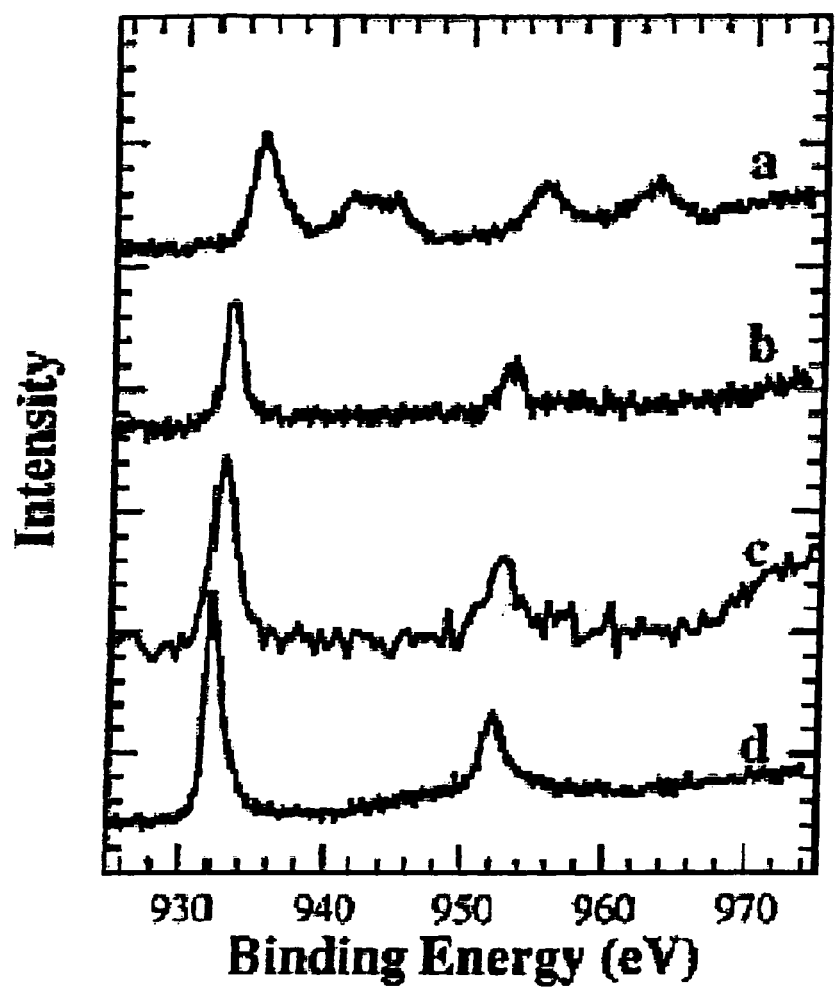
FIG. 22 depicts examples of X-ray Photoelectron spectroscopy (XPS) of uncapped and capped copper nanoparticles.

FIG. 22 depicts examples of X-ray Photoelectron spectroscopy (XPS) of uncapped particles produced via (a) $Cu(NO_3)_2$ and (b) $Cu(CH_3COO)_2$ and XPS scan of organically capped nanoparticles produced with (c) $Cu(NO_3)_2$ and (d) $Cu(CH_3COO)_2$. All scans are offset for clarity. Cu 2p core level binding energy for copper(II) at 934 eV and copper(0) at 932 eV.

Figure 23:
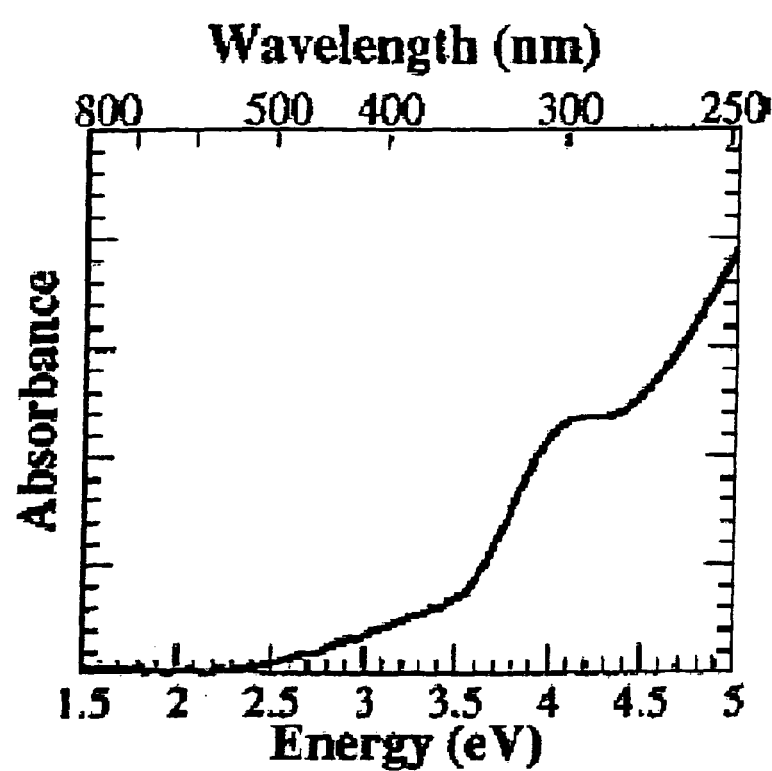
FIG. 23 depicts an example of room-temperature UV-visible spectra of organically capped copper nanoparticles.

FIG. 23 depicts an example of room-temperature UV-visible spectra of organically capped copper nanoparticles synthesized via $Cu(NO_3)_2$ and 1-hexanethiol.

Example 11

Electrogenerated Chemiluminescence from Nanopartidles

Figure 31:
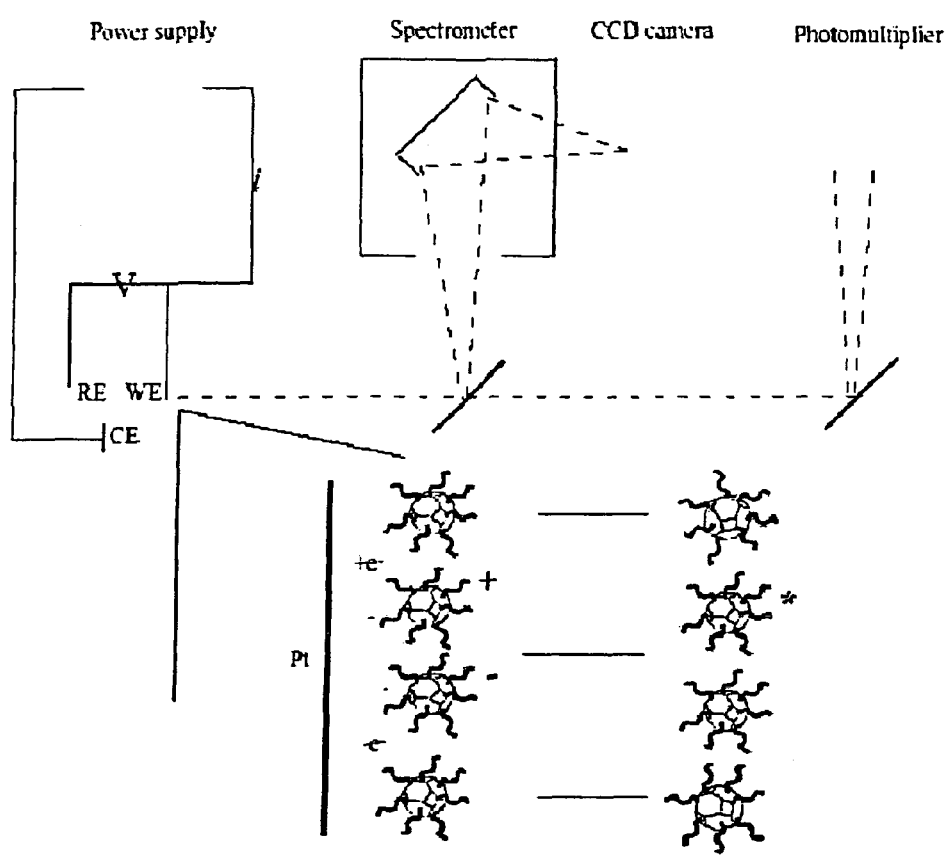
FIG. 31 depicts a schematic of an experimental setup for electrochemistry and electrogenerated chemiluminescence of nanoparticles.

FIG. 31 depicts a schematic experimental setup for electrochemistry (such as cyclic voltammetry, differential pulse voltammetry) and electrogenerated chemiluminescence (ECL) of Si nanoparticles. A cylindrical Pyrex vial 1.2 cm in diameter was used as electrochemical cell, where a 1 or 2 mm Pt disk, Pt coil and silver wire served as working (WE), counter (CE) and reference (RE) electrodes respectively. The ECL signal was recorded on the charge coupled device (CCD) camera. ECL could also be measured by a photomultiplier tube (PMT) and recorded as cyclic voltammetric ECL or ECL transients. The diagram below illustrates the ECL process in the vicinity of the working electrode through annihilation of electrochemically produced anion and cation radicals by stepping to the reduction and oxidation potentials alternatively.

Figure 32:
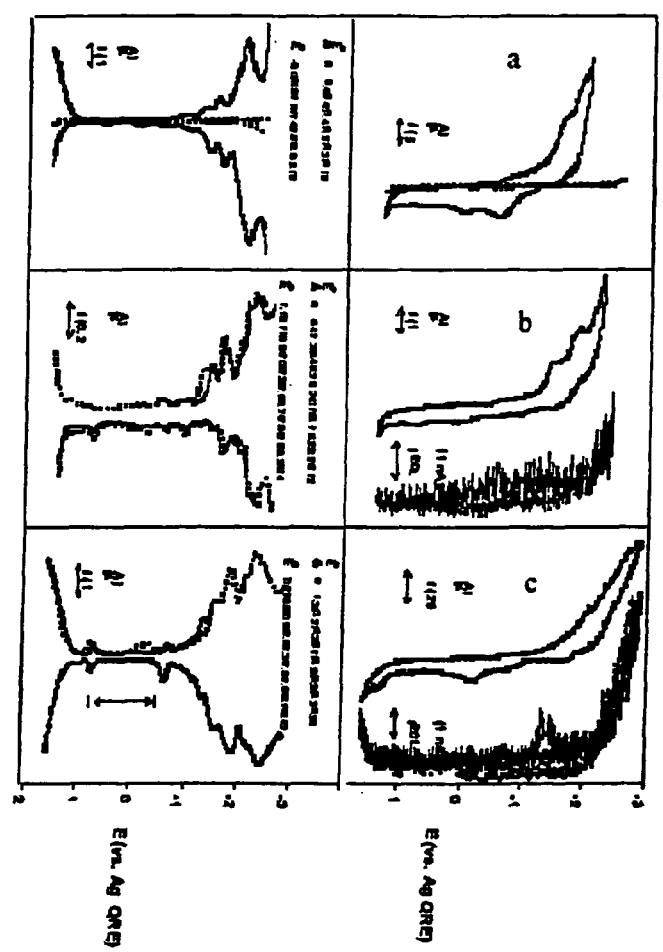
FIG. 32 depicts several examples of cyclic voltammograms and differential pulse voltammograms for several batches of silicon nanoparticles.

FIG. 32 depicts cyclic voltammograms and differential pulse voltammograms for several batches of Si nanoparticles in 0.1M tetrahexylammonium perchlorate (THAP), N,N'-dimethylformamide (DMF) solution. The nanoparticles size and dispersion were (a) 2.77±0.37, (b) 2.96±0.91 (c) 1.74±0.67 nm. Cyclic voltammetric ECL-voltage curves are plotted in (b) and (c). Dotted curves in (a) represent the response of the blank supporting electrolyte solution.

Figure 33:
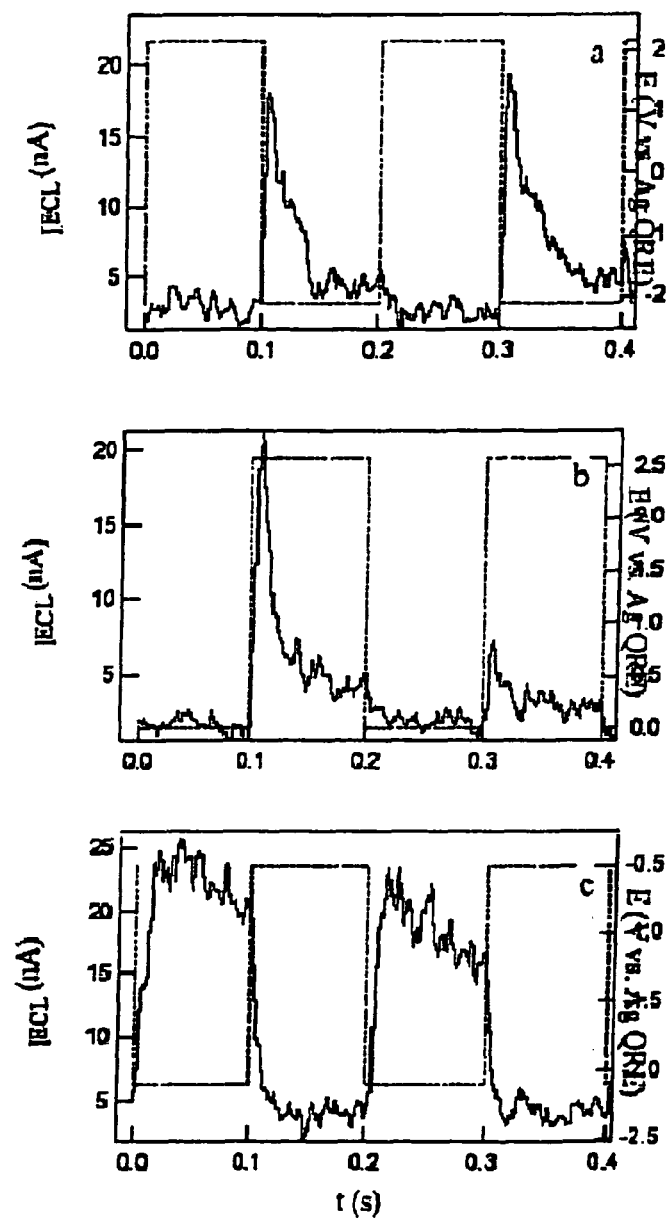
FIG. 33 depicts several examples of electrogenerated chemiluminescence transients.

FIG. 33 depicts ECL transients for (a) annihilation of cation and anion radicals in 0.1 M THAP acetonitrile (MeCN) solution, (b) oxalate coreactant system with 2.5 mM tetrabutyl ammonium oxalate added to the solution of (a), and (c) persulfate coreactant system in 0.1M THAP DMF solution with 6 mM tetrabutylammonium persulfate added. The size of the nanoparticles is around 2-4 nm in diameter.

Figure 34:
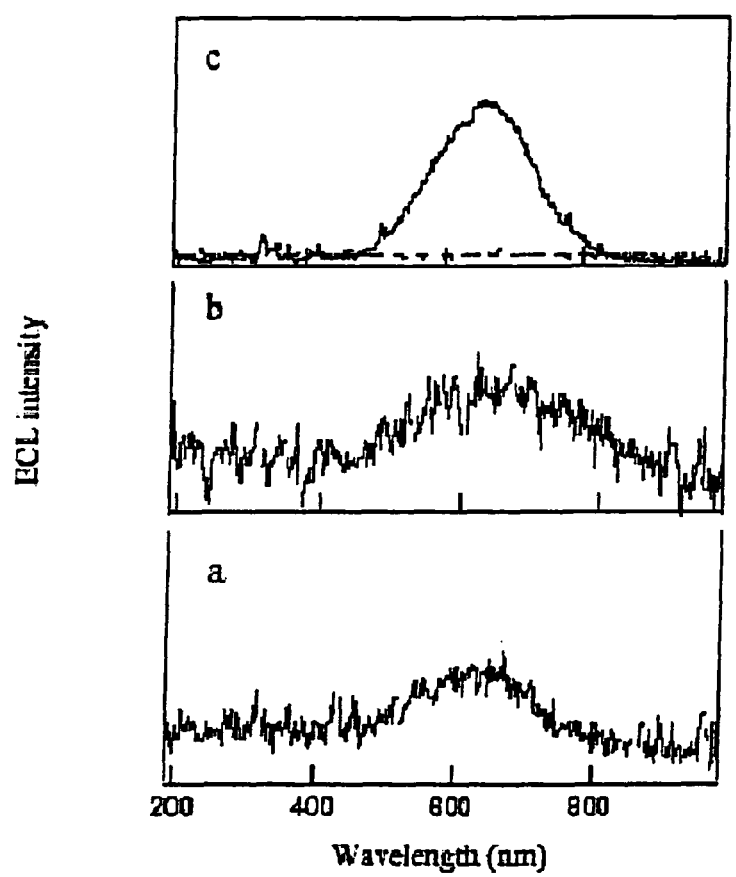
FIG. 34 depicts several examples of electrogenerated chemiluminescence spectra.

FIG. 34 depicts ECL spectra for (a) annihilation of cation and anion radicals by stepping the potential between 2.7 and −2.1V at 10 Hz with integration time 30 min in the same solution as FIG. 33(a), (b) oxalate coreactant system, stepping the potential between 0.1 and 3V at 10 Hz; integration time 40 min in the same solution as FIG. 33(b), and (c) persulfate coreactant system, stepping the potential between −0.5 and −2.5V at 10 Hz; integration time 10 min in the same solution as FIG. 33(c). The dotted curve in (c) is the ECL spectrum for the blank solution.

Figure 35:
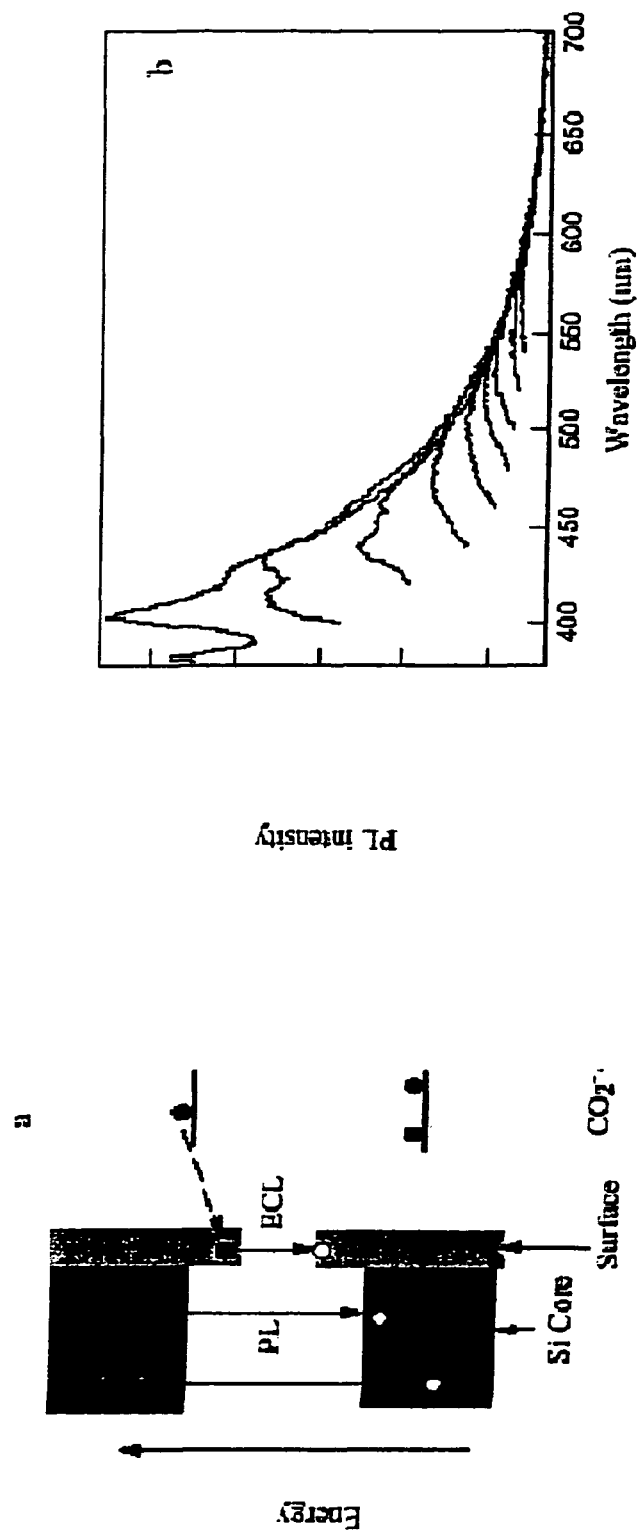
FIG. 35 depicts a schematic of an embodiment of a mechanism for electrogenerated chemiluminescence and photoluminescence of silicon clusters and an example of a photoluminescence spectra at different excitation energy.

FIG. 35 depicts (a) Schematic mechanisms for ECL and photoluminescence (PL) of Si clusters. (b) PLspectra at different excitation energy recorded with the same solution as for FIG. 33(a). The excitation wavelength from top to bottom was between 360 and 520 nm at 20 nm intervals.

Sterically stabilized silicon nanoparticles are chemically stable under electrochemical electron and hole injection. Differential pulse voltammetry reveals a large electrochemical gap separating the onset of electron and hole injection, related to the sizedependent HOMO-LUMO gap, and discrete charging events with increased electron injection due to Coulomb blockade effects. The negatively and positively charged nanoparticles produced visible light upon electron transfer between nanoparticles, or nanoparticles and redox active coreactants, in solution. This is the first example of electrogenerated chemiluminescence from semiconductor nanoparticles. The energetic difference between ECL and PL is believed to result from the greater sensitivity of the electron and hole wave functions with surface states during electrochemical charge transfer compared to optical excitation. These results reveal that nanoparticles of the elemental semiconductor, silicon, are more chemically robust than the compound semiconductor nanoparticles studied to date. The silicon nanoparticles have the ability to store charge in solution, which can subsequently lead to light emission upon electron and/or hole transfer. This quality provides electrochemically sensitive optoelectronic properties that may find future use in new sensor technologies.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Example 12

The following example utilizes silicon nanoparticles that have hydrophobic organic ligands. The Si-nanoparticles were encapsulated in the hydrophobic core of a micelle to make them water soluble, while still maintaining luminescence seen with the hydrophobic Si-nanoparticles dispersed in chloroform.

Experimental Procedure

First, octyl-β-D-glucopyranoside (detergent) was added to L-α-phosphatidycholine (lipid), both dispersed in chloroform. Next, silicon nanoparticles were added, also dispersed in chloroform, to the lipid/detergent mixture. After forming the lipid/detergent mixture, chloroform was removed by evaporation on a rotary evaporator, and then distilled water was added. Lastly, the final solution was sonicated until an optically clear dispersion was obtained.

Results

Figure 36:
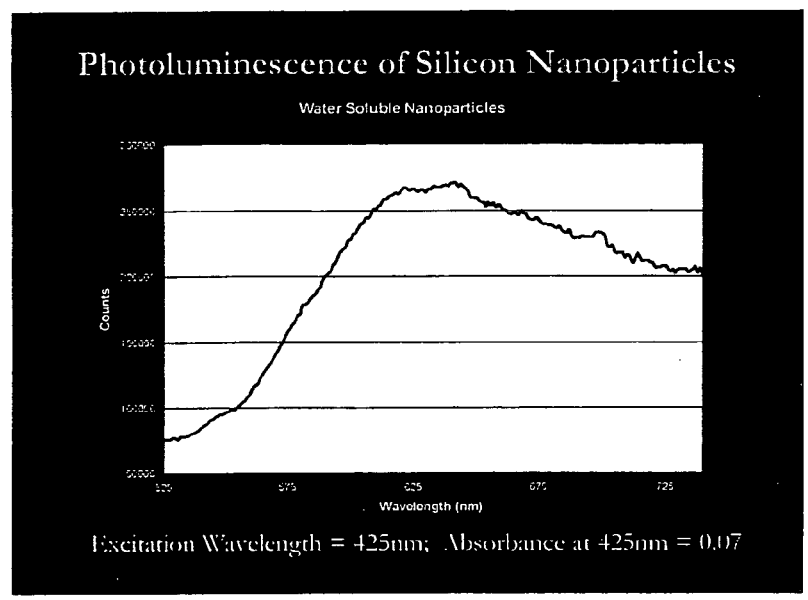
FIG. 36 is a graph depicting the photoluminescence of Si nanoparticles.

An even dispersion of luminescence was seen under the UV lamp. Photoluminescence emission spectra showed that the nanoparticles retained their luminescence in the aqueous environment, but the quantum yield drops by about a factor of 10. The silicon nanoparticles are water soluble and still produce luminescence as shown in FIG. 36.

Another embodiment of the present invention is watersoluble nanoparticles based on formation of liposome/detergent micelles for dispersion, wherein the nanoparticles are encapsulated in the hydrophobic core of a micelle and luminescence is maintained. Preferably, the Group IV nanoparticles are used, and preferably the Group IV nanoparticles are coated with an organic layer. Preferably, the organic layer is an alkene, more preferably octene or dodecene. The outer organic layer of the nanoparticles can optionally further be overcoated with surfactants to allow water solubility.

Mixed micelles are formed with a mixture of one or more lipids a lipid and one or more detergents for encapsulation of Group IV nanoparticles to form a stable dispersion in a polar solvent, including water, different alcohols, or acetone for example. Preferred lipids according to this embodiment of the invention include synthetic and naturally-occurring lipids with anionic, cationic, zwitterionic or non-ionic headgroups. The lipid headgroup may be attached to the hydrophobic tails by either ester or ether linkages. The detergents may be anionic, cationic, zwitterionic or non-ionic, with either high or low critical micelle concentrations (CMCs). The lipids and detergents may contain polymerizable headgroups, or tails. The surfactants may be single-chained, such as sodium dodecyl suphate, stearic acid, hexadecyl trimethylammonium bromide, pentaoxyethylene dedecyl ether, or lysolecithin, or double-chained, such as phosphatidyl serine, phosphatidyl ethanolamine, phosphatidyl choline, lecithin, phosphatidic acid, aerosol OT, dihexadecyl dimethylammonium bromide, digalactosyldiglyceride or monogalactosyldiglyceride.

Still another embodiment of the present invention is a method of determining the presence or absence of one or more target substances, comprising contacting a target area or sample which may contain the target substance or substances with an agent having affinity for the target substance or substances, wherein the affinity agent or agents are linked to a luminescent nanoparticle, wherein said nanoparticle is encapsulated in a micelle, said micelle comprising at least one detergent and at least one lipid; and examining the target area or sample for luminescence, said luminescence indicating that the target substance is present. Such a method may be applied where the target area is in a living organism, making it possible, for example, to image a diseased area such as a tumor by selecting an affinity agent with the right affinity. The sample of this method may be a biological material, such as a blood, serum, or urine sample. Various affinity agents are well known in the art which can be linked to the solubilized nanoparticles of the present invention, including antibodies tissue-specific liposomes.

In a preferred embodiment of this detection method, the target area or sample is examined for luminescence by applying energy capable of exciting said nanoparticle to emit electromagnetic radiation and detecting said electromagnetic radiation emitted by said nanoparticle. Preferably, the nanoparticles comprise a Group IV metal. Still more preferably, the Group IV metal is silicon. In addition, the nanoparticles may be nanowires, including the nanowires described above in the present specification.

Preferably, the nanoparticle is covalently linked to the affinity agent, though other linkages known in the art may be used depending on the nature of the detection method and how stable the linkage needs to be in the environment of that detection method.

When silicon nanoparticles are used, an advantage of this detection method is that silicon is generally regarded as a less toxic substance than other semiconductor nanoparticles such as CdSe. Accordingly, silicon nanoparticles may advantageously be used for in vivo detection methods according to the invention.

Still another embodiment of the present invention is a method and composition for identifying a product or material utilizing the solubilized luminescent nanoparticles of the invention. The solubilized nanoparticles can be dispersed in an area on the surface of the product or material and detected by applying energy which causes excitation of the nanoparticles that can be visually observed or detected by techniques known in the art. Multiple sizes or types of solubilized nanoparticles may be used to create multiple colors.

For example, the pharmaceutical industry is losing huge sums of money each year due to counterfeit pills. Marking the package with a detectable tag does not adequately address the problem because counterfeiters may simply remove the pills from the packaging. The solubilized luminescent nanoparticles of the present invention can be embedded in the surface coating put on pills and tablets, which is often a sugar coating, or it may be dispersed within the same inert ingredients in the core of a pill or tablet. They may also be embedded in gel caps or in liquid medications, including suspensions.

Other areas in which solubilized nanoparticles may be used to help identify products and materials include tickets (such as those for sporting events, concerts, and theaters), media (including CDs, software, and DVDs), brand products (designer clothing and auto parts), identification (including drivers' licenses, medical ID, and passports), and financial products (including credit cards, bank checks, and currency).

When solubilized silicon nanoparticles are used for identifying products or materials, one advantage is that they are very bright with good efficiency in the near infra-red range. They also exhibit long lifetimes and may enable two-photon excitation. Silicon is the only phosphor that has a red signature with UV absorption.

In this embodiment for identifying a product or material with solubilized nanoparticles of the present invention, it is also possible to "write" a desired label, such as a logo, product name, text or other symbols utilizing the solubilized nanoparticles. This can be accomplished by inkjet printing, stamping, or screen printing, for example. The pattern or symbol may be used alone or together with a uniform dispersion, where multiple colors are used to set apart the background dispersion color from the label color.

The present application further makes reference to the following publications, which are hereby expressly incorporated by reference into the present application:

1. Dubertret, Benoit, et al., "In Vivo Imaging of Quantum Dots Encapsulated in Phospholipid Micelles," *Science*, 298, pp. 1759-62 (November 2002).
2. Korgel, Brian A., et. al., "Synthesis of Size-Monodisperse CdS Nanocrystals Using Phosphatidylcholine Vesicles as True Reaction Compartments," *J. Phys. Chem.* 100, pp. 346-51 (1996).
3. Korgel, Brian A., et. al., "Vesicle Size Distributions Measured by Flow Field-Flow Fractionation Coupled with Multiangle Light Scattering," *Biophysical Journal* 74, pp. 3264-72 (June 1998).

What is claimed is:

1. A device, comprising:
   a source region and a drain region having a channel disposed between them; and
   a gate disposed adjacent to the channel and comprising at least one nanoparticle wherein the at least one nanoparticle comprises a crystalline material selected from the group consisting of Si and Ge, and has an average particle diameter of between about 1 to about 100 angstroms; wherein said at least one nanoparticle contains a capping agent, wherein said capping agent has the formula $(R)_n$—X, wherein X is an atom or functional group bound to the surface of the at least one nanoparticle, wherein n is an integer, and wherein each R moiety is independently hydrogen or an alkyl or aryl group having from 1 to 20 carbon atoms.

2. The device of claim 1, wherein the gate is a floating gate.

3. The device of claim 2, further comprising:
   a control gate positioned substantially adjacent to the floating gate;
   wherein the floating gate is positioned between the channel and the control gate.

4. The device of claim 3, further comprising:
   a dielectric material disposed between the control gate and the floating gate.

5. The device of claim 2, wherein the at least one nanoparticle exhibits quantized charging.

6. The device of claim 1, wherein the floating gate is disposed above the channel.

7. The device of claim 1, wherein said capping agent is a polar capping agent.

8. The device of claim 1, wherein said capping agent is a hydrocarbon capping agent.

9. The device of claim 1, wherein X is selected from the group consisting of N, C, O, S and P.

10. The device of claim 1, wherein X is selected from the group consisting of carboxylates, sulfonates, amides, alkynes, amines, alcohols, hydroxyls, thioethers, phosphates, alkynes, ethers, and quaternary ammonium groups.

11. The device of claim 1, wherein said capping agent is selected from the group consisting of alcohols, alkenes, alkynes, thiols, ethers, thioethers, phosphines, amines, amides, carboxylates, sulfonates, and quaternary ammonium compounds.

12. The device of claim 1, wherein said capping agent is selected from the group consisting of octanol, thiooctanol, and octane.

13. The device of claim 1, wherein said channel comprises a Group IV nanowire.

14. The device of claim 13, wherein the device is a transistor.

15. The device of claim 1, wherein the device is a memory device.

16. The device of claim 1, wherein the device is a flash memory device.

17. The device of claim 1, wherein the device is an EPROM or EEPROM device.

18. The device of claim 1, wherein the at least one nanoparticle is a silicon nanoparticles and is disposed in a polymeric matrix.

19. The device of claim 1, wherein said at least one nanoparticle comprises Si.

20. The device of claim 1, wherein said at least one nanoparticle comprises Ge.

21. The device of claim 1, wherein the capping agent is covalently bound to the at least one nanoparticle.

22. The device of claim 1, wherein the at least one nanoparticle is doped.

23. The device of claim 1, wherein the at least one nanoparticle is a nanowire.

24. A device, comprising:
- a source region and a drain region having a channel disposed between them which comprises a Group IV nanowire; and
- a gate disposed adjacent to the channel;

wherein the nanowire comprises a crystalline material selected from the group consisting of Si and Ge and has an average diameter of between about 1 to about 100 angstroms, wherein said nanowire contains a capping agent, and wherein said capping agent has the formula $(R)_n$—X, wherein X is an atom or functional group bound to the surface of the nanowire, wherein n is an integer, and wherein each R moiety is independently hydrogen or an alkyl or aryl group having from 1 to 20 carbon atoms.

* * * * *